(12) United States Patent
Zheng et al.

(10) Patent No.: US 10,281,398 B2
(45) Date of Patent: May 7, 2019

(54) LITHOGRAPHIC SYSTEMS AND METHODS

(71) Applicant: BOARD OF REGENTS, THE UNIVERSITY OF TEXAS SYSTEM, Austin, TX (US)

(72) Inventors: Yuebing Zheng, Austin, TX (US); Linhan Lin, Austin, TX (US); Xiaolei Peng, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/777,957

(22) PCT Filed: Dec. 13, 2016

(86) PCT No.: PCT/US2016/066291
§ 371 (c)(1),
(2) Date: May 22, 2018

(87) PCT Pub. No.: WO2017/106145
PCT Pub. Date: Jun. 22, 2017

(65) Prior Publication Data
US 2018/0348128 A1    Dec. 6, 2018

Related U.S. Application Data

(60) Provisional application No. 62/266,829, filed on Dec. 14, 2015.

(51) Int. Cl.
*G01N 21/552* (2014.01)
*G03F 7/20* (2006.01)

(52) U.S. Cl.
CPC ....... *G01N 21/553* (2013.01); *G03F 7/70025* (2013.01)

(58) Field of Classification Search
CPC .......................... G01N 21/553; G03F 7/70025
(Continued)

(56) References Cited

U.S. PATENT DOCUMENTS

| 4,425,261 A | 1/1984 | Stenius et al. |
| 6,016,226 A | 1/2000 | Arisawa et al. |

(Continued)

OTHER PUBLICATIONS

Ahmed, et al., "Rotational Manipulation of Single Cells and Organisms Using Acoustic Waves", Nat. Commun. 2016, 7.

(Continued)

*Primary Examiner* — Tri T Ton
(74) *Attorney, Agent, or Firm* — Meunier Carlin & Curfman LLC

(57) ABSTRACT

Disclosed herein are lithographic systems and methods. For example, disclosed herein are methods comprising illuminating a first location of a plasmonic substrate with electromagnetic radiation; wherein the electromagnetic radiation comprises a wavelength that overlaps with at least a portion of the plasmon resonance energy of the plasmonic substrate; and wherein the plasmonic substrate is in thermal contact with a liquid sample comprising a plurality of particles; thereby: generating a bubble at a location in the liquid sample proximate to the first location of the plasmonic substrate, the bubble having a gas-liquid interface with the liquid sample; trapping at least a portion of the plurality of particles at the gas-liquid interface of the bubble and the liquid sample; and depositing at least a portion of the plurality of particles on the plasmonic substrate at the first location.

20 Claims, 36 Drawing Sheets

(58) Field of Classification Search
USPC .................................................. 356/432–448
See application file for complete search history.

(56) References Cited

U.S. PATENT DOCUMENTS

| | | | |
|---|---|---|---|
| 8,431,903 | B2 | 4/2013 | Baaske et al. |
| 2005/0281944 | A1 | 12/2005 | Jang et al. |
| 2008/0245430 | A1 | 10/2008 | Adleman et al. |
| 2009/0034053 | A1 | 2/2009 | King et al. |
| 2010/0142038 | A1 | 6/2010 | Sugiura et al. |
| 2011/0084218 | A1 | 4/2011 | Duhr et al. |
| 2015/0111199 | A1 | 4/2015 | Hart et al. |
| 2015/0204810 | A1 | 7/2015 | Pan et al. |
| 2015/0316480 | A1 | 11/2015 | Baaske et al. |
| 2015/0380120 | A1 | 12/2015 | Nnanna et al. |
| 2018/0236486 | A1* | 8/2018 | Zheng ...................... B05D 3/06 |

OTHER PUBLICATIONS

Ahn, et al., "Heterogenous Three-Dimensional Electronics by Use of Printed Semiconductor Nanomaterials", Science 2006, 314(5806), 1754-1757.
Ahn, et al., "Photonic- plasmonic mode coupling in on-chip integrated optoplasmonic molecules", ACS Nano 6, 951-960 (2012).
Alois, et al., "Thermal non-equilibrium transport in colloids", Reports on Progress in Physics 2010, 73(12): 126601.
Anderson, JL, "Colloid Transport by Interfacial Forces", Annu. Rev. Fluid Mech. 1989, 21, 61-99.
Angmo, et al., "Roll-to-Roll Inkjet Printing and Photonic Sintering of Electrodes for ITO Free Polymer Solar Cell Modules and Facile Product Integration", Adv Energy Mater 2013, 3(2), 172-175.
Arias-Gonzélez, et al., "Optical forces on small particles: Attractive and repulsive nature and plasmon-resonance conditions", J. Opt. Soc. Am. A 20, 1201-1209 (2003).
Ayala-Orozco, et al., "Au nanomatryoshkas as efficient near-infrared photothermal transducers for cancer treatment: Benchmarking against nanoshells.", ACS Nano 8, 6372-6381 (2014).
Babynina, et al., "Bending gold nanorods with light.", Nano Lett. 16, 6485-6490 (2016).
Baffou, et al., "Nanoscale Control of Optical Heating in Complex Plasmonic Systems.", ACS Nano 2010, 4(2), 709-716.
Baffou, et al., "Photoinduced Heating of Nanoparticle Arrays.", ACS Nano 2013, 7(8), 6478-6488.
Baffou, et al., "Super-Heating and Micro-Bubble Generation around Plasmonic Nanoparticles under cw Illumination", J Phys Chem C 2014, 118(9), 4890-4898.
Baffou, et al., "Thermo-plasmonics: Using metallic nanostructures as nano-sources of heat", Laser Photonics Rev. 7, 171-187 (2013).
Bagalkot, et al., "Quantum Dot-Aptamer Conjugates for Synchronous Cancer Imaging, Therapy, and Sensing of Drug Delivery Based on Bi-Fluorescence Resonance Energy Transfer", Nano Lett, 2007, 7, 3065-3070.
Banzer, et al., "Chiral optical response of planar and symmetric nanotrimers enabled by heteromaterial selection", Nat. Commun. 7, 13117 (2016).
Bao, et al., "Optical Printing of Electrodynamically Coupled Metallic Nanoparticle Arrays", J. Phys. Chem. C 2014, 118, 19315-19321.
Bao, et al., "Patterning Fluorescent Quantum Dot Nanocomposites by Reactive Inkjet Printing", Small 2015, 11(14), 1649-1654.
Baral, et al., "Comparison of Vapor Formation of Water at the Solid/Water Interface to Colloidal Solutions Using Optically Excited Gold Nanostructures", ACS Nano 2014, 8, 1439-1448.
Barnes, et al., "Surface plasmon subwavelength optics", Nature 2003, 424(6950): 824-830.
Bendix, et al., "Optical trapping of nanoparticles and quantum dots", IEEE J. Sel. Top. Quantum Electron. 20, 15-26 (2014).
Berthelot, et al., "Three-dimensional manipulation with scanning near-field optical nanotweezers", Nat Nano 2014, 9(4): 295-299.

Blattmann, et al., "Plasmonic coupling dynamics of silver nanoparticles in an optical trap", Nano Lett. 15, 7816-7821 (2015).
Bockris, et al., "On the Structure of Charged Interfaces", Proc. R. Soc. London, A 1963, 274(1356): 55-79.
Boltasseva, et al., "Low-loss plasmonic metamaterials", Science 331, 290-291 (2011).
Bosanac, et al., "Efficient optical trapping and visualization of silver nanoparticles", Nano Lett. 8, 1486-1491 (2008).
Bradley, et al., "Clickable janus particles", J. Am. Chem. Soc. 138, 11437-11440 (2016).
Braun, et al., "Optically Controlled Thermophoretic Trapping of Single Nano-Objects", ACS Nano 2013, 7(12): 11200-11208.
Braun, et al., "Single molecules trapped by dynamic inhomogeneous temperature fields", Nano Lett. 15, 5499-5505 (2015).
Braun, et al., "Trapping of DNA by Thermophoretic Depletion and Convection", Phys. Rev. Lett. 2002, 89(18): 188103.
Braun, et al., "Trapping of Single Nano-Objects in Dynamic Temperature Fields", Phys. Chem. Chem. Phys. 2014, 16, 15207-15213.
Bregulla, et al., "Thermo-osmotic flow in thin films", Phys. Rev. Lett. 116, 188303 (2016).
Brown, et al., "Gold Nanoparticles for the Improved Anticancer Drug Delivery of the Active Component of Oxaliplatin", J. Am. Chem. Soc. 2010, 132, 4678-4684.
Brownlee, "Biochemistry and molecular cell biology of diabetic complications", Nature 2001, 414(6865): 813-820.
Campion, et al., "Surface-Enhanced Raman Scattering", Chem. Soc. Rev. 1998, 27, 241-250.
Cassette, et al., "Design of new quantum dot materials for deep tissue infrared imaging", Adv Drug Deliver Rev 2013, 65(5), 719-731.
Chen, et al., "Directed self-assembly of a colloidal kagome lattice", Nature 469, 381-384 (2011).
Chen, et al., "How to Light Special Hot Spots in Multiparticle-Film Configurations", ACS Nano 2015, 10, 581-587.
Chen et al., "Supracolloidal reaction kinetics of janus spheres", Science 331, 199-202 (2011).
Cheng, et al., "Light-triggered assembly of gold nanoparticles for photothermal therapy and photoacoustic imaging of tumors in vivo", Adv. Mater. 29, 1604894 (2017).
Chickaraddy, et al., "Single-Molecule Strong Coupling at Room Temperature in Plasmonic Nanocavities", Nature 2016, 535, 127-130.
Chiou, et al., "Massively parallel manipulation of single cells and microparticles using optical images", Nature 2005, 436(7049): 370-372.
Chou, et al., "DNA assembly of nanoparticle superstructures for controlled biological delivery and elimination", Nat. Nanotechnol. 9, 148-155 (2014).
Coskun, et al., "Polyol synthesis of silver nanowires: An extensive parametric study", Cryst. Growth Des. 11, 4963-4969 (2011).
Curto, et al., "Unidirectional Emission of a Quantum Dot Coupled to a Nanoantenna", Science 2010, 329(5994), 930-933.
Dahl, et al., "Composite Titanium Dioxide Nanomaterials", Chem. Rev. 2014, 114, 9853-9889.
Ding, et al., "On-chip manipulation of single microparticles, cells, and organisms using surface acoustic waves", Proc. Natl. Acad. Sci. 2012, 109(28): 11105-11109.
Ditlbacher, et al., "Silver nanowires as surface plasmon resonators", Phys. Rev. Lett. 95, 257403 (2005).
Duhr, et al., "Why molecules move along a temperature gradient", Proc. Natl. Acad. Sci. 103, 19678-19682 (2006).
Eastman, Ed, "Theory of the soret effect", J. Am. Chem. Soc. 50, 283-291 (1928).
Edwards, et al., "Depletion-Mediated Potentials and Phase Behavior for Micelles, Macromolecules, Nanoparticles, and Hydrogel Particles", Langmuir 2012, 28(39): 13816-13823.
Erb, et al., "Magnetic assembly of colloidal superstructures with multipole symmetry", Nature 457, 999-1002 (2009).
Fan, et al., "Self-assembled plasmonic nanoparticle cluster", Science 328, 1135-1138 (2010).
Fang, et al., "Evolution of Light-Induced Vapor Generation at a Liquid-Immersed Metallic Nanoparticle", Nano Lett 2013, 13(4), 1736-1742.

(56) References Cited

OTHER PUBLICATIONS

Fazio, et al., "SERS Detection of Biomolecules at Physiological Ph Via Aggregation of Gold Nanorods Mediated by Optical Forces and Plasmonic Heating", Sci. Rep. 2016, 6, 26952.
Feng, et al., "Re-entrant solidification in polymer- colloid mixtures as a consequence of competing entropic and enthalpic attractions", Nature Mater. 14, 61-65 (2015).
Friedrich, et al., "Surface Imaging Beyond the Diffraction Limit with Optically Trapped Spheres", Nat. Nanotechnol. 2015, 10, 1064-1069.
Fujii, et al., "Fabrication and Placement of a Ring Structure of Nanoparticles by a Laser-Induced Micronanobubble on a Gold Surface", Langmuir, 2011, 27(14), 8605-8610.
Galatsis, et al., "Patterning and Templating for Nanoelectronics", Adv Mater 2010, 22(6), 769-778.
Garces-Chavez, et al., "Simultaneous Micromanipulation in Multiple Planes Using a Self-Reconstructing Light Beam", Nature 2002, 419, 145-147.
Garcia-Leis, et al., "Silver Nanostars with High SERS Performance", J. Phys. Chem. C 2013, 117, 7791-7795.
Gargiulo, et al., "Connecting Metallic Nanoparticles by Optical Printing", Nano Lett. 2016, 16, 1224-1229.
Geissler, et al., "Patterning: Principles and Some New Developments", Adv. Mater. 2004, 16, 1249-1269.
Gluckstad, J, "Microfluidics: Sorting Particles with Light", Nat. Mater. 2004, 3, 9-10.
Gosse, et al., "Magnetic Tweezers: Micromanipulation and Force Measurement at the Molecular Level", Biophys. J. 2002, 82(6): 3314-3329.
Govorov, et al., "Generating heat with metal nanoparticles", Nano Today 2, 30-38 (2007).
Grier, DG, "A Revolution in Optical Manipulation", Nature 2003, 424, 810-816.
Grigorenko, et al., "Nanometric Optical Tweezers Based on Nanostructured Substrates", Nat. Photonics 2008, 2, 365-370.
Gu, et al., "Facile one-pot synthesis of bifunctional heterodimers of nanoparticles: A conjugate of quantum dot and magnetic nanoparticles", J Am Chem Soc 2004, 126(18): 5664-5665.
Gu, et al., "Tweezing and Manipulating Micro- and Nanoparticles by Optical Nonlinear Endoscopy", Light Sci Appl 2014, 3, e126.
Guck, et al., "The Optical Stretcher: A Novel Laser Tool to Micromanipulate Cells", Biophys. J. 2001, 81, 767-784.
Guffey, et al., "All-Optical Patterning of Au Nanoparticles on Surfaces Using Optical Traps", Nano Lett. 2010, 10, 4302-4308.
Guo, et al., "Controlling Cell- Cell Interactions Using Surface Acoustic Waves", Proc. Natl. Acad. Sci. 2015, 112, 43-48.
Guo, et al., "Modular assembly of superstructures from polyphenol-functionalized building blocks", Nat. Nanotechnol. 11, 1105-1111 (2016).
Halas, et al., "Plasmons in Strongly Coupled Metallic Nanostructures", Chem. Rev. 2011, 111, 3913-3961.
Hansen, et al., "Expanding the optical trapping range of gold nanoparticles", Nano Lett. 5, 1937-1942 (2005).
Hansen, et al., "Nano-Optical Conveyor Belt, Part I: Theory", Nano Lett. 2014, 14(6): 2965-2970.
Hashmi, et al., "Oscillating bubbles: a versatile tool for lab on a chip applications", Lab Chip 2012, 12, 4216-4227.
Haynes, et al., "Nanosphere Lithography: A versatile nanofabrication tool for studies of sie-dependent nanoparticle opticlas", J. Phys. Chem. B 2001, 105, 5599-5611.
Helden, et al., "Direct measurement of thermophoretic forces", Soft Matter 11, 2379-2386 (2015).
Hernandez-Santana, et al., "Nanolithography: Written with Light", Nature Nanotechnol. 2010, 5, 629-630.
Hildebrandt, et al., "Surface-Enhanced Resonance Raman Spectroscopy of Rhodamine 6G Adsorbed on Colloidal Silver", J. Phys. Chem. 1984, 88, 5935-5944.
Hoang, et al., "Ultrafast Room-Temperature Single Photon Emission from Quantum Dots Coupled to Plasmonic Nanocavities", Nano Lett 2016, 16(1), 270-275.
Hoang, et al., "Ultrafast Spontaneous Emission Source Using Plasmonic Nanoantennas", Nat. Commun. 2015, 6, 7788.
Hu, et al., "Hydrogel microrobots actuated by optically generated vapour bubbles", Lab Chip 2012, 12, 3821-3826.
Huang, et al., "Microfluidic integrated optoelectronic tweezers for single-cell preparation and analysis", Lab Chip 2013, 13, 3721-3727.
Huang, "Optoelectronic tweezers integrated with lensfree holographic microscopy for wide-field interactive cell and particle manipulation on a chip", Lab Chip 2013, 13, 2278-2284.
Huang, et al., "Reversal of the optical force in a plasmonic trap", Opt. Lett. 33, 3001-3003 (2008).
Hulteen, et al., "Nanosphere LithographyL Size-Tunable Silver Nanoparticle and Surface Cluster Arrays", J. Phys. Chem. B 1999, 103, 3854-3863.
Huo, et al., "Beam pen lithography", Nature Nanotechnol. 2010, 5, 637-640.
Huo, et al., "Polymer pen lithography", Science 2008, 321, 1658-1660.
Ilic, et al., "Exploiting Optical Asymmetry for Controlled Guiding of Particles with Light", ACS Photonics 2016, 3, 197-202.
Iracki, et al., "Charged Micelle Depletion Attraction and Interfacial Colloidal Phase Behavior", Langmuir 2010, 26(24): 18710-18717.
Ito, et al., "Pushing the limits of lithography", Nature 2000, 406, 1027-1031.
Jamshidi, et al., "NanoPen: Dynamic, Low-Power, and Light-Actuated Patterning of Nanoparticles", Nano Lett. 2009, 9, 2921-2925.
Jensen, et al., "Optical trapping and two-photon excitation of colloidal quantum dots using bowtie apertures", ACS Photonics, 2016, 3(3), 423-427.
Jin, et al., "Photoinduced Conversion of Silver Nanospheres to Nanoprisms", Science 2001, 294, 1901-1903.
Jones, et al., "DNA-nanoparticle superlattices formed from anisotropic building blocks", Nature Mater. 9, 913-917 (2010).
Juan, et al., "Plasmon nano-optical tweezers", Nat. Photonics 2011, 5(6): 349-356.
Juan, et al., "Self-induced back-action optical trapping of dielectric nanoparticles", Nat. Phys. 5, 915-919 (2009).
Kang, et al., "Low-power nano-optical vortex trappling via plasmonic diabolo nanaantennas", Nature Comm., 2011, 2, 1-6.
Kim, et al., "Full-colour quantum dot displays fabricated by transfer printing", Nat Photon 2011, 5(3), 176-182.
Kim, et al., "High-Resolution Patterns of Quantum Dots Formed by Electrohydrodynamic Jet Printing for Light-Emitting Diodes", Nano Lett 2015, 15(2), 969-973.
Kim, et al., "Multilayer Transfer Printing for Pixelated, Multicolor Quantum Dot Light-Emitting Diodes", ACS Nano 2016, 10(5), 4920-4925.
Kim, et al., "Transmutable nanoparticles with reconfigurable surface ligands", Science 351, 579-582 (2016).
Kimura, et al., "Photoinduced fluorescence enhancement in CdSe/ZnS quantum dot submonolayers sandwiched between insulating layers: Influence of dot proximity", J Phys Chem B 2004, 108(35), 13258-13264.
Klajn, et al., "Light-Controlled Self-Assembly of Reversible and Irreversible Nanoparticle Suprastructures", Proc. Natl. Acad. Sci. 2007, 104, 10305-10309.
Kneipp, et al., "Single Molecule Detection Using Surface-Enhanced Raman Scattering (SERS)", Phys. Rev. Lett. 1997, 78, 1667-1670.
Konstantatos, et al., "Ultrasensitive solution-cast quantum dot photodetectors", Nature 2006, 442(7099), 180-183.
Kraft, et al., "Surface roughness directed self-assembly of patchy particles into colloidal micelles", Proc. Natl. Acad. Sci. 109, 10787-10792 (2012).
Kramer, et al., "Plasmonic properties of silicon nanocrystals doped with boron and phosphorus", Nano Lett. 15, 5597-5603 (2015).
Kreysing, et al., "The Optical Cell Rotator", Opt. Express 2008, 16, 16984-16992.
Kundu, et al., "Light-Controlled Self-Assembly of Non-Photoresponsive Nanoparticles", Nat. Chem 2015, 7, 646-652.

(56) References Cited

OTHER PUBLICATIONS

Kyrsting, et al., "Heat Profiling of Three-Dimensionally Optically Trapped Gold Nanoparticles Using Vesicle Cargo Release", Nano Lett. 2011, 11, 888-892.
Lan, et al., "Charge-extraction strategies for colloidal quantum dot photovoltaics", Nat Mater 2014, 13(3), 233-240.
Lan, et al., "Ordering, positioning and uniformity of quantum dot arrays", Nano Today 2012, 7(2), 94-123.
Lee, et al., "Fano Resonance and Spectrally Modified Photoluminescence Enhancement in Monolayer Mos2 Integrated with Plasmonic Nanoantenna Array", Nano Lett. 2015, 15, 3646-3653.
Lee, et al., "InAs/GaAs Quantum-Dot Lasers Monolithically Grown on Si, Ge, and Ge-on-Si Substrates", IEEE J Sel Topics Quantum Electon 2013, 19(4).
Lehmuskero, et al., "Laser trapping of colloidal metal nanoparticles", ACS Nano 9, 3453-3469 (2015).
Leunissen, et al., "Ionic colloidal crystals of oppositely charged particles", Nature 437, 235-240 (2005).
Li, et al., "Absorption spectroscopy of single optically trapped gold nanorods", Nano Lett. 15, 7731-7735 (2015).
Li, et al., "Dimers of Silver Nanospheres: Facile Synthesis and Their Use as Hot Spots for Surface-Enhanced Raman Scattering", Nano Lett. 2009, 9, 485-490.
Li, et al., "Large-Scale Synthesis of Nearly Monodisperse CdSe/CdS Core/Shell Nanocrystals Using Air-Stable Reagents via Successive Ion Layer Adsorption and Reaction", J Am Chem Soc 2003, 125: 12567-12575.
Li, et al., "Ph-Programmable Self-Assembly of Plasmonic Nanoparticles: Hydrophobic Interaction Versus Electrostatic Repulsion", Nanoscale 2015, 7, 956-964.
Li, et al., "Reversible Plasmonic Circular Dichroism of Au Nanorod and DNA Assemblies", J. Am. Chem. Soc. 2012, 134, 3322-3325.
Lim, et al., "Highly Uniform and Reproducible Surface-Enhanced Raman Scattering from DNA-Tailorable Nanoparticles with 1-nm Interior Gap", Nat. Nanotechnol. 2011, 6, 452-460.
Lin, et al., "Bubble-Pen Lithography", Nano Lett 2016, 16(1), 701-708.
Lin, et al., "Light-directed reversible assembly of plasmonic nanoparticles using plasmon-enhanced thermophoresis", ACS Nano 10, 9659-9668 (2016).
Liu, et al., "Diamond family of nanoparticle superlattices", Science 351, 582-586 (2016).
Liu, et al., "Formation and dissolution of microbubbles on highly-ordered plasmonic nanopillar arrays", Scientific Reports, 2015, 5, 18515.
Liu, et al., "Nanoantenna-enhanced gas sensing in a single tailored nanofocus", Nat. Mater. 2011, 10, 631-636.
Liu, et al., "Thermoresponsive Assembly of Charged Gold Nanoparticles and Their Reversible Tuning of Plasmon Coupling", Chem. Int. Ed. 2012, 51, 6373-6377.
Lohse, "Surface nanobubbles and nanodroplets", Rev Mod Phys 2015, 87(3), 981-1035.
Lu, et al., "Synthesis and Self-Assembly of Au@SiO2 Core-Shell Colloids", Nano Lett. 2002, 2, 785-788.
MacFarlane, et al., "Nanoparticle superlattice engineering with DNA", Science 334, 204-208 (2011).
Manoharan, VN, "Colloidal matter: Packing, geometry, and entropy", Science 349, (2015).
Manz, et al., "Spatial organization and signal transduction at intercellular junctions", Nat. Rev. Mol. Cell Biol. 2010, 11(5): 342-352.
Markman, et al., "Photon-Counting Security Tagging and Verification Using Optically Encoded QR Codes", IEEE Photonics J 2014, 6(1).
Mashford, et al., "High-efficiency quantum-dot light-emitting devices with enhanced charge injection", Nat Photon 2013, 7(5), 407-412.
McHale, et al., "Bubble nucleation characteristics in pool boiling of a wetting liquid on smooth and rough surfaces", Int J Multiphas Flow 2010, 36(4), 249-260.
McLellan, et al., "The SERS Activity of a Supported Ag Nanocube Strongly Depends on Its Orientation Relative to Laser Polarization", Nano Lett. 2007, 7, 1013-1017.
Medintz, et al., "Quantum dot bioconjugates for imaging, labelling and sensing", Nat Mater 2005, 4(6), 435-446.
Medintz, "Self-assembled nanoscale biosensors based on quantum dot FRET donors", Nat Mater 2003, 2(9), 630-638.
Messina, et al., "Manipulation and Raman Spectroscopy with Optically Trapped Metal Nanoparticles Obtained by Pulsed Laser Ablation in Liquids", J. Phys. Chem. C 2011, 115, 5115-5122.
Min, et al., "Focused plasmonic trapping of metallic particles", Nat Commun 2013, 4, 2891.
Ndukaife, et al., "Long-range and rapid transport of individual nano-objects by a hybrid electrothermoplasmonic nanotweezer", Nat Nano 2016, 11(1): 53-59.
Nedev, et al., "Optical Force Stamping Lithography", Nano Lett. 2011, 11, 5066-5070.
Neumann, et al., "Solar Vapor Generation Enabled by Nanoparticles", ACS Nano 2013, 7(1), 42-49.
Nie, et al., "Probing Single Molecules and Single Nanoparticles by Surface-Enhanced Raman Scattering", Science 1997, 275, 1102-1106.
O'Brien, et al., "Programming colloidal crystal habit with anisotropic nanoparticle building blocks and DNA bonds", J. Am. Chem. Soc. 138 14562-14565 (2016).
Ohlinger, et al., "Optothermal escape of plasmonically coupled silver nanoparticles from a three-dimensional optical trap", Nano Lett. 11, 1770-1774 (2011).
Ozel, et al., "Coaxial Lithography", Nat. Nanotechnol. 2015, 10, 319-324.
Pang, et al., "Optical Trapping of Individual Human Immunodeficiency Viruses in Culture Fluid Reveals Heterogeneity with Single-Molecule Resolution", Nat. Nanotechnol. 2014, 9, 624-630.
Patra, et al., "Plasmofluidic Single-Molecule Surface-Enhanced Raman Scattering from Dynamic Assembly of Plasmonic Nanoparticles", Nat. Commun. 2014, 5, 4357.
Patra, et al., "Single-Molecule Surface-Enhanced Raman Scattering Sensitivity of Ag-Core Au-Shell Nanoparticles: Revealed by Bi-Analyte Method", J. Phys. Chem. Lett. 2013, 4, 1167-1171.
Pauzauskie, et al., "Optical trapping and integration of semiconductor nanowire assemblies in water", Nat. Mater. 2006, 5(2): 97-101.
Pelton, et al., "Optical trapping and alignment of single gold nanorods by using plasmon resonances", Opt. Lett. 31, 2075-2077 (2006).
Perry, et al., "Real-space studies of the structure and dynamics of self-assembled colloidal clusters", Faraday Discuss. 159, 211-234 (2012).
Perry, et al., "Two-Dimensional Clusters of Colloidal Spheres: Ground States, Excited States, and Structural Rearrangements", Phys. Rev. Lett. 114, 228301 (2015).
Piazza, et al., "Thermophoresis in colloidal suspensions", J. Phys.: Condens. Matter 20, 153102 (2008).
Pietryga, et al., "Spectroscopic and Device Aspects of Nanocrystal Quantum Dots", Chem Rev 2016, 116(18), 10513-10622.
Pignolet, et al., "Electrodeposition of latex particles in the presence of surfactant: Investigation of deposit morphology", J Colloid Interface Sci 2010, 349(1): 41-48.
Pinchuk, et al., "Size-dependent Hamaker constants for silver and gold nanoparticles", roc. SPIE 9549, Physical Chemistry of Interfaces and Nanomaterials XIV, 95491J, 2015, 95491J-95491J-95497.
Piner, et al., "Dip-Pen" Nanolithography, Science 1999, 283, 661-663.
Prieve, et al., "Simplified predictions of Hamaker constants from Lifshitz theory", J Colloid Interface Sci 1988, 125(1): 1-13.
Prikulis, et al., "Optical spectroscopy of single trapped metal nanoparticles in solution", Nano Lett. 4, 115-118 (2004).
Putnam, et al., "Temperature Dependence of Thermodiffusion in Aqueous Suspensions of Charged Nanoparticles", Langmuir 2007, 23, 9221-9228.
Rabani, et al., "Drying-mediated self-assembly of nanoparticles", Nature 2003, 426, 271-274.

(56) References Cited

OTHER PUBLICATIONS

Rajeeva, et al., "Regioselective Localization and Tracking of Biomolecules on Single Gold Nanoparticles", Adv Sci 2015, 2(11).
Raut, et al., "Multiscale ommatidial arrays with broadband and omnidirectional antireflection and antifogging properties by sacrificial layer mediated nanoimprinting", ACS Nano 2015, 9, 1305-1314.
Regmi, et al., "All-dielectric silicon nanogap antennas to enhance the fluorescence of single molecules", Nano Lett. 16, 5143-5151 (2016).
Reichl, et al., "Why charged molecules move across a temperature gradient: The role of electric fields", Phys. Rev. Lett. 112, 198101 (2014).
Righini, et al., "Parallel and selective trapping in a patterned plasmonic landscape", Nat Phys 2007, 3(7): 477-480.
Roelants, et al., "Parameters affecting aqueous micelles of CTAC, TTAC, and DTAC probed by fluorescence quenching", Langmuir 1987, 3(2): 209-214.
Roxworthy, et al., "Application of Plasmonic Bowtie Nanoantenna Arrays for Optical Trapping, Stacking, and Sorting", Nano Lett. 2012, 12, 796-801.
Roy, et al., "Self-Assembly of Mesoscopic Materials to Form Controlled and Continuous Patterns by Thermo-Optically Manipulated Laser Induced Microbubbles", Langmuir, 2013m 29(47), 14733-14742.
Ruijgrok, et al., "Brownian fluctuations and heating of an optically aligned gold nanorod", Phys. Rev. Lett. 107, 037401 (2011).
Rycenga, et al., "Controlling the synthesis and assembly of silver nanostructures for plasmonic applications", Chem. Rev. 2011, 111, 3669-3712.
Salaita, et al., "Nat. Applications of dip-pen nanolithography", Nanotechnol. 2007, 2, 145-155.
Sánchez-Iglesias, et al., "Hydrophobic interactions modulate self-assembly of nanoparticles", ACS Nano 6, 11059-11065 (2012).
Scarabelli, et al., "Monodisperse Gold Nanotriangles: Size Control, Large-Scale Self-Assembly, and Performance in Surface-Enhanced Raman Scattering", ACS Nano 2014, 8, 5833-5842.
Selhuber-Unkel, et al., "Quantitative optical trapping of single gold nanorods", Nano Lett. 8, 2998-3003 (2008).
Serra, et al., "Curvature-Driven, One-Step Assembly of Reconfigurable Smectic Liquid Crystal "Compound Eye" Lenses", Adv. Opt. Mater. 2015, 3, 1287-1292.
Shams Mousavi, et al., "Band-Edge Bilayer Plasmonic Nanostructure for Surface Enhanced Raman Spectroscopy", ACS Photonics 2015, 2, 1546-1551.
Shao, et al., "Gold nanorod rotary motors driven by resonant light scattering", ACS Nano 9, 12542-12551 (2015).
Shcherbatyuk, et al., "Anomalous photo-induced spectral changes in CdSe/ZnS quantum dots", J Appl Phys 2011, 110(5), 053518.
Si, et al., "Reversible Self-Assembly of Carboxylated Peptide-Functionalized Gold Nanoparticles Driven by Metal-Ion Coordination", ChemPhysChem 2008, 9, 1578-1584.
Srivastava, et al., "Light-controlled self-assembly of semiconductor nanoparticles into twisted ribbons", Science 327, 1355-1359 (2010).
Stamplecoskie, et al., "Optimal Size of Silver Nanoparticles for Surface-Enhanced Raman Spectroscopy", J. Phys. Chem. C 2011, 115, 1403-1409.
Stetciura, et al., "Composite SERS-Based Satellites Navigated by Optical Tweezers for Single Cell Analysis", Analyst 2015, 140, 4981-4986.
Stiles, et al., "Surface-Enhanced Raman Spectroscopy", Annu. Rev. Anal. Chem. 2008, 1, 601-626.
Streuli, et al., "Control of mammary epithelial differentiation: basement membrane induces tissue-specific gene expression in the absence of cell-cell interaction and morphological polarity", J. Cell Biol 115, 1383-1395 (1991).
Su, et al., "Reversible Voltage-Induced Assembly of Au Nanoparticles at Liquid|Liquid Interfaces", J. Am. Chem. Soc. 2004, 126, 915-919.

Sun, et al., "A haptic digital tool to assist the design, planning and manufacture of micro- and nanostructures", Proc Inst Mech Eng E J Process Mech Eng 2015, 229(4), 290-298.
Svedberg, et al., "Creating Hot Nanoparticle Pairs for Surface-Enhanced Raman Spectroscopy through Optical Manipulation", Nano Lett. 2006, 6, 2639-2641.
Taladriz-Blanco, et al., "Reversible Assembly of Metal Nanoparticles Induced by Penicillamine", Dynamic Formation of SERS Hot Spots. J. Mater. Chem. 2011, 21, 16880-16887.
Tanaka, et al., "Nanostructured potential of optical trapping using a plasmonic nanoblock pair", Nano Lett. 13, 2146-2150 (2013).
Tao, et al., "Tunable plasmonic lattices of silver nanocrystals", Nat. Nanotechnol. 2007, 2, 435-440.
Thamdrup, et al., "Light-Induced Local Heating for Thermophoretic Manipulation of DNA in Polymer Micro- and Nanochannels", Nano Lett. 10, 826-832 (2010).
Tong, et al., "Alignment, rotation, and spinning of single plasmonic nanoparticles and nanowires using polarization dependent optical forces", Nano Lett. 10, 268-273 (2010).
Tong, et al., "Optical Aggregation of Metal Nanoparticles in a Microfluidic Channel for Surface-Enhanced Raman Scattering Analysis", Lab Chip 2009, 9, 193-195.
Tong, et al., "Plasmon hybridization reveals the interaction between individual colloidal gold nanoparticles confined in an optical potential well", Nano Lett. 11, 4505-4508 (2011).
Tulpar, et al., "Decay Lengths of Double-Layer Forces in Solutions of Partly Associated Ions", Langmuir 2001, 17(26): 8451-8454.
Urban, et al., "Laser Printing Single Gold Nanoparticles", Nano Lett. 2010, 10, 4794-4798.
Vigolo, et al., "Thermophoresis and thermoelectricity in surfactant solutions", Langmuir 26, 7792-7801 (2010).
Wang, et al., "A general strategy for nanocrystal synthesis", Nature 2005, 437, 121-124.
Wang, et al., "Colloids with valence and specific directional bonding", Nature 491, 51-55 (2012).
Wang, et al., "Microfluidic Sorting of Mammalian Cells by Optical Force Switching", Nat. Biotechnol. 2005, 23, 83-87.
Wang, et al., "Nanosphere Arrays with Controlled Sub-10-Nm Gaps as Surface-Enhanced Raman Spectroscopy Substrates", J. Am. Chem. Soc. 2005, 127, 14992-14993.
Wang, et al., "Plasmonic trapping with a gold nanopillar", ChemPhysChem 2012, 13, 2639-2648.
Wang, et al., "Resonant light scattering from metal nanoparticles: Practical analysis beyond Rayleigh approximation", Appl Phys Lett, 2003, 83, 162-164.
Weinert, et al., "An Optical Conveyor for Molecules", Nano Lett. 2009, 9, 4264-4267.
Weinert, et al., "Observation of Slip Flow in Thermophoresis", Phys. Rev. Lett. 2008, 101, 168301.
Wiley, et al., "Synthesis of Silver Nanostructures with Controlled Shapes and Properties", Acc. Chem. Res. 2007, 40, 1067-1076.
Willets, et al., "Localized surface plasmon resonance spectroscopy and sensing", Annual Review of Physical Chemistry, vol. 58, 2007, pp. 267-297.
Wilson, et al., "Scalable nano-particle assembly by efficient light-induced concentration and fusion", Opt. Express 2008, 16(22), 17276-17281.
Wood, et al., "Single cell trapping and DNA damage analysis using microwell arrays", Proc. Natl. Acad. Sci. 2010, 107, 10008-10013.
Wu, et al., "Bioinspired fabrication of high-quality 3D artificial compound eyes by voxel-modulation femtosecond laser writing for distortion-free wide-field-of-view imaging", Adv. Opt. Mater. 2014, 2, 751-758.
Wu, MC, "Optoelectronic tweezers", Nat. Photonics 2011, 5(6): 322-324.
Würger, A, "Hydrodynamic Boundary Effects on Thermophoresis of Confined Colloids", Phys. Rev. Lett. 2016, 116, 138302.
Würger, A, "Thermophoresis in Colloidal Suspensions Driven by Marangoni Forces", Phys. Rev. Lett. 2007, 98(13): 138301.
Würger, A, "Transport in Charged Colloids Driven by Thermoelectricity", Phys. Rev. Lett. 2008, 101, 108302.
Würger, A., "Thermal Non-Equilibrium Transport in Colloids", Rep. Prog. Phys. 2010, 73, 126601.

(56) References Cited

OTHER PUBLICATIONS

Xia, et al., "One-dimensional nanostructures: synthesis, characterization, and applications", Adv. Mater. 2003, 15, 353-389.
Xia, et al., "Template-assisted self-assembly of spherical colloids into complex and controllable structures", Adv. Funct. Mater. 2003, 13, 907-918.
Xie, et al., "Nanoscale and Single-Dot Patterning of Colloidal Quantum Dots", Nano Lett 2015, 15(11), 7481-7487.
Xie, et al., "Optoacoustic Tweezers: a Programmable, Localized Cell Concentrator Based on Opto-Thermally Generated, Acoustically Activated, Surface Bubbles", Lab Chip 2013, 13, 1772-1779.
Yan, et al., "Colloidal superstructures programmed into magnetic janus particles", Adv. Mater. 27, 874-879 (2015).
Yan, et al., "Controlling the position and orientation of single silver nanowires on a surface using structured optical fields", ACS Nano 6, 8144-8155 (2012).
Yan, et al., "Fabrication of a Material Assembly of Silver Nanoparticles Using the Phase Gradients of Optical Tweezers", Phys. Rev. Lett. 114, 143901 (2015).
Yan, et al., "Reconfiguring active particles by electrostatic imbalance", Nature Mater. 15, 1095-1099 (2016).
Yan, et al., "Thermal conductivity of monolayer molybdenum disulfide obtained from tempearture-dependent raman spectroscopy", ACS Nano 2014, 8, 986-993.
Yan, et al., "Why single-beam optical tweezers trap gold nanowires in three dimensions", ACS Nano 7, 8794-8800 (2013).
Yang, et al., "Breakthroughs in Photonics 2014: Advances in Plasmonic Nanolasers", IEEE Photonics J 2015, 7(3).
Ye, et al., "Plasmonic Nanoclusters: Near Field Properties of the Fano Resonance Interrogated with SERS", Nano Lett. 2012, 12, 1660-1667.
Yeom, et al., "Chiral templating of self-assembling nanostructures by circularly polarized light", Nature Mater. 14, 66-72 (2015).
Yin, et al., "The chemistry of functional nanomaterials", Chem Soc Rev 2013, 42(7), 2484-2487.
Yoshikawa, et al., "Reversible Assembly of Gold Nanoparticles Confined in an Optical Microcage", Phys. Rev. E 2004, 70, 061406.
Yu, et al., "Experimental determination of the extinction coefficient of CdTe, CdSe and CdS nanocrystals", Chem Mater 2003, 15: 2854-2860.
Yu, et al., "Experimental Determination of the Extinction Coefficient of CdTe, CdSe, and CdS nanocrystals", Chem Mater 2004, 16, 560.
Yu, et al., "Formation of high-quality CdS and other II-VI semiconductor nanocrystals in noncoordinating solvents: Tunable reactivity of monomers", Angew Chem Int Edit 2002, 41(13), 2368-2371.
Yu, et al., "Forming biocompatible and non-aggregated nanocrystals in water using amphiphilic polymers", J Am Chem Soc 2007, 129: 2871-2879.
Zerrouki, et al., "Chiral colloidal clusters", Nature 455, 380-382 (2008).
Zhang, et al., "Directed self-assembly pathways of active colloidal clusters", Angew. Chem. Int. Ed. 55, 5166-5169 (2016).
Zhang, et al., "Living Cell Multilifetime Encoding Based on Lifetime-Tunable Lattice-Strained Quantum Dots", ACS Appl Mater Inter 2016, 8(21), 13187-13191.
Zhang, et al., "Toward design rules of directional janus colloidal assembly", Annu. Rev. Phys. Chem. 66, 581-600 (2015).
Zhang, et al., "Trapping and sensing 10 nm metal nanoparticles using plasmonic dipole antennas", Nano Lett. 10, 1006-1011 (2010).
Zhao, et al., "Theory and experiment on particle trapping and manipulation via optothermally generated bubbles", Lab Chip 2014, 14, 384-391.
Zh Eng, et al., "Nano-Optical Conveyor Belt, Part II: Demonstration of Handoff Between Near-Field Optical Traps.", Nano Lett. 14, 2971-2976 (2014).
Zhong, "Trapping Red Blood Cells in Living Animals Using Optical Tweezers", Nat. Commun. 2013, 4, 1768.
IPRP dated Jun. 28, 2018 in related PCT application PCT/US16/066291.
PCT Search Report & Written Opinion for PCT/US16/66291 dated Mar. 2, 2017.
PCT Search Report & Written Opinion for PCT/US2017/028379 dated Jul. 14, 2017.
International Search Report and Written Opinion for PCT/US2017/050605.

* cited by examiner

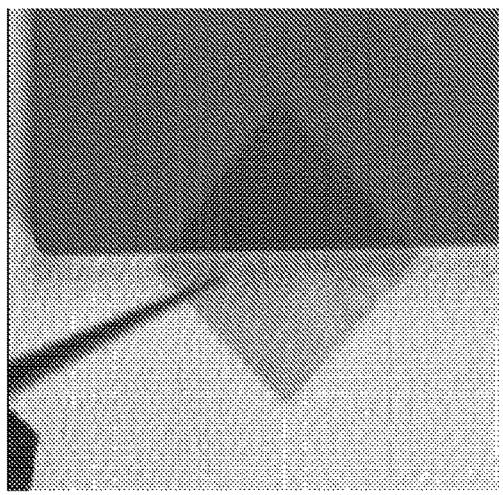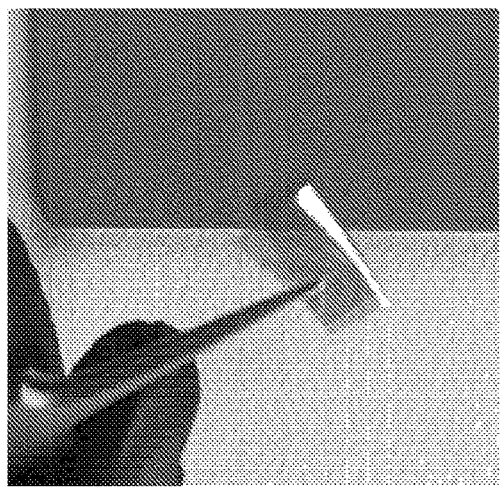
FIG. 85
FIG. 86
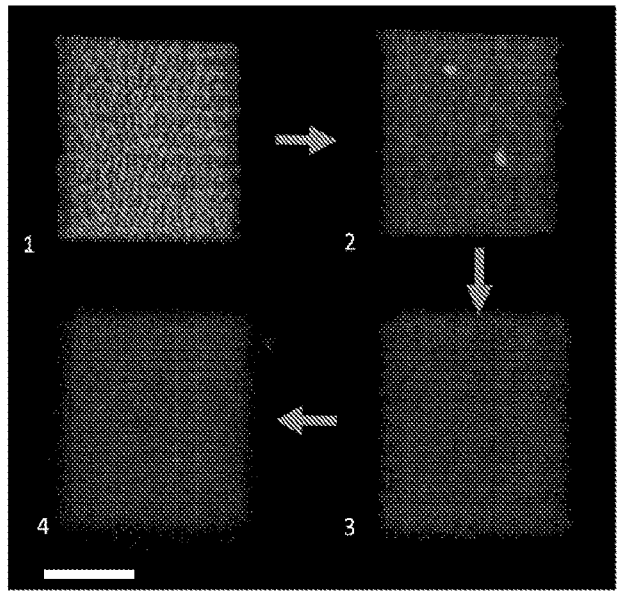
FIG. 87

LITHOGRAPHIC SYSTEMS AND METHODS

CROSS-REFERENCE TO RELATED APPLICATIONS

This application claims the benefit of U.S. Provisional Application No. 62/266,829, filed Dec. 14, 2015, which is hereby incorporated herein by reference in its entirety.

BACKGROUND

Lithography and chemical synthesis are two strategies for nanofabrication. Photolithography has remained the standard in the semiconductor industry, but its resolution can be limited. Electron beam (E-beam) lithography and ion-beam lithography feature high resolution and arbitrary patterning, however, they are limited by high cost and low throughput. Chemical synthesis has advantages in both low cost and precise control of compositions, sizes and shapes of nanomaterials. With their precisely tailorable properties down to the atomic level, colloidal micro-/nano-particles are promising as building blocks for functional devices. However, the device applications often require the patterning of particles on solid-state substrates. For this purpose, a wide range of techniques have been developed, including self-assembly, Langmuir-Blodgett (LB) method, dip-pen nanolithography, polymer pen lithography and contact-printing. Optical tweezers have been proved effective in manipulating the colloidal micro-/nano-particles in solutions (Grier D G. *Nature* 2003, 424, 810-816; Pauzauskie P J et al. *Nat. Mater.* 2006, 5, 97-101; Selhuber-Unkel C et al. *Nano Lett.* 2008, 8, 2998-3003). Despite its capability of offering remote, real-time and versatile manipulations of colloidal particles, conventional optical tweezers require high laser power (100 mW/μm$^2$) that can damage the colloidal particles and immobilizing the particles onto the substrates has remained challenging. There remains a need for new light-based techniques that can create the arbitrary patterns of colloidal particles immobilized on the substrates. The systems and methods discussed herein address these and other needs.

SUMMARY

Disclosed herein are methods comprising illuminating a first location of a plasmonic substrate with electromagnetic radiation, wherein the electromagnetic radiation comprises a wavelength that overlaps with at least a portion of the plasmon resonance energy of the plasmonic substrate. In some examples, the power density of the electromagnetic radiation can be 10 mW/μm$^2$ or less (e.g., 5 mW/μm$^2$ or less, 1.5 mW/μm$^2$ or less).

The electromagnetic radiation can, for example, be provided by a light source. In some examples, the light source is an artificial light source. In some examples, the light source is a laser.

The plasmonic substrate can, in some examples, comprise a plurality of plasmonic particles. In some examples, the plurality of plasmonic particles can comprise a plurality of metal particles. The plurality of metal particles can, for example, comprise a metal selected from the group consisting of Au, Ag, Pt, Pd, Cu, Al, and combinations thereof. In some examples, the plurality of plasmonic particles can comprise a plurality of gold particles. The plurality of plasmonic particles can have an average particle size of from 10 nm to 300 nm. In some examples, the plurality of plasmonic particles have an average particle size of from 20 nm to 40 nm. In some examples, the plurality of plasmonic particles are substantially spherical.

In some examples, each plasmonic particle within the plurality of plasmonic particles on the substrate is separated from its neighboring plasmonic particles by an average distance of from 5 nm to 100 nm. In some examples, each plasmonic within the plurality of plasmonic particles on the substrate is separated from its neighboring plasmonic particles by an average distance of from 5 nm to 10 nm. The density of the plurality of plasmonic particles on the plasmonic substrate can, for example, be $10^{11}$ particles/cm$^2$ or less.

The methods can further comprise, for example, making the plasmonic substrate by depositing the plurality of plasmonic particles on a substrate. Depositing the plurality of plasmonic particles can comprise, for example, printing, lithographic deposition, electron beam deposition, thermal deposition, spin coating, drop-casting, zone casting, dip coating, blade coating, spraying, vacuum filtration, or combinations thereof.

The methods can further comprise, for example, making the plasmonic substrate by thermally annealing a film of a plasmonic metal deposited on a substrate, thereby forming the plurality of plasmonic particles on the substrate. In some examples, the methods can further comprise depositing the film of the plasmonic metal on the substrate. In some examples, the film of the plasmonic metal has a thickness of from 2 nm to 15 nm. In some examples, the films of the plasmonic metal has a thickness of from 4 nm to 10 nm. Thermally annealing the film can, for example, comprise heating the film at a temperature of from 400° C. to 600° C. (e.g., 550° C.). In some examples, the film can be thermally annealed for from 1 to 12 hours (e.g., 2 hours).

The plasmonic substrate can be, for example, in thermal contact with a liquid sample comprising a plurality of particles. The liquid sample can further comprise, for example, an aqueous solvent. The concentration of the plurality of particles in the liquid sample can, for example, be from $10^3$ particles/mm$^3$ to $10^{10}$ particles/mm$^3$. The plurality of particles in the liquid sample can have, for example, an average particle size of from 4 nm to 20 μm.

In some examples, the plurality of particles in the liquid sample can comprise a plurality of thermoresponsive particles. Examples of thermoresponsive particles include, for example, polymer particles (e.g., polystyrene particles), polymer capped metal particles, or combinations thereof. In some examples, the plurality of particles in the liquid sample can comprise a plurality of polymer capped metal particles, such as a plurality of plasmonic particles, a plurality of quantum dots (e.g., comprising CdSe, ZnS, or combinations thereof), or combinations thereof. In some examples, the plurality of particles in the liquid sample can comprise a plurality of polystyrene particles having an average particle size of from 60 nm to 10 μm. In some examples, the plurality of particles can comprise, a plurality of polystyrene spheres, a plurality of silica spheres, a plurality of quantum dots, a plurality of semiconductor nanowires, a plurality of biological cells (e.g., *E. coli*, yeast), or a combination thereof.

The methods can further comprise, for example, generating a bubble at a location in the liquid sample proximate to the first location of the plasmonic substrate, the bubble having a gas-liquid interface with the liquid sample. In some examples, the bubble is generated by plasmon-enhanced photothermal effects. The bubble can have a diameter of from 100 nm to 50 μm (e.g., from 500 nm to 50 μm, from 100 nm to 25 μm, from 100 nm to 10 μm, from 100 nm to 5 μm, or from 100 nm to 1 μm).

The methods can further comprise, for example, trapping at least a portion of the plurality of particles at the gas-liquid interface of the bubble and the liquid sample. The portion of the plurality of particles at the gas-liquid interface, for example, by convection, surface tension, gas pressure, substrate adhesion, or combinations thereof. In some examples, convection can comprise natural convection, Maragoni convection, or combinations thereof. The portion of the plurality of particles can be trapped, for example, at a trapping speed of from 10 μm/s to 1000 μm/s. In some examples, the portion of the plurality of particles are trapped at a trapping speed of from 15 μm/s to 35 μm/s.

The methods can further comprise, for example, depositing at least a portion of the plurality of particles on the plasmonic substrate at the first location. In some examples, the portion of the plurality of particles are not damaged during the deposition. In some examples, the portion of the plurality of particles deposited is one particle. In other words, also disclosed herein are methods for single-particle patterning.

In some examples, the portion of the plurality of particles is deposited in an amount of time from 1 milliseconds (ms) to 5 seconds (s). For example, the portion of the plurality of particles can be deposited in 2 seconds or less.

In some examples, the portion of the plurality of particles deposited on the substrate are immobilized on the plasmonic substrate by surface adhesion. In some examples, the plasmonic substrate can further comprise a ligand and the portion of the plurality of particles deposited on the substrate are immobilized on the plasmonic substrate by electrostatic attraction and/or chemical recognition with the ligand (e.g., surface functionalization of the plasmonic substrate for particle immobilization).

In some examples, an additional layer is present between the plasmonic substrate and the liquid sample, the additional layer being in thermal contact with the plasmonic substrate and the liquid sample, such that the plurality of particles are deposited on the additional layer. The additional layer can, for example, comprise a two-dimensional atomic layer material, such as $MoS_2$, $WSe_2$, $MoTe_2$, $WS_2$, hexagonal BN, graphene, or combinations thereof.

The methods can further comprise, for example, illuminating a second location of the plasmonic substrate to deposit another portion of the plurality of particles at the second location. In some examples, the plasmonic substrate and/or the light source can be translocated to illuminate the second location.

Also disclosed herein are patterned substrate made using the methods described herein. Also disclosed herein are methods of use of patterned substrates made using the methods described herein, for example using the patterned substrates for single-particle sensing, single-cell analysis, tissue engineering, functional optical devices, or combinations thereof.

Also disclosed herein are systems for performing the methods described herein. The systems 100 can comprise a plasmonic substrate 102 in thermal contact with a liquid sample 104 comprising a plurality of particles 106; and a light source 108 configured to illuminate the plasmonic substrate at a first location 110. In some examples, the system 100 can include a single light source 108. In other examples, more than one light source 108 can be included in the system 100. In some examples, the systems can further comprise a means for translocating the plasmonic substrate and/or the light source. The systems 110 can, in some examples, further comprise an instrument 112 configured to capture an electromagnetic signal from the plasmonic substrate 102. In some examples, the system 110 can further comprise a first lens 114. In some examples, the system 110 can further comprise a second lens 116. In some examples, the system 110 can be configured such that the light source 108 is below the first lens 114 and the plasmonic substrate 102 is above the first lens 114. In some examples, the system 110 is aligned such that the light source 108 is below the first lens 114, the plasmonic substrate 102 is above the first lens 114, the second lens 116 is above the plasmonic substrate 102, and the instrument 112 is above the second lens 116.

In some example, the systems 110 can further comprise a computing device 118 configured to receive and process electromagnetic signals from the instrument 112. In certain examples, system memory 122 comprises computer-executable instructions stored thereon that, when executed by the processor 120, cause the processor 120 to receive an electromagnetic signal from the instrument 112, process the electromagnetic signal to obtain a characteristic of the plasmonic substrate 102; and output the characteristic of the plasmonic substrate 102.

The instrument can comprise, for example, a camera, an optical microscope, an electron microscope, a spectrometer, or combinations thereof. Examples of spectrometers include, but are not limited to, Raman spectrometers, UV-vis absorption spectrometers, IR absorption spectrometers, fluorescence spectrometers, and combinations thereof.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects of the disclosure, and together with the description, serve to explain the principles of the disclosure.

FIG. 85 is an image of the Au coated PET film in the relaxed state.

FIG. 86 is an image of the Au coated PET film under bent state.

FIG. 87 shows the fabrication of squares with emission modification of yellow QDs dependent on the printing parameters. The printing parameters within the merged fluorescence image are (i) Square 1: 0.52 mW/µm², stage speed 1000 µm/s, wait time 500 ms, line-spacing 1 µm (ii) Square 2: 0.54 mW/µm², stage speed 500 µm/s, wait time 600 ms, line-spacing 1 µm (iii) Square 3: 0.56 mW/µm², stage speed 100 µm/s, wait time 800 ms, and line-space 1 µm (iv) Square 4: 0.58 mW/µm², stage speed 100 µm/s, wait time 1 s, and line space 0.5 µm. Scale bar: 10 µm.

DETAILED DESCRIPTION

Figure 1:
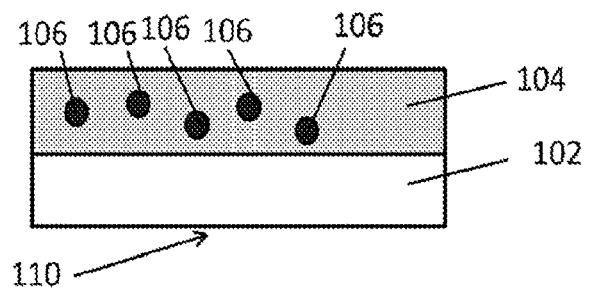
FIG. 1 is a schematic of an exemplary system as disclosed herein for lithography.
Figure 1:
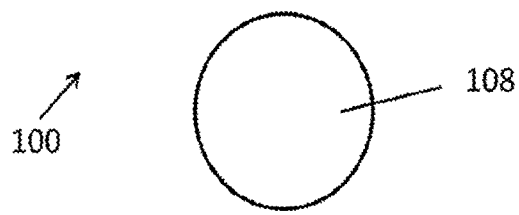

The systems and methods described herein may be understood more readily by reference to the following detailed description of specific aspects of the disclosed subject matter and the Examples included therein.

Before the present systems and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value.

By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Disclosed herein are lithographic systems and methods, for example for patterning colloidal particles on substrates using optically controlled bubbles. In some examples, the methods and systems can comprise locally exposing the substrate to an optical signal according to a desired pattern to thereby pattern the substrate.

Disclosed herein are methods comprising illuminating a first location of a plasmonic substrate with electromagnetic radiation, wherein the electromagnetic radiation comprises a wavelength that overlaps with at least a portion of the plasmon resonance energy of the plasmonic substrate. As used herein, "a first location" and "the first location" are meant to include any number of locations in any arrangement on the plasmonic substrate. Thus, for example "a first location" includes one or more first locations. In some embodiments, the first location can comprise a plurality of locations. In some embodiments, the first locations can comprise a plurality of locations arranged in an ordered array.

In some examples, the power density of the electromagnetic radiation can be 10 mW/$\mu$m$^2$ or less (e.g., 9 mW/$\mu$m$^2$ or less, 8 mW/$\mu$m$^2$ or less, 7 mW/$\mu$m$^2$ or less, 6 mW/$\mu$m$^2$ or less, 5 mW/$\mu$m$^2$ or less, 4.5 mW/$\mu$m$^2$ or less, 4 mW/$\mu$m$^2$ or less, 3.5 mW/$\mu$m$^2$ or less, 3 mW/$\mu$m$^2$ or less, 2.5 mW/$\mu$m$^2$ or less, 2 mW/$\mu$m$^2$ or less, 1.5 mW/$\mu$m$^2$ or less, 1 mW/$\mu$m$^2$ or less, or 0.5 mW/$\mu$m$^2$ or less). In some examples, the power density of the electromagnetic radiation can be 0.1 mW/$\mu$m$^2$ or more (e.g., 0.5 mW/$\mu$m$^2$ or more, 1 mW/$\mu$m$^2$ or more, 1.5 mW/$\mu$m$^2$ or more, 2 mW/$\mu$m$^2$ or more, 2.5 mW/$\mu$m$^2$ or more, 3 mW/$\mu$m$^2$ or more, 3.5 mW/$\mu$m$^2$ or more, 4 mW/$\mu$m$^2$ or more, 4.5 mW/$\mu$m$^2$ or more, 5 mW/$\mu$m$^2$ or more, 5.5 mW/$\mu$m$^2$ or more, 6 mW/$\mu$m$^2$ or more, 6.5 mW/$\mu$m$^2$ or more, 7 mW/$\mu$m$^2$ or more, 8 mW/$\mu$m$^2$ or more, or 9 mW/$\mu$m$^2$ or more). The power density of the electromagnetic radiation can range from any of the minimum values described above to any of the maximum values described above. For example, the power density of the electromagnetic radiation can range from 0.1 mW/$\mu$m$^2$ to 10 mW/$\mu$m$^2$ (e.g., from 0.1 mW/$\mu$m$^2$ to 5 mW/$\mu$m$^2$, from 5 mW/$\mu$m$^2$ to 10 mW/$\mu$m$^2$, from 0.1 mW/$\mu$m$^2$ to 2 mW/$\mu$m$^2$, from 2 mW/$\mu$m$^2$ to 4 mW/$\mu$m$^2$, from 4 mW/$\mu$m$^2$ to 6 mW/$\mu$m$^2$, from 6 mW/$\mu$m$^2$ to 8 mW/$\mu$m$^2$, form 8 mW/$\mu$m$^2$ to 10 mW/$\mu$m$^2$, or from 0.5 mW/$\mu$m$^2$ to 5 mW/$\mu$m$^2$).

The electromagnetic radiation can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers etc.). In some examples, the light source is a laser.

The plasmonic substrate can, in some examples, comprise a plurality of plasmonic particles. In some examples, the plurality of plasmonic particles can comprise a plurality of metal particles. The plurality of metal particles can, for example, comprise a metal selected from the group consisting of Au, Ag, Pd, Cu, Cr, Al, and combinations thereof. In some examples, the plurality of plasmonic particles can comprise a plurality of gold particles.

The plurality of plasmonic particles can have an average particle size. "Average particle size," "mean particle size," and "median particle size" are used interchangeably herein, and generally refer to the statistical mean particle size of the particles in a population of particles. For example, the average particle size for a plurality of particles with a substantially spherical shape can comprise the average diameter of the plurality of particles. For a particle with a substantially spherical shape, the diameter of a particle can refer, for example, to the hydrodynamic diameter. As used herein, the hydrodynamic diameter of a particle can refer to the largest linear distance between two points on the surface of the particle. Mean particle size can be measured using methods known in the art, such as evaluation by scanning electron microscopy, transmission electron microscopy, and/or dynamic light scattering.

The plurality of plasmonic particles have, for example, an average particle size of 10 nm or more (e.g., 15 nm or more, 20 nm or more, 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 160 nm or more, 170 nm or more, 180 nm or more, 190 nm or more, 200 nm or more, 210 nm or more, 220 nm or more, 230 nm or more, 240 nm or more, 250 nm or more, 260 nm or more, 270 nm or more, 280 nm or more, or 290 nm or more).

In some examples, the plurality of plasmonic particles can have an average particle size of 300 nm or less (e.g., 290 nm or less, 280 nm or less, 270 nm or less, 260 nm or less, 250 nm or less, 240 nm or less, 230 nm or less, 220 nm or less, 210 nm or less, 200 nm or less, 190 nm or less, 180 nm or less, 170 nm or less, 160 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, or 15 nm or less).

The average particle size of the plurality of plasmonic particles can range from any of the minimum values described above to any of the maximum values described above. For example, the plurality of plasmonic particles can have an average particle size of from 10 nm to 300 nm (e.g., from 10 nm to 150 nm, from 150 nm to 300 nm, from 10 nm to 100 nm, from 100 nm to 200 nm, from 200 nm to 300 nm, or from 10 nm to 200 nm). In some examples, the plurality of plasmonic particles have an average particle size of from 20 nm to 40 nm.

In some examples, the plurality of plasmonic particles can be substantially monodisperse. "Monodisperse" and "homogeneous size distribution," as used herein, and generally describe a population of particles where all of the particles are the same or nearly the same size. As used herein, a monodisperse distribution refers to particle distributions in which 80% of the distribution (e.g., 85% of the distribution, 90% of the distribution, or 95% of the distribution) lies within 25% of the median particle size (e.g., within 20% of the median particle size, within 15% of the median particle size, within 10% of the median particle size, or within 5% of the median particle size).

The plurality of plasmonic particles can comprise particles of any shape (e.g., a sphere, a rod, a quadrilateral, an ellipse, a triangle, a polygon, etc.). In some examples, the plurality of plasmonic particles can have an isotropic shape. In some examples, the plurality of plasmonic particles can have an anisotropic shape. In some examples, the plurality of plasmonic particles are substantially spherical.

In some examples, each plasmonic particle within the plurality of plasmonic particles on the substrate is separated from its neighboring plasmonic particles by an average distance of 5 nm or more (e.g., 6 nm or more, 7 nm or more, 8 nm or more, 9 nm or more, 10 nm or more, 11 nm or more, 12 nm or more, 13 nm or more, 14 nm or more, 15 nm or more, 16 nm or more, 17 nm or more, 18 nm or more, 19 nm or more, 20 nm or more, 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, 90 nm or more, or 95 nm or more).

In some examples, each plasmonic particle within the plurality of plasmonic particles on the substrate is separated from its neighboring plasmonic particles by an average distance of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 19 nm or less, 18 nm or less, 17 nm or less, 16 nm or less, 15 nm or less, 14 nm or less, 13 nm or less, 12 nm or less, 11 nm or less, 10 nm or less, 9 nm or less, 8 nm or less, 7 nm or less, or 6 nm or less).

The average distance that each plasmonic particle within the plurality of plasmonic particles on the substrate is separated from its neighboring plasmonic particles can range from any of the minimum values described above to any of the maximum values described above. For example, each plasmonic particle within the plurality of plasmonic particles on the substrate is separated from its neighboring plasmonic particles by an average distance of from 5 nm to 100 nm (e.g., from 5 nm to 50 nm, from 50 nm to 100 nm, from 5 nm to 20 nm, from 20 nm to 40 nm, from 40 nm to 60 nm, from 60 nm to 80 nm, from 80 nm to 100 nm, from 5 nm to 40 nm, from 5 nm to 30 nm, from 5 nm to 15 nm, or from 5 nm to 10 nm).

The density of the plurality of plasmonic particles on the plasmonic substrate can, for example, be $10^{10}$ particles/cm$^2$ or more (e.g., $1.25 \times 10^{10}$ particles/cm$^2$ or more, $1.5 \times 10^{10}$ particles/cm$^2$ or more, $1.75 \times 10^{10}$ particles/cm$^2$ or more, $2 \times 10^{10}$ particles/cm$^2$ or more, $2.25 \times 10^{10}$ particles/cm$^2$ or more, $2.5 \times 10^{10}$ particles/cm$^2$ or more, $2.75 \times 10^{10}$ particles/cm$^2$ or more, $3 \times 10^{10}$ particles/cm$^2$ or more, $3.25 \times 10^{10}$ particles/cm$^2$ or more, $3.5 \times 10^{10}$ particles/cm$^2$ or more, $3.75 \times 10^{10}$ particles/cm$^2$ or more, $4 \times 10^{10}$ particles/cm$^2$ or more, $4.25 \times 10^{10}$ particles/cm$^2$ or more, $4.5 \times 10^{10}$ particles/cm$^2$ or more, $4.75 \times 10^{10}$ particles/cm$^2$ or more, $5 \times 10^{10}$ particles/cm$^2$ or more, $5.25 \times 10^{10}$ particles/cm$^2$ or more, $5.5 \times 10^{10}$ particles/cm$^2$ or more, $5.75 \times 10^{10}$ particles/cm$^2$ or more, $6 \times 10^{10}$ particles/cm$^2$ or more, $6.25 \times 10^{10}$ particles/cm$^2$ or more, $6.5 \times 10^{10}$ particles/cm$^2$ or more, $6.75 \times 10^{10}$ particles/cm$^2$ or more, $7 \times 10^{10}$ particles/cm$^2$ or more, $7.25 \times 10^{10}$ particles/cm$^2$ or more, $7.5 \times 10^{10}$ particles/cm$^2$ or more, $7.75 \times 10^{10}$ particles/cm$^2$ or more, $8 \times 10^{10}$ particles/cm$^2$ or more, $8.25 \times 10^{10}$ particles/cm$^2$ or more, $8.5 \times 10^{10}$ particles/cm$^2$ or more, $8.75 \times 10^{10}$ particles/cm$^2$ or more, $9 \times 10^{10}$ particles/cm$^2$ or more, $9.25 \times 10^{10}$ particles/cm$^2$ or more, $9.5 \times 10^{10}$ particles/cm$^2$ or more, or $9.75 \times 10^{10}$ particles/cm$^2$ or more).

In some examples, the density of the plurality of plasmonic particles on the plasmonic substrate can be $10^{11}$ particles/cm$^2$ or less (e.g., $9.75 \times 10^{10}$ particles/cm$^2$ or less, $9.5 \times 10^{10}$ particles/cm$^2$ or less, $9.25 \times 10^{10}$ particles/cm$^2$ or less, $9 \times 10^{10}$ particles/cm$^2$ or less, $8.75 \times 10^{10}$ particles/cm$^2$ or less, $8.5 \times 10^{10}$ particles/cm$^2$ or less, $8.25 \times 10^{10}$ particles/cm$^2$ or less, $8 \times 10^{10}$ particles/cm$^2$ or less, $7.75 \times 10^{10}$ particles/cm$^2$ or less, $7.5 \times 10^{10}$ particles/cm$^2$ or less, $7.25 \times 10^{10}$ particles/cm$^2$ or less, $7 \times 10^{10}$ particles/cm$^2$ or less, $6.75 \times 10^{10}$ particles/cm$^2$ or less, $6.5 \times 10^{10}$ particles/cm$^2$ or less, $6.25 \times 10^{10}$ particles/cm$^2$ or less, $6 \times 10^{10}$ particles/cm$^2$ or less, $5.75 \times 10^{10}$ particles/cm$^2$ or less, $5.5 \times 10^{10}$ particles/cm$^2$ or less, $5.25 \times 10^{10}$ particles/cm$^2$ or less, $5 \times 10^{10}$ particles/cm$^2$ or less, $4.75 \times 10^{10}$ particles/cm$^2$ or less, $4.5 \times 10^{10}$ particles/cm$^2$ or less, $4.25 \times 10^{10}$ particles/cm$^2$ or less, $4 \times 10^{10}$ particles/cm$^2$ or less, $3.75 \times 10^{10}$ particles/cm$^2$ or less, $3.5 \times 10^{10}$ particles/cm$^2$ or less, $3.25 \times 10^{10}$ particles/cm$^2$ or less, $3 \times 10^{10}$ particles/cm$^2$ or less, $2.75 \times 10^{10}$ particles/cm$^2$ or less, $2.5 \times 10^{10}$ particles/cm$^2$ or less, $2.25 \times 10^{10}$ particles/cm$^2$ or less, $2 \times 10^{10}$ particles/cm$^2$ or less, $1.75 \times 10^{10}$ particles/cm$^2$ or less, $1.5 \times 10^{10}$ particles/cm$^2$ or less, or $1.25 \times 10^{10}$ particles/cm$^2$ or less).

The density of the plurality of plasmonic particles on the plasmonic substrate can range from any of the minimum values described above to any of the maximum values described above. For example, the density of the plurality of plasmonic particles on the plasmonic substrate can be from $10^{10}$ particles/cm$^2$ to $10^{11}$ particles/cm$^2$ (e.g., from $1 \times 10^{10}$ particles/cm$^2$ to $5 \times 10^{10}$ particles/cm$^2$, from $5 \times 10^{10}$ particles/cm$^2$ to $1 \times 10^{11}$ particles/cm$^2$, from $1 \times 10^{10}$ particles/cm$^2$ to $2.5 \times 10^{10}$ particles/cm$^2$, from $2.5 \times 10^{10}$ particles/cm$^2$ to $5 \times 10^{10}$ particles/cm$^2$, from $5 \times 10^{10}$ particles/cm$^2$ to $7.5 \times 10^{10}$ particles/cm$^2$, from $7.5 \times 10^{10}$ particles/cm$^2$ to $1 \times 10^{11}$ particles/cm$^2$, or from $2 \times 10^{10}$ particles/cm$^2$ to $9 \times 10^{10}$ particles/cm$^2$).

The size, shape, and/or composition of the plurality of plasmonic particles; the separation between each particle within the plurality of plasmonic particles; the density of the plasmonic particles on the substrate; or combinations thereof can be selected in view of a variety of factors. In some examples, the size, shape, and/or composition of the plurality of plasmonic particles can be selected to maximize the electromagnetic field enhancement. For example, the size, shape, and/or composition of the plurality of plasmonic particles; the separation between each particle within the plurality of plasmonic particles; the density of the plasmonic particles on the substrate; or combinations thereof can be selected such that the intensity of an incident electromagnetic field is enhanced by a factor of 5 or more by the plurality of plasmonic particles (e.g., 10 or more, 20 or more, 30 or more, 40 or more, 50 or more, 60 or more 70 or more, 80 or more, 90 or more, or 100 or more). In some examples, the size, shape, and/or composition of the plurality of plasmonic particles; the separation between each particle within the plurality of plasmonic particles; the density of the plasmonic particles on the substrate; or combinations thereof can be selected such that the plasmon resonance energy of the plasmonic substrate overlaps with at least a portion of the electromagnetic radiation used to illuminate the plasmonic substrate.

The methods can further comprise, for example, making the plasmonic substrate by depositing the plurality of plasmonic particles on a substrate. Depositing the plurality of plasmonic particles can comprise, for example, printing, lithographic deposition, electron beam deposition, thermal deposition, spin coating, drop-casting, zone casting, dip coating, blade coating, spraying, vacuum filtration, or combinations thereof.

The methods can further comprise, for example, making the plasmonic substrate by thermally annealing a film of a plasmonic metal deposited on a substrate, thereby forming the plurality of plasmonic particles on the substrate. In some examples, the methods can further comprise depositing the film of the plasmonic metal on the substrate. The film of plasmonic metal can be deposited on the substrate, for example, by thin film processing techniques, such as sputtering, pulsed layer deposition, molecular beam epitaxy, evaporation, atomic layer deposition, or combinations thereof. In some examples, the film of the plasmonic metal can have a thickness of 2 nm or more (e.g., 2.5 nm or more, 3 nm or more, 3.5 nm or more, 4 nm or more, 4.5 nm or more, 5 nm or more, 5.5 nm or more, 6 nm or more, 6.5 nm or more, 7 nm or more, 7.5 nm or more, 8 nm or more, 8.5 nm or more, 9 nm or more, 9.5 nm or more, 10 nm or more, 10.5 nm or more, 11 nm or more, 11.5 nm or more, 12 nm or more, 12.5 nm or more, 13 nm or more, 13.5 nm or more, 14 nm or more, or 14.5 nm or more). In some examples, the film of the plasmonic metal can have a thickness of 15 nm or less (e.g., 14.5 nm or less, 14 nm or less, 13.5 nm or less, 13 nm or less, 12.5 nm or less, 12 nm or less, 11.5 nm or less, 11 nm or less, 10.5 nm or less, 10 nm or less, 9.5 nm or less, 9 nm or less, 8.5 nm or less, 8 nm or less, 7.5 nm or less, 7 nm or less, 6.5 nm or less, 6 nm or less, 5.5 nm or less, 5 nm or less, 4.5 nm or less, 4 nm or less, 3.5 nm or less, 3 nm or less, or 2.5 nm or less). The thickness of the film of the plasmonic metal can range from any of the minimum values described above to any of the maximum values described above. For example, the film of the plasmonic metal can have a thickness of from 2 nm to 15 nm (e.g., from 2 nm to 8 nm, from 8 nm to 15 nm, from 2 nm to 5 nm, from 5 nm to 10 nm, from 10 nm to 15 nm, or from 4 nm to 10 nm).

Thermally annealing the film can, for example, comprise heating the film at a temperature of 400° C. or more (e.g., 410° C. or more, 420° C. or more, 430° C. or more, 440° C. or more, 450° C. or more, 460° C. or more, 470° C. or more, 480° C. or more, 490° C. or more, 500° C. or more, 510° C. or more, 520° C. or more, 530° C. or more, 540° C. or more, 550° C. or more, 560° C. or more, 570° C. or more, 580° C. or more, or 590° C. or more). In some examples, thermally annealing the film can comprise heating the film at a temperature of 600° C. or less (e.g., 590° C. or less, 580° C. or less, 570° C. or less, 560° C. or less, 550° C. or less, 540° C. or less, 530° C. or less, 520° C. or less, 510° C. or less, 500° C. or less, 490° C. or less, 480° C. or less, 470° C. or less, 460° C. or less, 450° C. or less, 440° C. or less, 430° C. or less, 420° C. or less, or 410° C. or less). The temperature at which the film is heated during thermal annealing can range from any of the minimum values described above to any of the maximum values described above. For example, thermally annealing the film can comprise heating the film at a temperature of from 400° C. to 600° C. (e.g., from 400° C. to 500° C., from 500° C. to 600° C., from 400° C. to 450° C., from 450° C. to 500° C., from 500° C. to 550° C., from 550° C. to 600° C., from 450° C. to 550° C., or from 520° C. to 580° C.). In some examples, thermally annealing the film can comprise heating the film at a temperature of 550° C.

In some examples, the film can be thermally annealed for 1 hour or more (e.g., 1.5 hours or more, 2 hours or more, 2.5 hours or more, 3 hours or more, 3.5 hours or more, 4 hours or more, 4.5 hours or more, 5 hours or more, 5.5 hours or more, 6 hours or more, 6.5 hours or more, 7 hours or more, 7.5 hours or more, 8 hours or more, 8.5 hours or more, 9 hours or more, 9.5 hours or more, 10 hours or more, 10.5 hours or more, 11 hours or more, or 11.5 hours or more). In some examples, the film can be thermally annealed for 12 hours or less (e.g., 11.5 hours or less, 11 hours or less, 10.5 hours or less, 10 hours or less, 9.5 hours or less, 9 hours or less, 8.5 hours or less, 8 hours or less, 7.5 hours or less, 7 hours or less, 6.5 hours or less, 6 hours or less, 5.5 hours or less, 5 hours or less, 4.5 hours or less, 4 hours or less, 3.5 hours or less, 3 hours or less, 2.5 hours or less, 2 hours or less, or 1.5 hours or less). The time for which the film can be thermally annealed can range from any of the minimum values described above to any of the maximum values described above. For example, the film can be thermally annealed for from 1 hour to 12 hours (e.g., from 1 hour to 6 hours, from 6 hours to 12 hours, from 1 hour to 4 hours, from 4 hours to 8 hours, from 8 hours to 12 hours, from 1 hour to 10 hours, or from 1 hour to 3 hours). In some examples, the film can be thermally annealed for 2 hours.

The plasmonic substrate can be, for example, in thermal contact with a liquid sample comprising a plurality of particles. The liquid sample can further comprise, for example, an aqueous solvent.

The concentration of the plurality of particles in the liquid sample can be, for example, $10^3$ particles/mm$^3$ or more (e.g., $2.5 \times 10^3$ particles/mm$^3$ or more, $5 \times 10^3$ particles/mm$^3$ or more, $7.5 \times 10^3$ particles/mm$^3$ or more, $1 \times 10^4$ particles/mm$^3$ or more, $2.5 \times 10^4$ particles/mm$^3$ or more, $5 \times 10^4$ particles/mm$^3$ or more, $7.5 \times 10^4$ particles/mm$^3$ or more, $1 \times 10^5$ particles/mm$^3$ or more, $2.5 \times 10^5$ particles/mm$^3$ or more, $5 \times 10^5$ particles/mm$^3$ or more, $7.5 \times 10^5$ particles/mm$^3$ or more, $1 \times 10^6$ particles/mm$^3$ or more, $2.5 \times 10^6$ particles/mm$^3$ or more, $5 \times 10^6$ particles/mm$^3$ or more, $7.5 \times 10^6$ particles/mm$^3$ or more, $1 \times 10^7$ particles/mm$^3$ or more, $2.5 \times 10^7$ particles/mm$^3$ or more, $5 \times 10^7$ particles/mm$^3$ or more, $7.5 \times 10^7$ particles/mm$^3$ or more, $1 \times 10^8$ particles/mm$^3$ or more, $2.5 \times 10^8$ particles/mm$^3$ or more, $5 \times 10^8$ particles/mm$^3$ or more, $7.5 \times 10^8$ particles/mm$^3$ or more, $1 \times 10^9$ particles/mm$^3$ or more, $2.5 \times 10^9$ particles/mm$^3$ or more, $5 \times 10^9$ particles/mm$^3$ or more, or $7.5 \times 10^9$ particles/mm$^3$ or more).

In some examples, the concentration of the plurality of particles can be $10^{10}$ particles/mm$^3$ or less (e.g., $7.5 \times 10^9$ particles/mm$^3$ or less, $5 \times 10^9$ particles/mm$^3$ or less, $2.5 \times 10^9$ particles/mm$^3$ or less, $1 \times 10^9$ particles/mm$^3$ or less, $7.5 \times 10^8$ particles/mm$^3$ or less, $5 \times 10^8$ particles/mm$^3$ or less, $2.5 \times 10^8$ particles/mm$^3$ or less, $1 \times 10^8$ particles/mm$^3$ or less, $7.5 \times 10^7$ particles/mm$^3$ or less, $5 \times 10^7$ particles/mm$^3$ or less, $2.5 \times 10^7$ particles/mm$^3$ or less, $1 \times 10^7$ particles/mm$^3$ or less, $7.5 \times 10^6$ particles/mm$^3$ or less, $5 \times 10^6$ particles/mm$^3$ or less, $2.5 \times 10^6$ particles/mm$^3$ or less, $1 \times 10^6$ particles/mm$^3$ or less, $7.5 \times 10^5$ particles/mm$^3$ or less, $5 \times 10^5$ particles/mm$^3$ or less, $2.5 \times 10^5$ particles/mm$^3$ or less, $1 \times 10^5$ particles/mm$^3$ or less, $7.5 \times 10^4$ particles/mm$^3$ or less, $5 \times 10^4$ particles/mm$^3$ or less, $2.5 \times 10^4$ particles/mm$^3$ or less, $1 \times 10^4$ particles/mm$^3$ or less, $7.5 \times 10^3$ particles/mm$^3$ or less, $5 \times 10^3$ particles/mm$^3$ or less, or $2.5 \times 10^3$ particles/mm$^3$ or less).

The concentration of the plurality of particles in the liquid sample can range from any of the minimum values described above to any of the maximum values described above. For example, the concentration of the plurality of particles in the liquid sample can be from $10^3$ particles/mm$^3$ to $10^{10}$ particles/mm$^3$ (e.g., from $10^3$ particles/mm$^3$ to $10^6$ particles/mm$^3$, from $10^6$ particles/mm$^3$ to $10^{10}$ particles/mm$^3$, from $10^3$ particles/mm$^3$ to $10^5$ particles/mm$^3$, from $10^5$ particles/mm$^3$ to $10^7$ particles/mm$^3$, from $10^7$ particles/mm$^3$ to $10^{10}$ particles/mm$^3$, or from $10^4$ particles/mm$^3$ to $10^9$ particles/mm$^3$).

The plurality of particles in the liquid sample can have, for example, an average particle size of 4 nm or more (e.g., 5 nm or more, 10 nm or more, 15 nm or more, 20 nm or more, 25 nm or more, 30 nm or more, 35 nm or more, 40 nm or more, 45 nm or more, 50 nm or more, 75 nm or more, 100 nm or more, 125 nm or more, 150 nm or more, 175 nm or more, 200 nm or more, 225 nm or more, 250 nm or more, 275 nm or more, 300 nm or more, 325 nm or more, 350 nm or more, 375 nm or more, 400 nm or more, 425 nm or more, 450 nm or more, 475 nm or more, 500 nm or more, 550 nm or more, 600 nm or more, 650 nm or more, 700 nm or more, 750 nm or more, 800 nm or more, 850 nm or more, 900 nm or more, 950 nm or more, 1 µm or more, 2 µm or more, 3 µm or more, 4 µm or more, 5 µm or more, 6 µm or more, 7 µm or more, 8 µm or more, 9 µm or more, 10 µm or more, 11 µm or more, 12 µm or more, 13 µm or more, 14 µm or more, 15 µm or more, 16 µm or more, 17 µm or more, 18 µm or more, or 19 µm or more).

In some examples, the plurality of particles in the liquid sample can have an average particle diameter of 20 µm or less (e.g., 19 µm or less, 18 µm or less, 17 µm or less, 16 µm or less, 15 µm or less, 14 µm or less, 13 µm or less, 12 µm or less, 11 µm or less, 10 µm or less, 9 µm or less, 8 µm or less, 7 µm or less, 6 µm or less, 5 µm or less, 4 µm or less, 3 µm or less, 2 µm or less, 1 µm or less, 950 nm or less, 900 nm or less, 850 nm or less, 800 nm or less, 750 nm or less, 700 nm or less, 650 nm or less, 600 nm or less, 550 nm or less, 500 nm or less, 475 nm or less, 450 nm or less, 425 nm or less, 400 nm or less, 375 nm or less, 350 nm or less, 325 nm or less, 300 nm or less, 275 nm or less, 250 nm or less, 225 nm or less, 200 nm or less, 175 nm or less, 150 nm or less, 125 nm or less, 100 nm or less, 75 nm or less, 50 nm or less, 45 nm or less, 40 nm or less, 35 nm or less, 30 nm or less, 25 nm or less, 20 nm or less, 15 nm or less, 10 nm or less, or 5 nm or less).

The average particle size of the plurality of particles in the liquid sample can range from any of the minimum values described above to any of the maximum values described above. For example the plurality of particles in the liquid sample can have an average particle size of from 4 nm to 20 µm (e.g., from 4 nm to 10 µm, from 10 µm to 20 µm, from 4 nm to 1 µm, from 1 µm to 10 µm, from 10 µm to 20 µm, or from 50 nm to 15 µm).

In some examples, the plurality of particles in the liquid sample can comprise a plurality of thermoresponsive particles. Examples of thermoresponsive particles include, for example, polymer particles (e.g., polystyrene particles), polymer capped metal particles, or combinations thereof. In some examples, the plurality of particles in the liquid sample can comprise a plurality of polymer capped metal particles, such as a plurality of plasmonic particles, a plurality of quantum dots (e.g., comprising Cd Se, ZnS, or combinations thereof), or combinations thereof. In some examples, the plurality of particles in the liquid sample can comprise a plurality of polystyrene particles having an average particle size of from 60 nm to 10 µm. In some examples, the plurality of particles can comprise, a plurality of polystyrene spheres, a plurality of silica spheres, a plurality of quantum dots, a plurality of semiconductor nanowires, a plurality of biological cells (e.g., *E. coli*, yeast), or a combination thereof.

The methods can further comprise, for example, generating a bubble at a location in the liquid sample proximate to the first location of the plasmonic substrate, the bubble having a gas-liquid interface with the liquid sample. In some examples, the bubble is generated by plasmon-enhanced photothermal effects. The bubble can have a diameter of 100 nm or more (e.g., 150 nm or more, 200 nm or more, 250 nm or more, 300 nm or more, 350 nm or more, 400 nm or more, 450 nm or more, 500 nm or more, 650 nm or more, 700 nm or more, 750 nm or more, 800 nm or more, 850 nm or more, 900 nm or more, 950 nm or more, 1 µm or more, 2 µm or more, 3 µm or more, 4 µm or more, 5 µm or more, 6 µm or more, 7 µm or more, 8 µm or more, 9 µm or more, 10 µm or more, 20 µm or more, 30 µm or more, 40 µm or more, 50 µm or more, 60 µm or more, 70 µm or more, 80 µm or more, or 90 µm or more). In some examples, the bubble can have a diameter of 100 µm or less (e.g., 90 µm or less, 80 µm or less, 70 µm or less, 60 µm or less, 50 µm or less, 40 µm or less, 30 µm or less, 20 µm or less, 10 µm or less, 9 µm or less, 8 µm or less, 7 µm or less, 6 µm or less, 5 µm or less, 4 µm or less, 3 µm or less, 2 µm or less, 1 µm or less, 950 nm or less, 900 nm or less, 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, or 150 nm or less).

The diameter of the bubble can range from any of the minimum values described above to any of the maximum values described above. For example, the bubble can have a diameter of 100 nm or more (e.g., 150 nm or more, 200 nm or more, 250 nm or more, 300 nm or more, 350 nm or more, 400 nm or more, 450 nm or more, 500 nm or more, 550 nm or more, 600 nm or more, 650 nm or more, 700 nm or more, 750 nm or more, 800 nm or more, 850 nm or more, 900 nm or more, 950 nm or more, 1 µm or more, 2 µm or more, 3 µm or more, 4 µm or more, 5 µm or more, 6 µm or more, 7 µm or more, 8 µm or more, 9 µm or more, 10 µm or more, 15 µm or more, 20 µm or more, 25 µm or more, 30 µm or more, 35 µm or more, 40 µm or more, or 45 µm or more). In some examples, the bubble can have a diameter of 50 µm or less (e.g., 45 µm or less, 40 µm or less, 35 µm or less, 30 µm or less, 25 µm or less, 20 µm or less, 15 µm or less, 10 µm or less, 9 µm or less, 8 µm or less, 7 µm or less, 6 µm or less, 5 µm or less, 4 µm or less, 3 µm or less, 2 µm or less, 1 µm or less, 950 nm or less, 900 nm or less, 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, or 150 nm or less). The diameter of the bubble can range from any of the minimum values described above to any of the maximum values described above. For example, the bubble can have a diameter of from 100 nm to 50 µm (e.g., from 500 nm to 50 µm, from 100 nm to 25 µm, from 100 nm to 10 µm, from 100 nm to 5 µm, or from 100 nm to 1 µm). The diameter of the bubble can, for example, be controlled by the power density of the electromagnetic radiation used to illuminate the plasmonic substrate. The diameter of the bubble can be selected in view of a number of factors. In some examples, the diameter of the bubble can be selected relative to the average particle size of the plurality of particles in the liquid sample.

The methods can further comprise, for example, trapping at least a portion of the plurality of particles at the gas-liquid interface of the bubble and the liquid sample. The portion of the plurality of particles at the gas-liquid interface, for example, by convection, surface tension, gas pressure, substrate adhesion, or combinations thereof. In some examples, convection can comprise natural convection, Maragoni convection, or combinations thereof.

The portion of the plurality of particles can be trapped, for example, at a trapping speed of 10 µm/s or more (e.g., 15 µm/s or more, 20 µm/s or more, 25 µm/s or more, 30 µm/s or more, 35 µm/s or more, 40 µm/s or more, 45 µm/s or more, 50 µm/s or more, 55 µm/s or more, 60 µm/s or more, 65 µm/s or more, 70 µm/s or more, 75 µm/s or more, 80 µm/s or more, 85 µm/s or more, 90 µm/s or more, 95 µm/s or more, 100 µm/s or more, 125 µm/s or more, 150 µm/s or more, 175 µm/s or more, 200 µm/s or more, 225 µm/s or more, 250 µm/s or more, 275 µm/s or more, 300 µm/s or more, 325 µm/s or more, 350 µm/s or more, 375 µm/s or more, 400 µm/s or more, 425 µm/s or more, 450 µm/s or more, 475 µm/s or more, 500 µm/s or more, 525 µm/s or more, 550 µm/s or more, 575 µm/s or more, 600 µm/s or more, 625 µm/s or more, 650 µm/s or more, 675 µm/s or more, 700 µm/s or more, 725 µm/s or more, 750 µm/s or more, 775 µm/s or more, 800 µm/s or more, 825 µm/s or more, 850 µm/s or more, 875 µm/s or more, 900 µm/s or more, 925 µm/s or more, 950 µm/s or more, or 975 µm/s or more).

In some examples, the portion of the plurality of particles can be trapped at a trapping speed of 1000 µm/s or less (e.g., 975 µm/s or less, 950 µm/s or less, 925 µm/s or less, 900 µm/s or less, 875 µm/s or less, 850 µm/s or less, 825 µm/s or less, 800 µm/s or less, 775 µm/s or less, 750 µm/s or less, 725 µm/s or less, 700 µm/s or less, 675 µm/s or less, 650 µm/s or less, 625 µm/s or less, 600 µm/s or less, 575 µm/s or less, 550 µm/s or less, 525 µm/s or less, 500 µm/s or less, 475 µm/s or less, 450 µm/s or less, 425 µm/s or less, 400 µm/s or less, 375 µm/s or less, 350 µm/s or less, 325 µm/s or less, 300 µm/s or less, 275 µm/s or less, 250 µm/s or less, 225 µm/s or less, 200 µm/s or less, 175 µm/s or less, 150 µm/s or less, 125 µm/s or less, 100 µm/s or less, 95 µm/s or less, 90 µm/s or less, 85 µm/s or less, 80 µm/s or less, 75 µm/s or less, 70 µm/s or less, 65 µm/s or less, 60 µm/s or less, 55 µm/s or less, 50 µm/s or less, 45 µm/s or less, 40 µm/s or less, 35 µm/s or less, 30 µm/s or less, 25 µm/s or less, 20 µm/s or less, or 15 µm/s or less).

The speed at which portion of the plurality of particles are trapped can range from any of the minimum values described above to any of the maximum values described above. For example, the portion of the plurality of particles can be trapped at a trapping speed of from 10 µm/s to 1000 µm/s (e.g., from 5 µm/s to 500 µm/s, from 500 µm/s to 1000 µm/s, from 10 µm/s to 250 µm/s, from 250 µm/s to 500 µm/s, from 500 µm/s to 750 µm/s, from 750 µm/s to 1000 µm/s, from 10 µm/s to 100 µm/s, or from 15 µm/s to 35 µm/s).

The methods can further comprise, for example, depositing at least a portion of the plurality of particles on the plasmonic substrate at the first location. In some examples, the portion of the plurality of particles are not damaged during the deposition. In some examples, the portion of the plurality of particles deposited is one particle. In other words, also disclosed herein are methods for single-particle patterning.

In some examples, the portion of the plurality of particles can be deposited in an amount of time of 1 milliseconds (ms) or more (e.g., 5 ms or more, 10 ms or more, 20 ms or more, 30 ms or more, 40 ms or more, 50 ms or more, 60 ms or more, 70 ms or more, 80 ms or more, 90 ms or more, 100 ms or more, 125 ms or more, 150 ms or more, 175 ms or more, 200 ms or more, 225 ms or more, 250 ms or more, 275 ms or more, 300 ms or more, 325 ms or more, 350 ms or more, 375 ms or more, 400 ms or more, 425 ms or more, 450 ms or more, 475 ms or more, 500 ms or more, 550 ms or more, 600 ms or more, 650 ms or more, 700 ms or more, 750 ms or more, 800 ms or more, 850 ms or more, 900 ms or more, 950 ms or more, 1 s or more, 1.5 s or more, 2 s or more, 2.5 s or more, 3 s or more, 3.5 s or more, 4 s or more, or 4.5 s or more).

In some examples, the portion of the plurality of particles can be deposited in an amount of time of 5 seconds (s) or less (e.g., 4.5 s or less, 4 s or less, 3.5 s or less, 3 s or less, 2.5 s or less, 2 s or less, 1.5 s or less, 1 s or less, 950 ms or less, 900 ms or less, 850 ms or less, 800 ms or less, 750 ms or less, 700 ms or less, 650 ms or less, 600 ms or less, 550 ms or less, 500 ms or less, 475 ms or less, 450 ms or less, 425 ms or less, 400 ms or less, 375 ms or less, 350 ms or less, 325 ms or less, 300 ms or less, 275 ms or less, 250 ms or less, 225 ms or less, 200 ms or less, 175 ms or less, 150 ms or less, 125 ms or less, 100 ms or less, 90 ms or less, 80 ms or less, 70 ms or less, 60 ms or less, 50 ms or less, 40 ms or less, 30 ms or less, 20 ms or less, 10 ms or less, 5 ms or less).

The time in which the portion of the plurality of particles is deposited can range from any of the minimum values described above to any of the maximum values described above. For example, the portion of the plurality of particles can be deposited in an amount of time from 1 ms to 5 s (e.g., from 1 ms to 1 s, from 1 s to 5 s, from 1 ms to 500 ms, from 500 ms to 1 s, from 1 s to 2.5 s, from 2.5 s to 5 s, or from 1 ms to 2 s). For example, the portion of the plurality of particles can be deposited in 2 seconds or less. The time in which the portion of the plurality of particles can, for example, depend on the average particle size of the plurality of particles in the liquid sample, the concentration of the plurality of particles in the liquid sample, or combinations thereof.

In some examples, the portion of the plurality of particles deposited on the substrate are immobilized on the plasmonic substrate by surface adhesion. In some examples, the plasmonic substrate can further comprise a ligand and the portion of the plurality of particles deposited on the substrate are immobilized on the plasmonic substrate by electrostatic attraction and/or chemical recognition with the ligand (e.g., surface functionalization of the plasmonic substrate for particle immobilization).

In some examples, an additional layer is present between the plasmonic substrate and the liquid sample, the additional layer being in thermal contact with the plasmonic substrate and the liquid sample, such that the plurality of particles are deposited on the additional layer. The additional layer can, for example, comprise a two-dimensional atomic layer material, such as $MoS_2$, $WSe_2$, $MoTe_2$, $WS_2$, hexagonal BN, graphene, or combinations thereof.

The methods can further comprise, for example, illuminating a second location of the plasmonic substrate to deposit another portion of the plurality of particles at the second location. As used herein, "a second location" and "the second location" are meant to include any number of locations in any arrangement on the plasmonic substrate. Thus, for example "a second location" includes one or more second locations. In some embodiments, the second location can comprise a plurality of locations. In some embodiments, the second location can comprise a plurality of locations arranged in an ordered array. In some examples, the plasmonic substrate and/or the light source can be translocated to illuminate the second location.

Also disclosed herein are patterned substrate made using the methods described herein. Also disclosed herein are methods of use of patterned substrates made using the methods described herein, for example using the patterned substrates for single-particle sensing, single-cell analysis, tissue engineering, functional optical devices, or combinations thereof.

Also disclosed herein are systems for performing the methods described herein. Referring now to FIG. 1, the systems 100 can comprise a plasmonic substrate 102 in thermal contact with a liquid sample 104 comprising a plurality of particles 106; and a light source 108 configured to illuminate the plasmonic substrate at a first location 110.

In some examples, the system 100 can include a single light source 108. In other examples, more than one light source 108 can be included in the system 100.

In some examples, the systems can further comprise a means for translocating the plasmonic substrate and/or the light source.

Figure 2:
FIG. 2 is a schematic of an exemplary system as disclosed herein for lithography.
Figure 2:
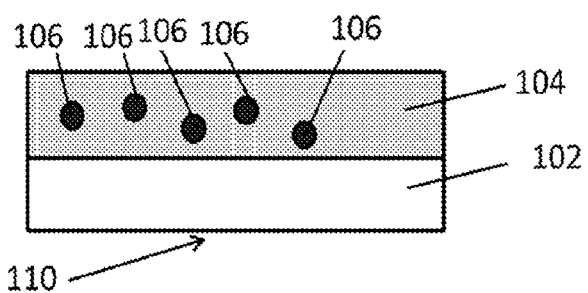
Figure 2:
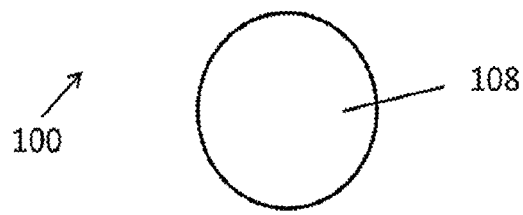

Referring now to FIG. 2, the system 110 can, in some examples, further comprise an instrument 112 configured to capture an electromagnetic signal from the plasmonic substrate 102.

In some examples, the system 110 can further comprise a first lens 114. In some examples, the system 110 can further comprise a second lens 116. The lenses may independently be any type of lens, such as a simple lens, a compound lens, a spherical lens, a toric lens, a biconvex lens, a plano-convex lens, a plano-concave lens, a negative meniscus lens, a positive meniscus lens, a biconcave lens, a converging lens, a diverging lens, a cylindrical lens, a Fresnel lens, a lenticular lens, or a gradient index lens.

Figure 3:
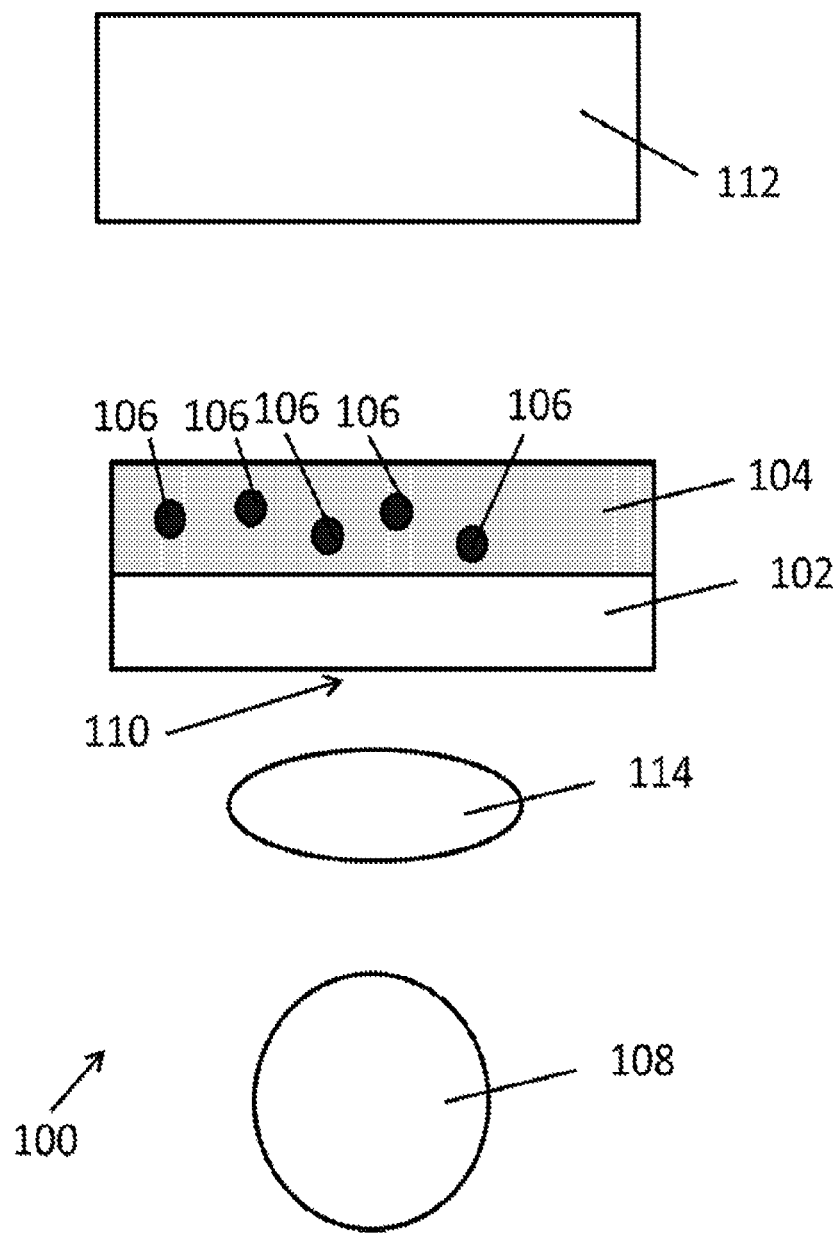
FIG. 3 is a schematic of an exemplary system as disclosed herein for lithography.

Referring now to FIG. 3, in some examples, the system 110 can be configured such that the light source 108 is below the first lens 114 and the plasmonic substrate 102 is above the first lens 114.

Figure 4:
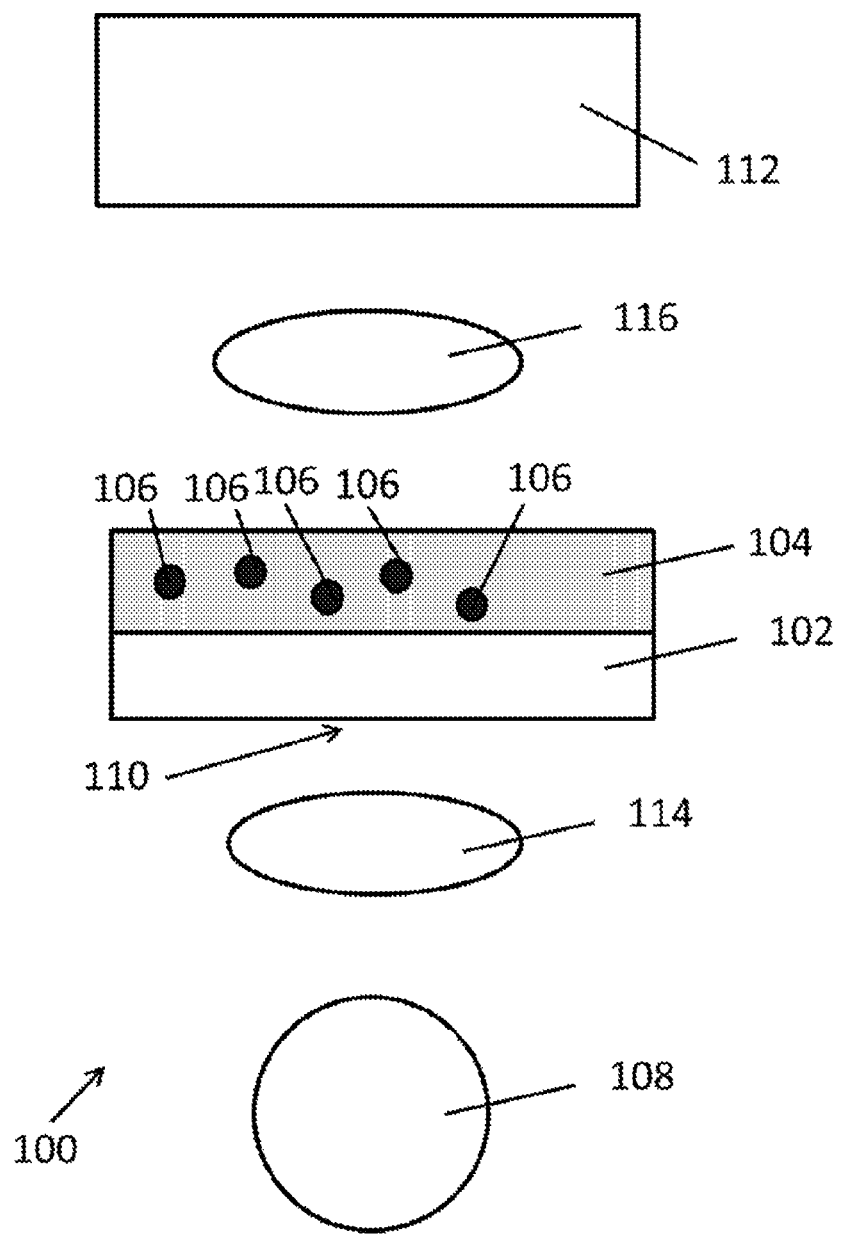
FIG. 4 is a schematic of an exemplary system as disclosed herein for lithography.

Referring now to FIG. 4, in some examples, the system 110 is aligned such that the light source 108 is below the first lens 114, the plasmonic substrate 102 is above the first lens 114, the second lens 116 is above the plasmonic substrate 102, and the instrument 112 is above the second lens 116.

Figure 5:
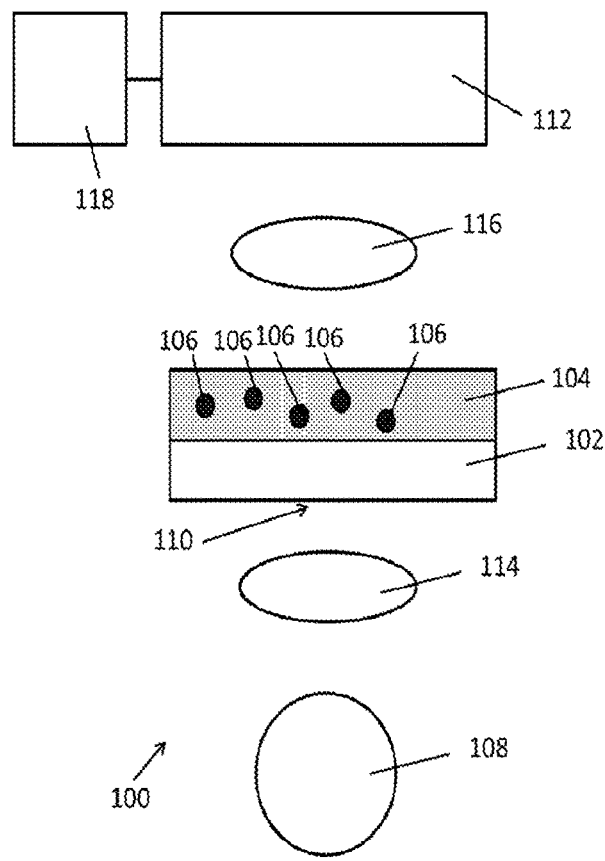
FIG. 5 is a schematic of an exemplary system as disclosed herein for lithography.

In some example, the systems 110 can further comprise a computing device 118 configured to receive and process electromagnetic signals from the instrument 112, for example as shown in FIG. 5.

Figure 6:
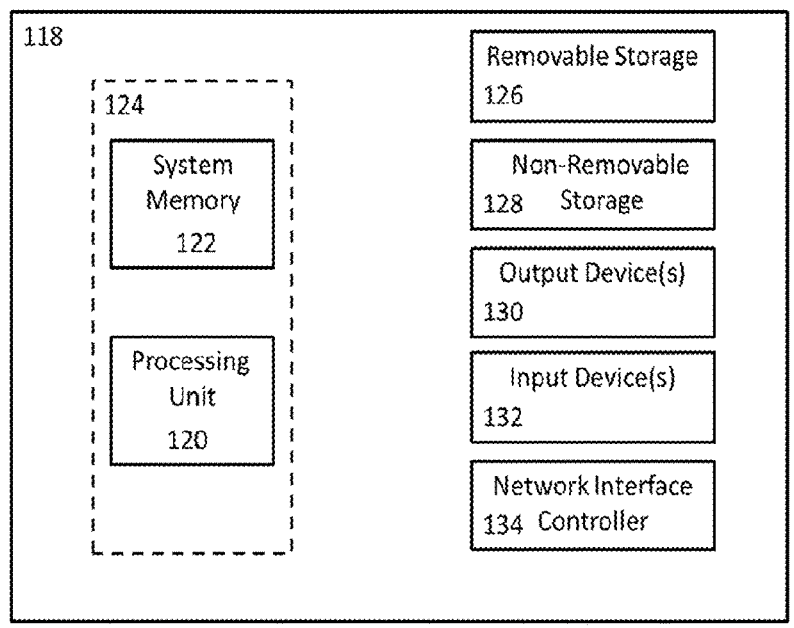
FIG. 6 is a schematic of an exemplary computing device.

FIG. 6 illustrates an example computing device 118 upon which examples disclosed herein may be implemented. The computing device 118 can include a bus or other communication mechanism for communicating information among various components of the computing device 118. In its most basic configuration, computing device 118 typically includes at least one processing unit 120 (a processor) and system memory 122. Depending on the exact configuration and type of computing device, system memory 122 may be volatile (such as random access memory (RAM)), non-volatile (such as read-only memory (ROM), flash memory, etc.), or some combination of the two. This most basic configuration is illustrated in FIG. 6 by a dashed line 124. The processing unit 120 may be a standard programmable processor that performs arithmetic and logic operations necessary for operation of the computing device 118.

The computing device 118 can have additional features/functionality. For example, computing device 118 may include additional storage such as removable storage 126 and non-removable storage 128 including, but not limited to, magnetic or optical disks or tapes. The computing device 118 can also contain network connection(s) 134 that allow the device to communicate with other devices. The computing device 118 can also have input device(s) 132 such as a keyboard, mouse, touch screen, antenna or other systems configured to communicate with the camera in the system described above, etc. Output device(s) 130 such as a display, speakers, printer, etc. may also be included. The additional devices can be connected to the bus in order to facilitate communication of data among the components of the computing device 118.

The processing unit 120 can be configured to execute program code encoded in tangible, computer-readable media. Computer-readable media refers to any media that is capable of providing data that causes the computing device 118 (i.e., a machine) to operate in a particular fashion. Various computer-readable media can be utilized to provide instructions to the processing unit 120 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 120 can execute program code stored in the system memory 122. For example, the bus can carry data to the system memory 122, from which the processing unit 120 receives and executes instructions. The data received by the system memory 122 can optionally be stored on the removable storage 126 or the non-removable storage 128 before or after execution by the processing unit 120.

The computing device 118 typically includes a variety of computer-readable media. Computer-readable media can be any available media that can be accessed by device 118 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 122, removable storage 126, and non-removable storage 128 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 118. Any such computer storage media can be part of computing device 118.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, system memory 122 comprises computer-executable instructions stored thereon that, when executed by the processor 120, cause the processor 120 to receive an electromagnetic signal from the instrument 112, process the electromagnetic signal to obtain a characteristic of the plasmonic substrate 102; and output the characteristic of the plasmonic substrate 102.

The analysis of signals captured by the instrument can be carried out in whole or in part on one or more computing device. For example, the system may comprise one or more additional computing device.

The instrument can comprise, for example, a camera, an optical microscope, an electron microscope, a spectrometer, or combinations thereof. Examples of spectrometers include, but are not limited to, Raman spectrometers, UV-vis absorption spectrometers, IR absorption spectrometers, fluorescence spectrometers, and combinations thereof.

In some examples, the electromagnetic signal received by the processor from the instrument can comprise an image, a spectrum (e.g., Raman, UV-vis, IR, fluorescence), a micrograph, or combinations thereof. The characteristic of the plasmonic substrate can comprise, for example, the presence, location, size, shape, and/or quantity of a portion of the plurality of particles deposited thereon; the presence, location, composition, size, shape, and/or quantity of plasmonic particles comprising the plasmonic substrate; or combinations thereof. In some examples, the characteristic of the plasmonic substrate can be monitored over time, for example, to identify the effect of depositing the portion of the plurality of particles on the plasmonic substrate.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1

Figure 7:
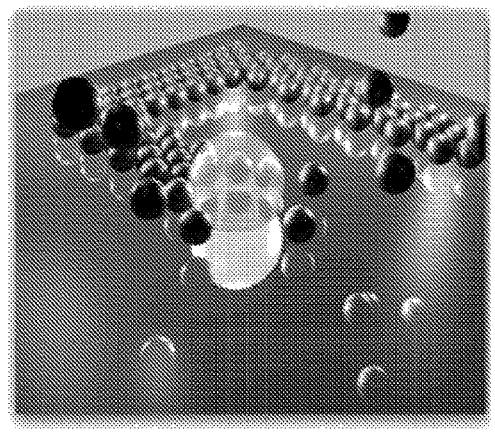
FIG. 7 is a schematic illustration of the bubble-pen lithography method.

Herein, a new method referred to as "bubble-pen lithography" is discussed (shown schematically in FIG. 7). The bubble-pen lithography methods can optically write arbitrary patterns of colloidal particles on the substrates. In bubble-pen lithography, an optically controlled microbubble is generated to capture and immobilize colloidal particles on plasmonic substrates through the coordinated actions of Marangoni convection, surface tension, gas pressure, and/or substrate adhesion in the substrate-bubble-solution system. The irradiation of a plasmonic substrate with a focused laser beam at the plasmon resonance wavelength generates a microbubble at the substrate-solution interface. Due to plasmon-enhanced photothermal effects, bubbles of variable sizes can be generated at reduced power. Bubble-pen lithography can generate bubbles 1 µm or less in diameter, which are much smaller than the microbubbles (diameter in the range of 50-100 µm) commonly used in microfluidic devices for manipulation of particles (Hu W et al. Lab Chip 2012, 12, 3821-3826; Hashmi A et al. Lab Chip 2012, 12, 4216-4227; Zhao C et al. Lab Chip 2014, 14, 384-391).

Figure 9:
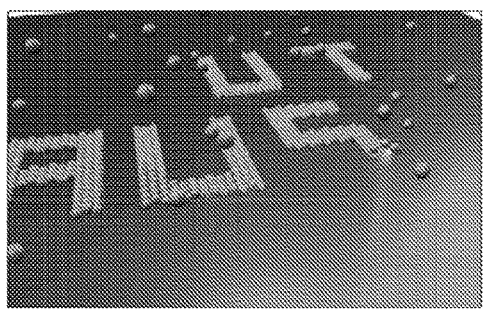
FIG. 9 is a schematic illustration of the pattern-writing process using an optically controlled microbubble on a plasmonic substrate. The small blue spheres are colloidal particles.
Figure 8:
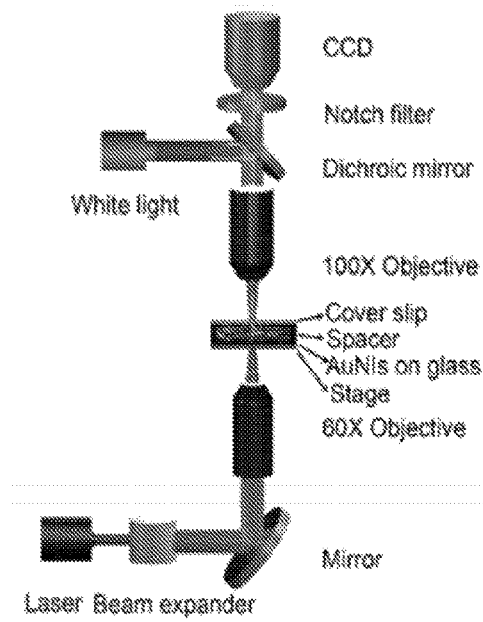
FIG. 8 is a schematic illustration of the experimental setup for bubble-pen lithography.

FIG. 8 illustrates the experimental setup for bubble-pen lithography. A laser beam is focused onto the plasmonic substrate by a high-magnification objective from the bottom of the sample. An optical microscope with a white light source, objectives, and a CCD is integrated into the system for real-time monitoring of the patterning process. Colloidal particles suspended in deionized (DI) water were sandwiched between a plasmonic substrate and a cover slip with a 120 µm spacer. As illustrated in FIG. 9 (and FIG. 7), a microbubble is generated on the plasmonic substrate upon irradiation with a laser beam 2 micrometer in diameter due to water vaporization from plasmon-enhanced photothermal effects (Fang Z et al. Nano Lett. 2013, 13, 1736-1742; Neumann O et al. ACS Nano 2013, 7, 42-49). The colloidal particles are dragged towards the microbubble, trapped on the bubble/water interface and immobilized on the substrate. Patterns of particles can be created that can be controlled by the formation of bubbles which in turn can be controlled by the laser beam placement and/or trajectory.

Figure 10:
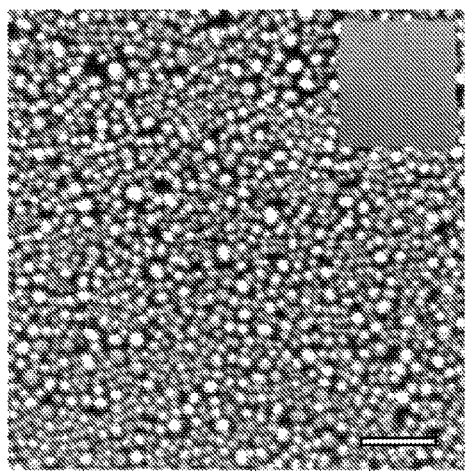
FIG. 10 is a scanning electron micrograph (SEM) (FEI Quanta 650 ESEM) of the plasmonic substrate comprising Au nanoislands formed by thermal annealing (550° C., 2 hours) of a gold film with an initial thickness of 4 nm. The inset shows an optical image of the sample.
Figure 11:
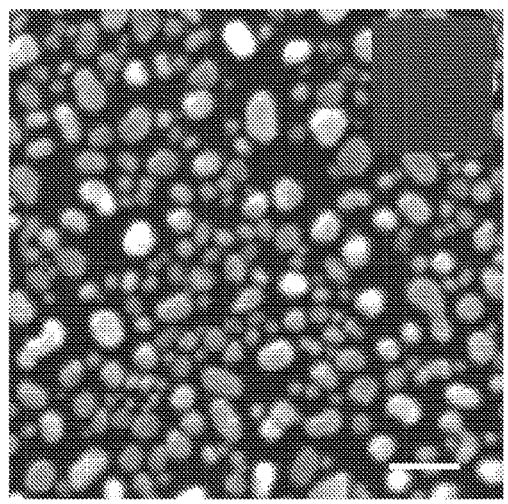
FIG. 11 is a scanning electron micrograph (SEM) (FEI Quanta 650 ESEM) of the plasmonic substrate comprising Au nanoislands formed by thermal annealing (550° C., 2 hours) of a gold film with an initial thickness of 6.5 nm. The inset shows an optical image of the sample.
Figure 12:
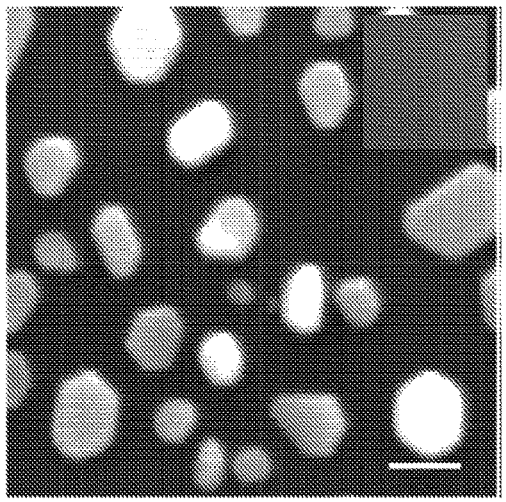
FIG. 12 is a scanning electron micrograph (SEM) (FEI Quanta 650 ESEM) of the plasmonic substrate comprising Au nanoislands formed by thermal annealing (550° C., 2 hours) of a gold film with an initial thickness of 10 nm. The inset shows an optical image of the sample.
Figure 13:
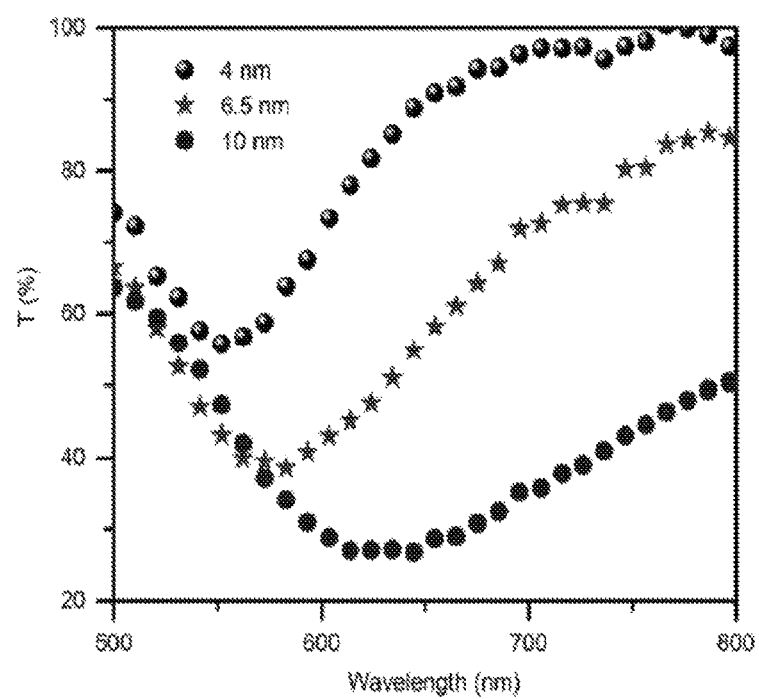
FIG. 13 shows the absorption spectra of the plasmonic substrates comprising Au nanoislands formed by thermal annealing (550° C., 2 hours) of a gold films with varying initial thickness (thickness indicated in legend).

Herein, the plasmonic substrates were comprised of gold nanoislands, which were tuned so that their plasmon resonance wavelength matched the laser wavelength (532 nm) and so that the substrates had high nanoparticle density in order to minimize the optical power needed for bubble generation. To fabricate the gold nanoisland plasmonic substrates, Au films of varying thickness (e.g., 4 nm, 6.5 nm, 10 nm) were deposited on the glass substrate with thermal deposition (Denton thermal evaporator) at the base pressure of $9 \times 10^{-6}$ Torr, followed by the thermal annealing at 550° C. for 2 hours. Scanning electron micrographs of the gold nanoisland plasmonic substrates after annealing are shown in FIG. 10, FIG. 11, and FIG. 12 for gold nanoisland plasmonic substrates fabricated using Au films with an initial thickness of 4 nm, 6.5 nm, and 10 nm, respectively. It can be seen that as the thickness of the initial film increased, the density of the nanoislands in the final substrate decreased. The absorption spectra of the gold nanoislands were taken using the Ocean Optics spectrometer (HR4000CG-UV-NIR), and the resulting absorption spectra are shown in FIG. 13. The plasmonic substrate fabricated using a Au film 4 nm thick exhibited the highest nanoisland density and had a plasmon resonance wavelength that most closely matched the laser wavelength (532 nm).

Figure 14:
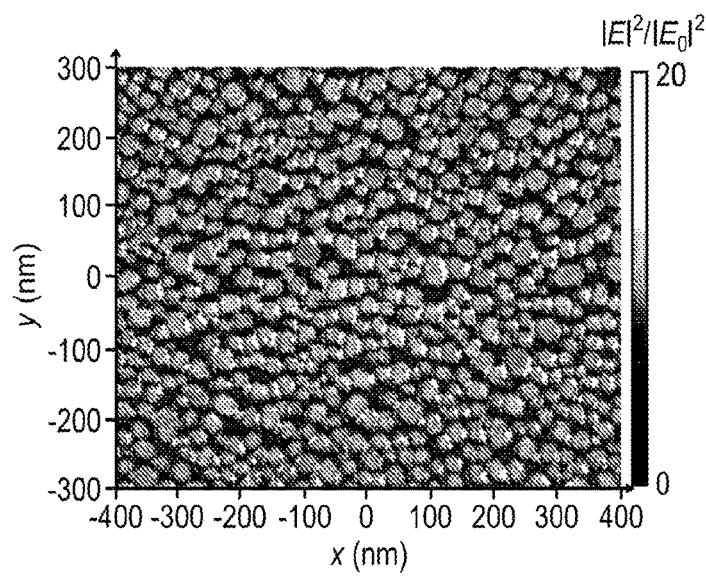
FIG. 14 shows an overlay of scanning electron microscopy (SEM) image (Hitachi S5500 SEM/STEM system) and simulated electric field distributions of quasi-continuous Au nanoislands (AuNIs).

The typical plasmonic substrate had Au nanoparticles of 20-40 nm in diameter and 5-10 nm in inter-particle distances with the particle density of $1\times10^{11}$ particles/cm² (FIG. 14). 3D electromagnetic simulations were performed with commercial software (FDTD Solutions, Lumerical Solutions) to model the electromagnetic properties of the plasmonic substrate. The geometry of the gold nanoislands was imported from the high-resolution SEM images, which was defined with a fine mesh size of 1 nm. The optical constants of Au were taken from Johnson and Christy (Johnson P and Christy R. *Phys. Rev. B* 1972, 6, 4370-4379), and the refractive index of the glass substrate is set as 1.52. A broadband plane wave was used to illuminate the gold nanoislands. Perfectly matched layers were utilized as the boundary conditions for all directions. The electromagnetic field distributions were recorded at the excitation wavelength of 532 nm, which matches the laser wavelength used in the experiments.

Figure 15:
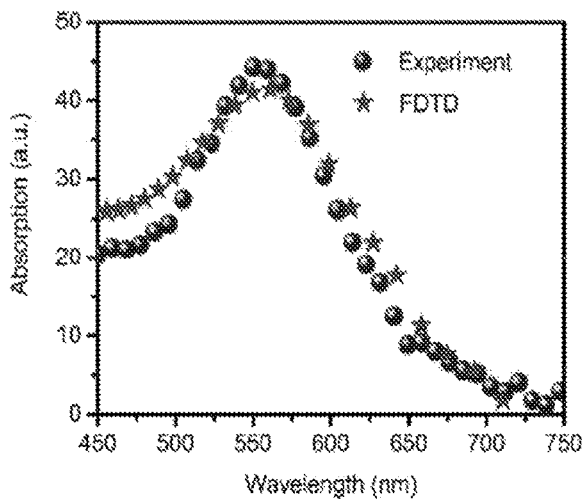
FIG. 15 shows the simulated and experimental absorption spectra of the gold nanoisland substrate.

As shown by the simulated electromagnetic field distributions over the SEM image of the gold nanoislands (FIG. 14), the laser irradiation leads to high-density electromagnetic "hot spots" that arise from the strong near-field coupling between the neighboring Au nanoparticles. The network of "hot spots" on the gold nanoislands can allow for spatially continuous generation of microbubbles for arbitrary patterning. Both simulated and experimental absorption spectra (FIG. 15) reveal that the plasmon resonance peak wavelength of the gold nanoislands matched the laser wavelength, which can enhance the light absorption and photothermal effects, which can in turn allow for low-power bubble generation.

Figure 16:
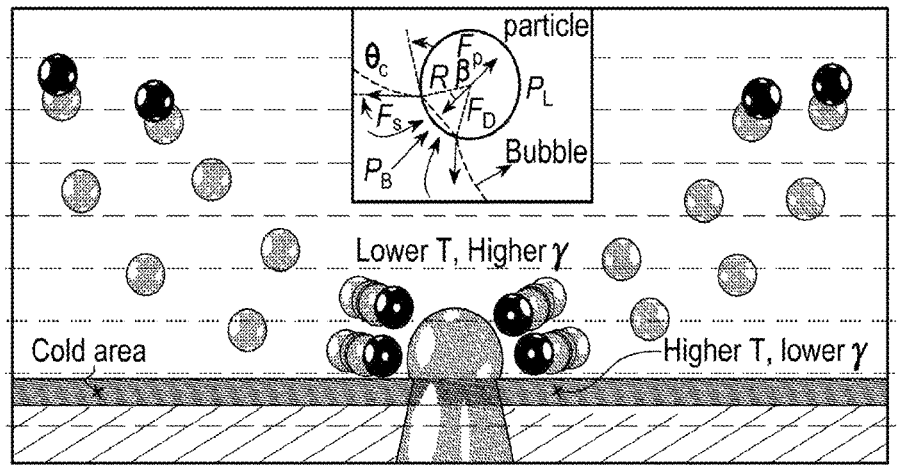
FIG. 16 is a schematic illustration (in a cross-sectional view) of the particle-trapping mechanism by a single microbubble generated through the plasmon-enhanced photothermal effects. The blue spheres indicate the suspended particles in the DI water. The particles follow the convective flow due to the frictional force. The inset shows the force distributions when a particle is trapped by the microbubble (indicated as the red dash line). $P_B$ and $P_L$ indicate the pressure in the bubble and liquid, respectively, which introduce a net force of $F_P$ pushing the particle outwards. The surface tension $F_S$ introduce a drag force $F_D$.

In bubble-pen lithography, both natural convection and Marangoni convection can contribute to the particle trapping at the microbubbles. The former is caused by the temperature gradient on the plasmonic substrate. The latter is induced by the surface-tension gradient along the microbubble surface (FIG. 16). The convective flow can drag the colloidal particles down to the plasmonic substrate and the in-plane drag force can drive the particles towards the microbubble. Trapping can occur when a particle touches the microbubble, as shown in the inset of FIG. 16. The surface tension force $F_S$ at the gas/liquid interface leads to an effective drag force $F_D$, which attracts the particle towards the microbubble. The pressure inside the microbubble, which can reach 3.4 bar for the 1 μm bubble (Baffou G et al. *J. Phys. Chem. C* 2014, 118, 4890-4898), is higher than the pressure in the surrounding water, which can be treated as atmospheric pressure. Balance is achieved when the ratio between $F_D$ and $F_P$ becomes 1:

$$\frac{F_D}{F_P} = \left(\frac{R_B}{R}\right)\left(\frac{\sin|\theta_C - \beta|}{\sin \beta}\right) = 1 \quad (1)$$

where $R_B$ is the radius of the microbubble, $F_P$ is the force induced by the gas/liquid pressure difference, R is the radius of the colloidal particles, $\theta_C$ is the contact angle between the particle and the bubble, and β is the half-central angle.

Computational fluid dynamics (CFD) simulations were conducted using a finite-element solver (COMSOL Multiphysics). For simplicity, a 2D axisymmetric model comprising of glass substrate, polystyrene beads, stream microbubble, and water was established. The physics involved included fluid dynamics in laminar flow (water and stream) and conjugate heat transfer in solids (glass substrate and polystyrene beads) and fluids (water and stream). Three kinds of couplings were considered in the simulations, including non-isothermal flow multiphysics coupling, Marangoni effect multiphysics coupling, and gravity, which introduces buoyant force. The boundary conditions considered for the heat transfer composed a boundary heat source at the glass/stream bubble interface (to model the laser heating) and room temperature for other boundaries. For the laminar flow physics, the water/stream bubble interface was set as a slip interior wall while the other boundaries were set as non-slip walls.

Figure 17:
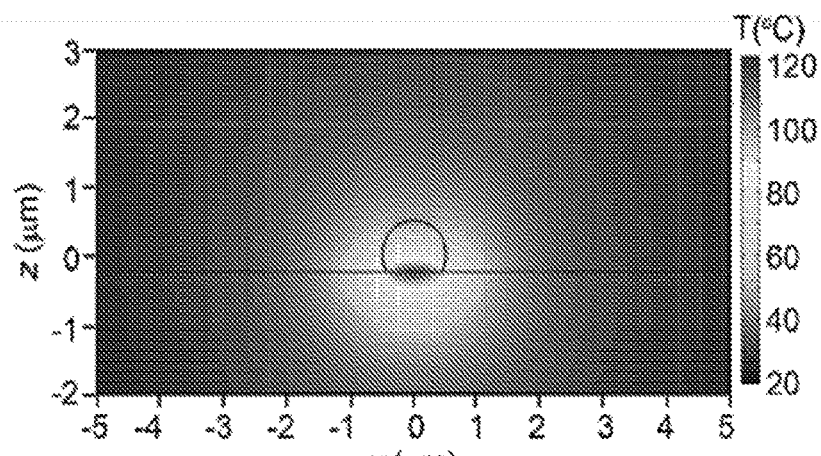
FIG. 17 shows the simulated temperature distributions around a 1 µm bubble in a cross-sectional view.
Figure 18:
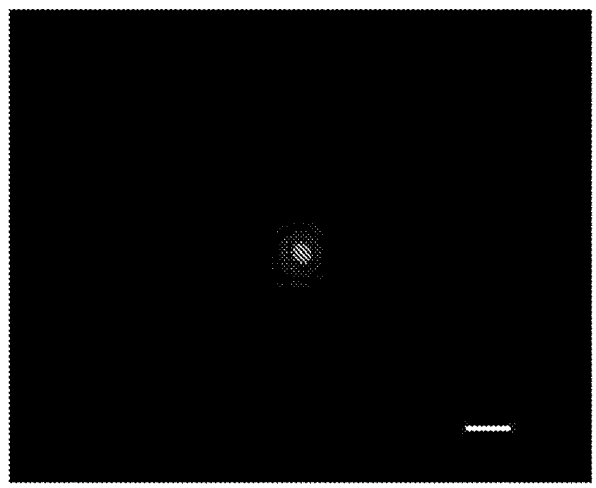
FIG. 18 is an optical image of a laser beam used for the generation of a microbubble. The size of the laser beam is 2 µm. The scale bar is 5 µm.
Figure 19:
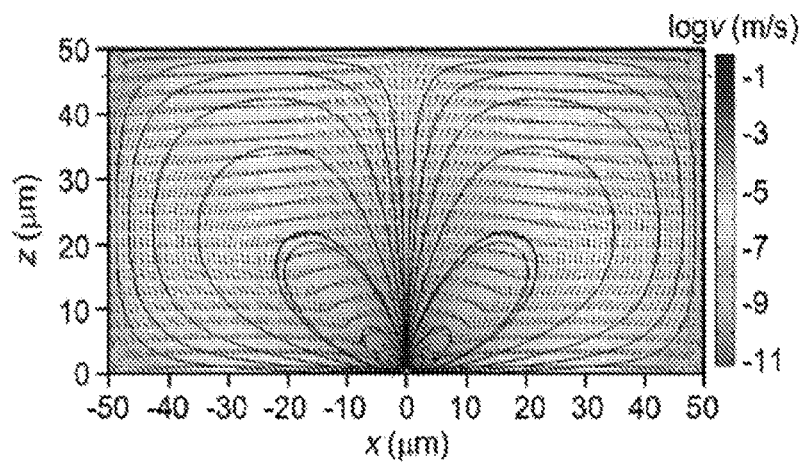
FIG. 19 shows the simulated flow velocity distributions around a 1 µm bubble with logarithmic scale in a cross-sectional view. The black lines indicate streamlines of the convective flow.

Computational fluid dynamics (CFD) simulations were used to obtain the temperature distribution around a 1 μm bubble (FIG. 17) when the substrate was illuminated by a focused laser beam with a diameter of 2 μm (FIG. 18) and power density of 0.56 mW/μm² (measured at the focus point of the objective). The resultant bottom-to-top temperature difference of ~60° C. can create a surface tension gradient along the bubble surface. The flow velocity distribution around the 1 μm bubble is displayed in FIG. 19, with a maximum flow velocity of ~0.3 m/s at the gas/liquid interface. The flow velocity decreases when the distance from the microbubble is increased. It ranges from 1 to 100 μm/s at the distances of 15-5 μm. Due to the convective flow, the particles are dragged towards the microbubble according to Stokes' law:

$$F_d = 6\pi\mu R v(R) \quad (2)$$

where μ is the dynamic viscosity of the solution and v(R) is the flow velocity of solvent relative to the particles, which is also dependent on R. As shown in FIG. 19, the mass center of the larger particles is farther away from the substrate surfaces, causing the larger particles to experience a different flow velocity than the smaller particles. At a constant mass density, the acceleration of the particles is estimated according to Equation 3.

$$\alpha \propto \mu R^{-2} v(R) \quad (3)$$

Figure 20:
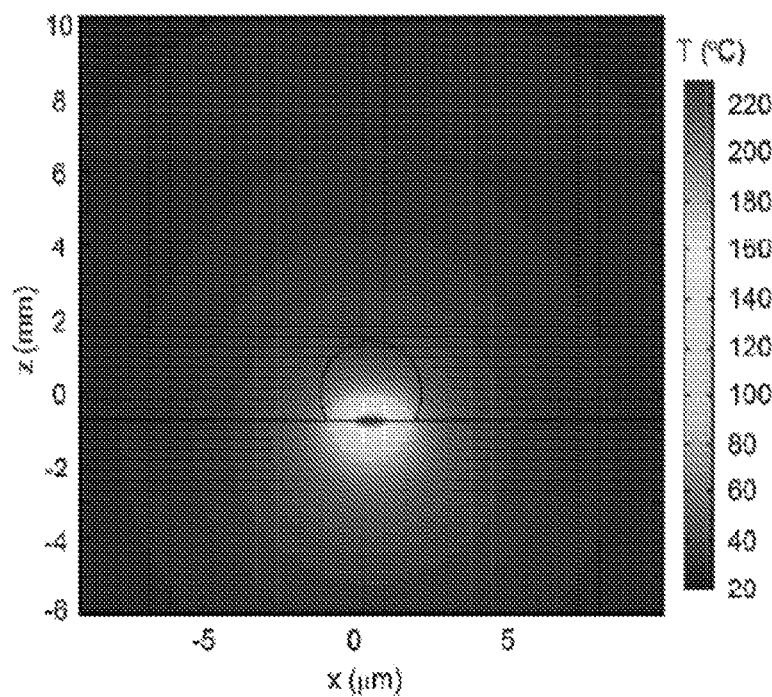
FIG. 20 shows the simulated temperature distributions around a 3 µm bubble generated using a laser power intensity of 0.97 mW/µm$^2$. The maximum temperature is at the center of the bubble/substrate interface and is 220° C. The minimum temperature around the bubble is ~20° C.
Figure 21:
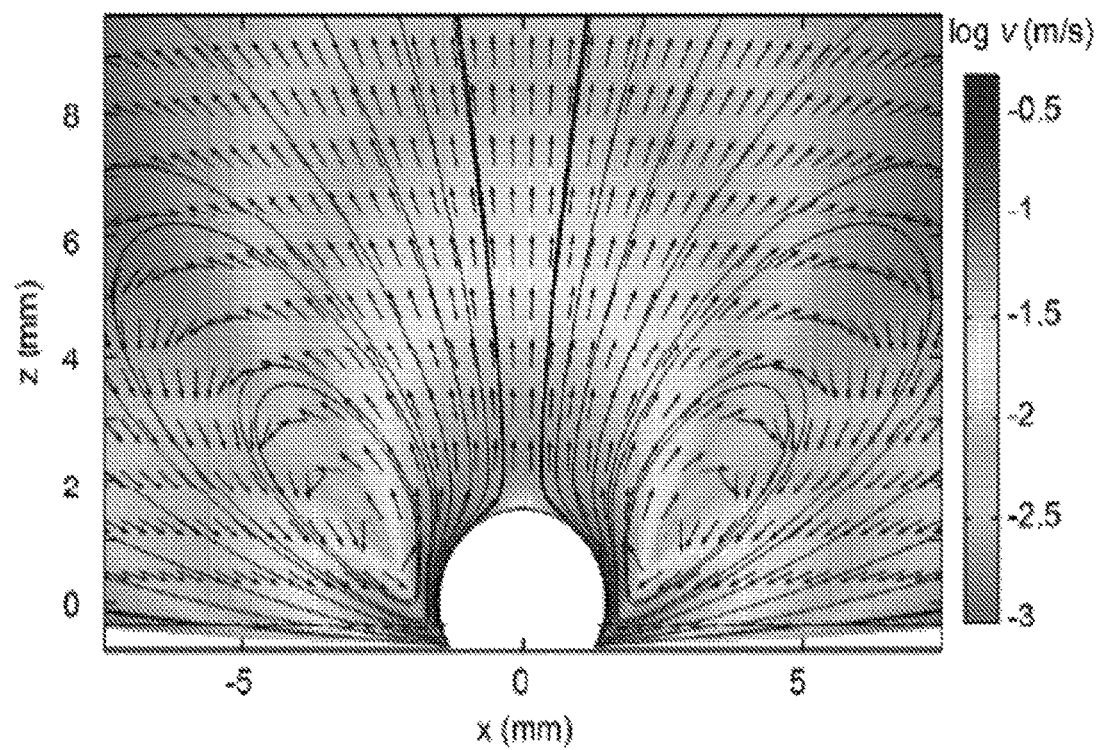
FIG. 21 shows the simulated flow velocity distributions around a 3 µm bubble with logarithmic scale in a cross-sectional view. The laser power intensity is 0.97 mW/µm$^2$. The black lines indicate streamlines of the convective flow. A maximum flow velocity of ~0.5 m/s is generated around the bubble.

Similarly, FIG. 20 and FIG. 21 shows the computational fluid dynamics simulations of the temperature distribution and flow velocity for a 3 μm bubble, respectively.

Figure 22:
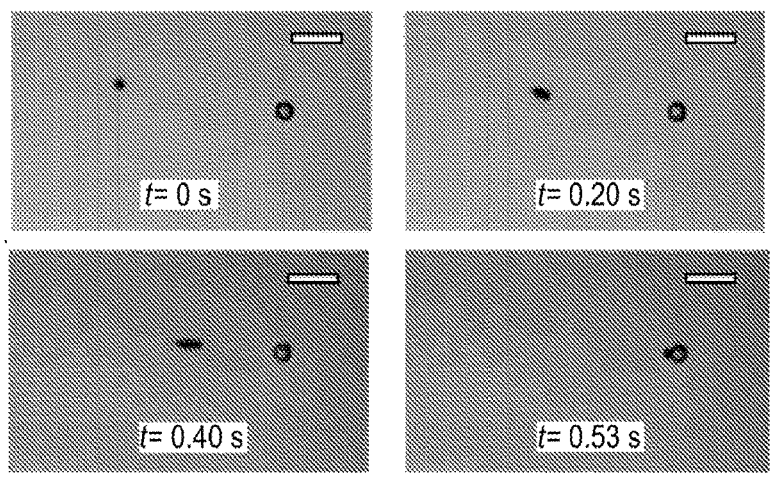
FIG. 22 shows the time-resolved trapping process of a single 540 nm polystyrene bead by a 1 µm bubble. The diameter and power density of the laser beam are 2 µm and 0.56 mW/µm$^2$. The average trapping speed is estimated to be 31.1 µm/s. Scale bar: 5 µm.
Figure 23:
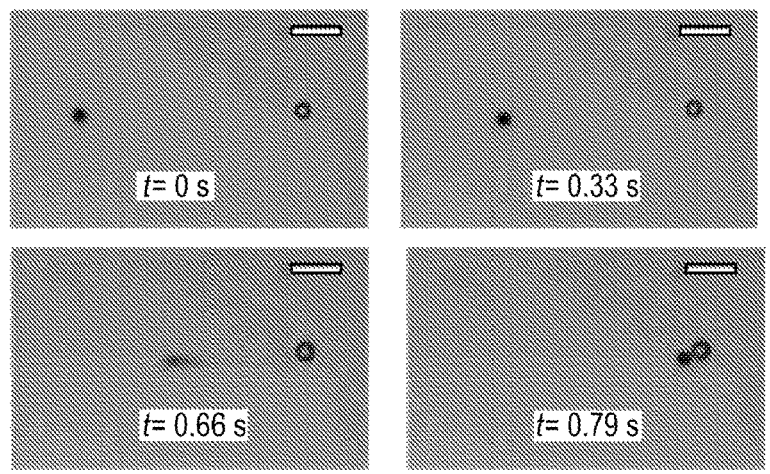
FIG. 23 shows the time-resolved trapping process of a single 0.96 µm polystyrene bead by a 1 µm bubble. The diameter and power density of the laser beam are 2 µm and 0.56 mW/µm$^2$. The average trapping speed is estimated to be 27.5 µm/s. Scale bar: 5 µm.
Figure 24:
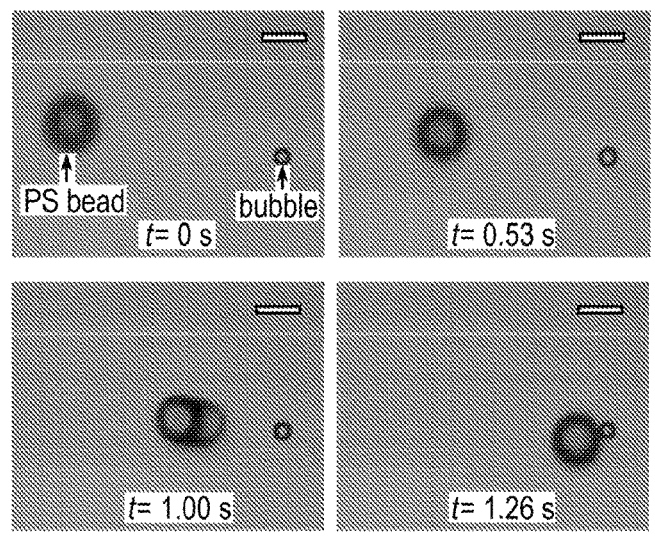
FIG. 24 shows the time-resolved trapping process of a single 5.31 µm polystyrene bead by a 1 µm bubble. Scale bar: 5 µm.

The particle-trapping speed was measured by recording the time-resolved trapping processes of single polystyrene beads with diameters of 540 nm, 0.96 μm, and 5.31 μm, with the time-resolved trapping process shown in FIG. 22, FIG. 23, and FIG. 24, respectively (polystyrene beads with sizes of 60 nm (1 wt. %), 540 nm (9.83 wt. %), 0.96 μm (10 wt. %), 5.31 μm (9.6 wt. %) and 9.51 μm (10.08 wt. %) were ordered from Bangs Laboratories, Inc.). A traveling distance of ~20 μm was used to estimate the average trapping speed. The 5.31 μm polystyrene bead exhibited a speed of 18.1 μm/s. The drag force and trapping speed can depend on the distance between the particle and the microbubble. There is an increase of the trapping speed when the particle approaches the microbubble (FIG. 24), indicating that the relative velocity v dominates the trapping process. In addition, the smaller polystyrene beads experience higher trapping speed (27.5 μm/s for the 0.96 μm polystyrene and 31.1 μm/s for the 540 nm polystyrene, respectively).

Figure 25:
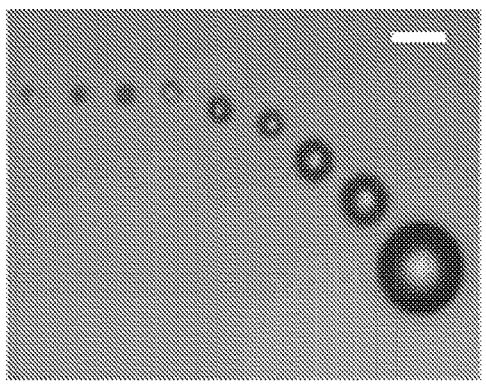
FIG. 25 shows the optical micrographs of a series of microbubbles generated with different laser power densities: 0.56, 0.64, 0.68, 0.77, 0.83, 0.91, 0.97, 1.04, and 1.12 mW/µm$^2$ (from small to large bubbles). It should be noted that the bubble pattern was generated in series by translating the sample stage and recorded in sequence. Scale bar is 5 µm.
Figure 26:
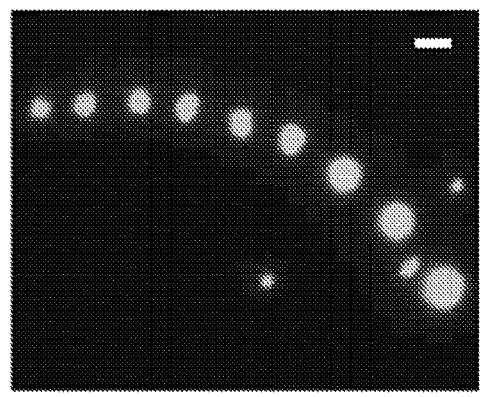
FIG. 26 shows the dark-field optical micrographs of the series of patterned 540 nm polystyrene beads generated with corresponding power densities in FIG. 25. (d) High-magnification image of the 3D hollow structure formed at a laser power density of 0.97 mW/µm$^2$. The flow velocity distributions (logarithmic scale) around a 3 µm microbubble in a cross-sectional view when (e) single layer (f) three layers and (g) five layers of 540 nm polystyrene beads are trapped at the gas/liquid interface. Scale bar is 5 µm.
Figure 27:
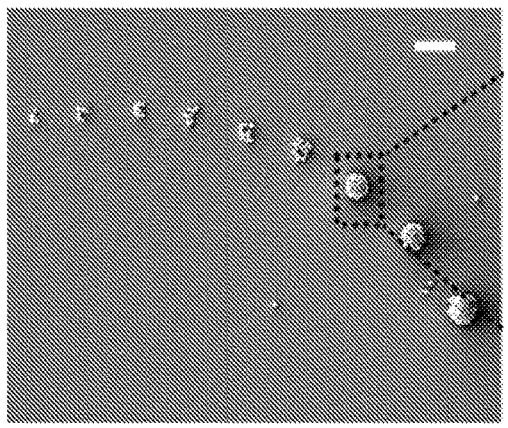
FIG. 27 is a scanning electron micrograph (SEM) (FEI Quanta 650 ESEM) of the series of patterned 540 nm polystyrene beads generated with corresponding power densities in FIG. 19. Scale bar is 5 µm.
Figure 28:
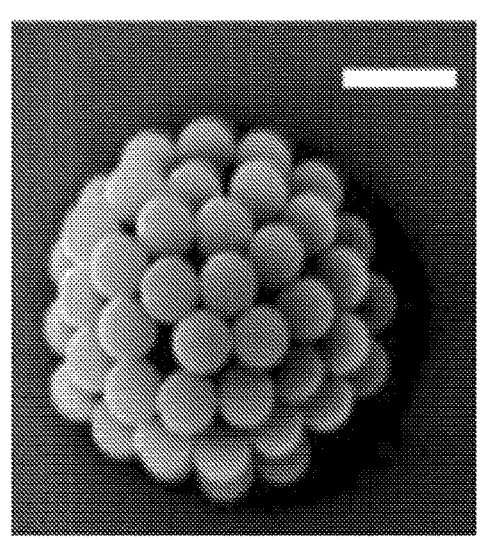
FIG. 28 is a high-magnification scanning electron micrograph (SEM) (FEI Quanta 650 ESEM) of the 3D hollow structure formed at a laser power density of 0.97 mW/µm$^2$. Scale bar is 1 µm.

Plasmon-enhanced photothermal effects were used to immobilize the bubble-trapped particles on the substrates for particle patterning as the plasmon-enhanced photothermal effects can improve the adhesion between the polystyrene beads and the substrate. FIG. 25 shows the optical micrographs of the variable microbubbles generated under illumination with different power densities. The smallest bubble, with a diameter of 1 µm, was generated at a laser power density of 0.56 mW/µm$^2$. An increase in the optical power density enlarged the bubbles, because an increased amount of water steam was generated and more air molecules diffused into the bubbles. As shown in FIG. 26 and FIG. 27, the 540 nm polystyrene beads can be immobilized on the substrate by the bubbles, leading to the different patterns. At the lowest optical power density, three polystyrene beads formed a cluster with a two-dimensional (2D) configuration. When the power density was increased to 0.97 mW/µm$^2$, a larger bubble with a diameter of >3 µm lead to a three-dimensional (3D) hollow structure of the beads on the substrate (FIG. 28), revealing that the trapped polystyrene beads are aligned along the whole gas/liquid interface. In addition to the bubble size, the patterns of beads can also depend on the concentration of the beads in the solution and the laser irradiation time.

Figure 29:
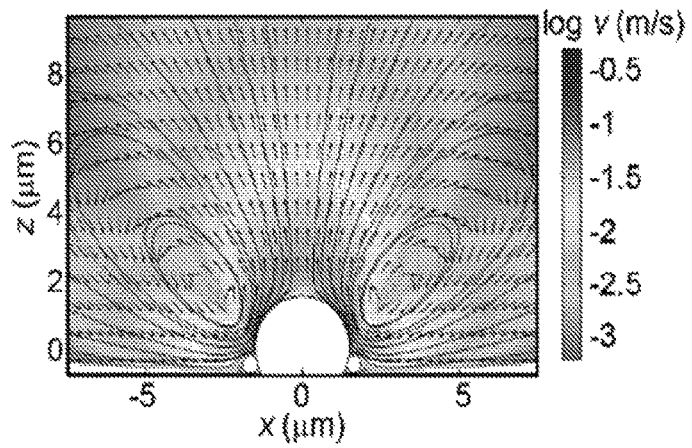
FIG. 29 shows the flow velocity distributions (logarithmic scale) around a 3 µm microbubble in a cross-sectional view when a single layer of 540 nm polystyrene beads is trapped at the gas/liquid interface.
Figure 30:
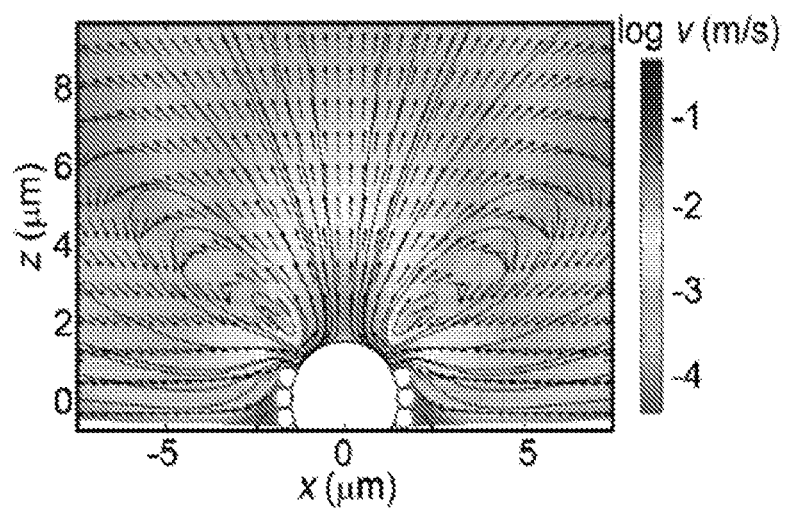
FIG. 30 shows the flow velocity distributions (logarithmic scale) around a 3 µm microbubble in a cross-sectional view when three layers of 540 nm polystyrene beads are trapped at the gas/liquid interface.
Figure 31:
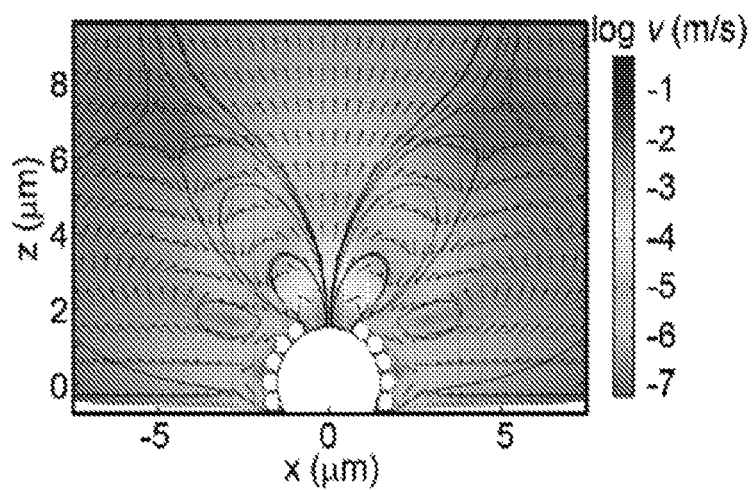
FIG. 31 shows the flow velocity distributions (logarithmic scale) around a 3 µm microbubble in a cross-sectional view when five layers of 540 nm polystyrene beads are trapped at the gas/liquid interface.

Computational fluid dynamics (CFD) simulations were used to gain insight into the formation mechanism of the 3D hollow structures of polystyrene beads. As illustrated in FIG. 29-FIG. 31, the convective flow drags the beads towards the bubble/substrate interface and generates the 3D hollow structure by "bottom-up" layer-by-layer stacking. Such a stacking process can be enabled as the initially trapped beads at the bubble surface block the Marangoni stress and modify the convective flow distributions in a way that the convective flow points toward the upper part of the bubble. In addition, the trapped beads reduce the surface tension gradient and thus the flow velocity along the bubble surface. However, a reverse convective flow occurs when the bubble traps five layers of beads (FIG. 31). The reverse flow pushes the free beads in suspension away from the trapped ones. The velocity around the microbubble is 4-5 orders of magnitude lower than that before the beads are trapped, indicating that the trapping process stops once the bubble surface is covered with beads. The 3D hollow structures are generated when the microbubbles are larger than the beads.

Figure 32:
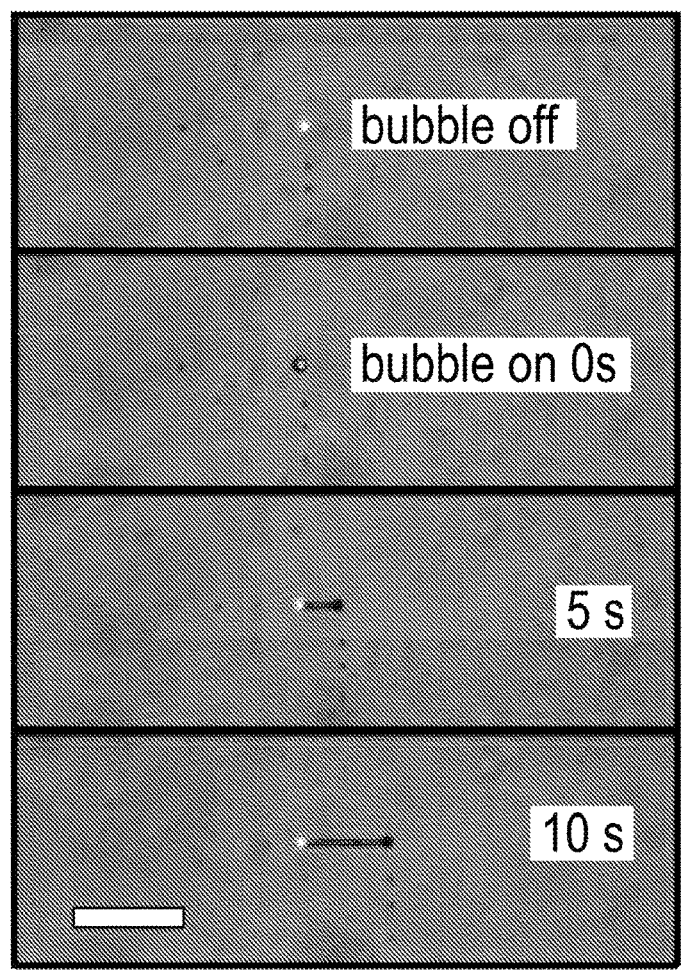
FIG. 32 shows the time-resolved process for continuous writing of a straight-line pattern of 540 nm polystyrene beads on the gold nanoislands substrate. Scale bar is 50 µm.

Taking advantage of the quasi-continuous gold nanoislands as the plasmonic substrate, continuous writing of the patterns of colloidal particles on the substrate was achieved by scanning the laser beam and/or translating the sample stage. For the continuous patterning, the 540 nm polystyrene solution was diluted with DI water (1:1,000, v/v). FIG. 32 illustrates the writing process for a straight line of 540 nm polystyrene beads at a laser power density of 0.56 mW/µm$^2$. At the lower power density (top panel of FIG. 32), no microbubble was generated. Still, the optically generated temperature gradient led to natural convection, moving the polystyrene beads upward at the illuminated area without trapping and immobilization. When the laser power density was increased to the "critical value", a microbubble was generated and the polystyrene beads were collected and immobilized on the illuminated spot (second panel in FIG. 32). During translation of the sample stage, the original microbubbles disappeared, leaving behind the immobilized beads, and new ones were generated at the new locations to trap and immobilize beads, leading to patterns of beads that follow the trail of the bubbles (third and fourth panels in FIG. 32).

Figure 33:
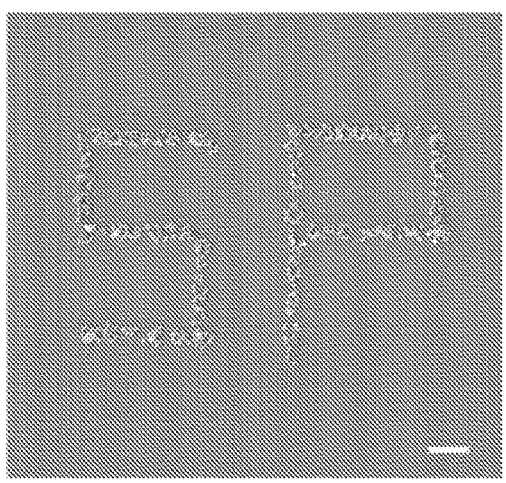
FIG. 33 shows the scanning electron micrograph (FEI Quanta 650 ESEM) of the 540 nm polystyrene beads in the "SP" pattern. Scale bar is 5 µm.
Figure 34:
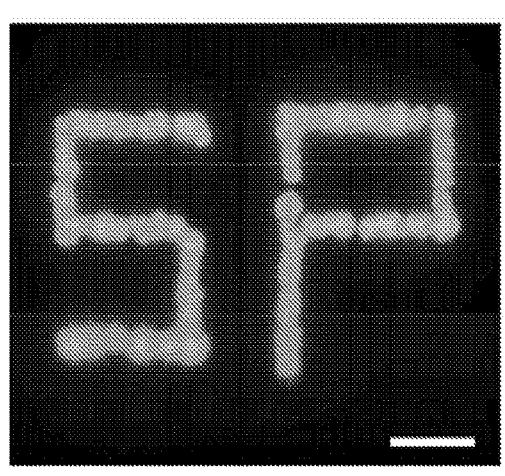
FIG. 34 shows the dark-field optical image of the "SP" patterns of 540 nm polystyrene beads. Scale bar is 10 µm.
Figure 35:
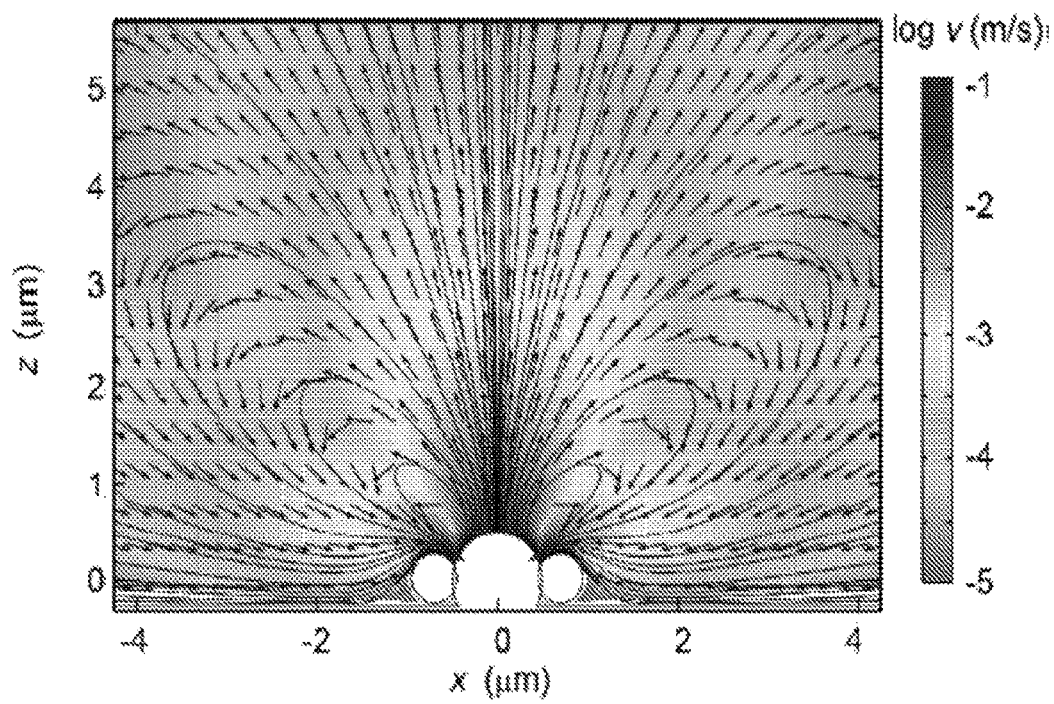
FIG. 35 shows the flow velocity distributions (logarithmic scale) around a 1 µm microbubble in a cross-sectional view when 540 nm polystyrene beads are trapped at the gas/liquid interface. The trapping of the first layer of polystyrene beads modifies the flow velocity distributions. The beads can subsequently be trapped either around or on top of the first layer. The 3D hollow structure cannot be formed due to the limited bubble surface area.

As an example, "SP" patterns of 540 nm polystyrene beads were written using a 1 µm microbubble (SEM, FIG. 33; dark-field image, FIG. 34). Since the size of the polystyrene beads and the microbubble were comparable (540 nm vs. 1 µm), one-layer or two-layer 2D aggregates are generated due to the limited surface area of the bubbles (FIG. 35). Due to the high trapping and immobilization efficiencies, the microbubble can allow for rapid scanning of the laser beam and the high-throughput patterning at a large scale.

Figure 36:
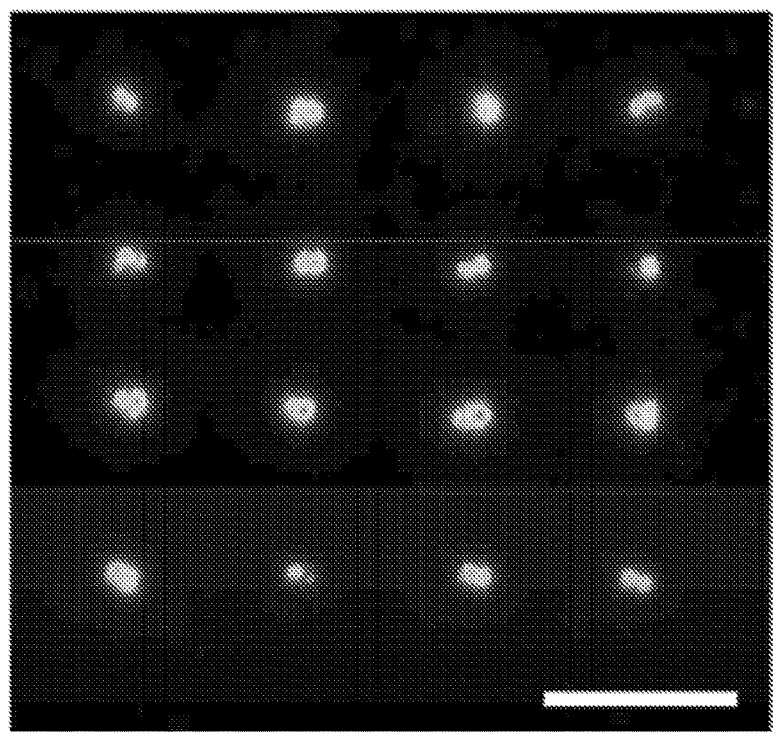
FIG. 36 shows the dark-field optical image of the 4×4 arrays of 3D hollow structures of 60 nm polystyrene beads. Scale bar is 10 µm.
Figure 37:
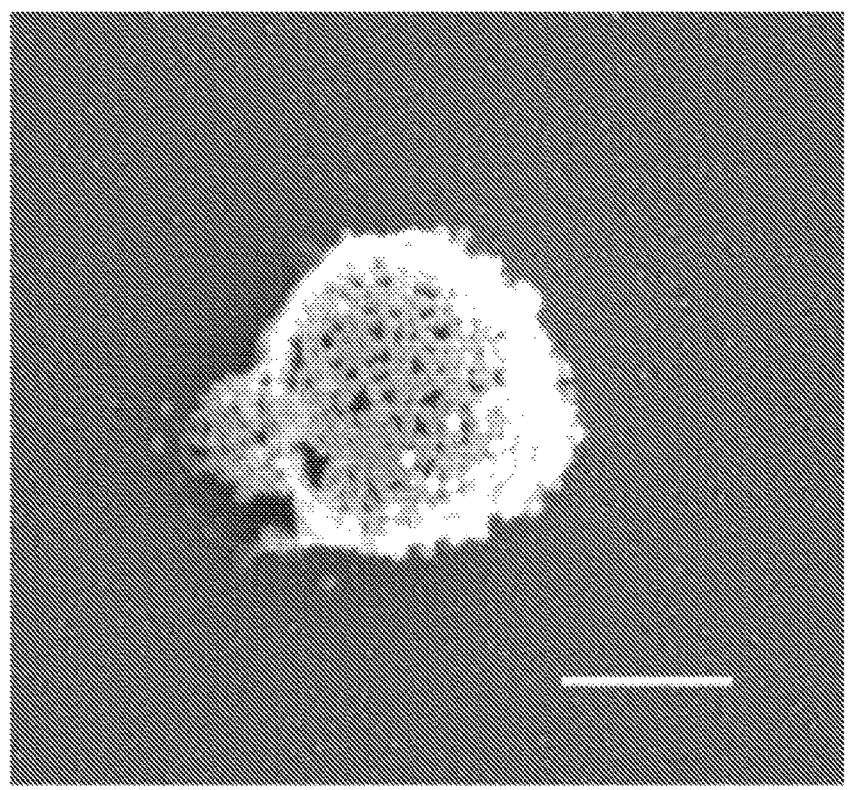
FIG. 37 shows the scanning electron micrograph (FEI Quanta 650 ESEM) of the 3D hollow structure of 60 nm polystyrene beads. Scale bar is 1 µm.
Figure 38:
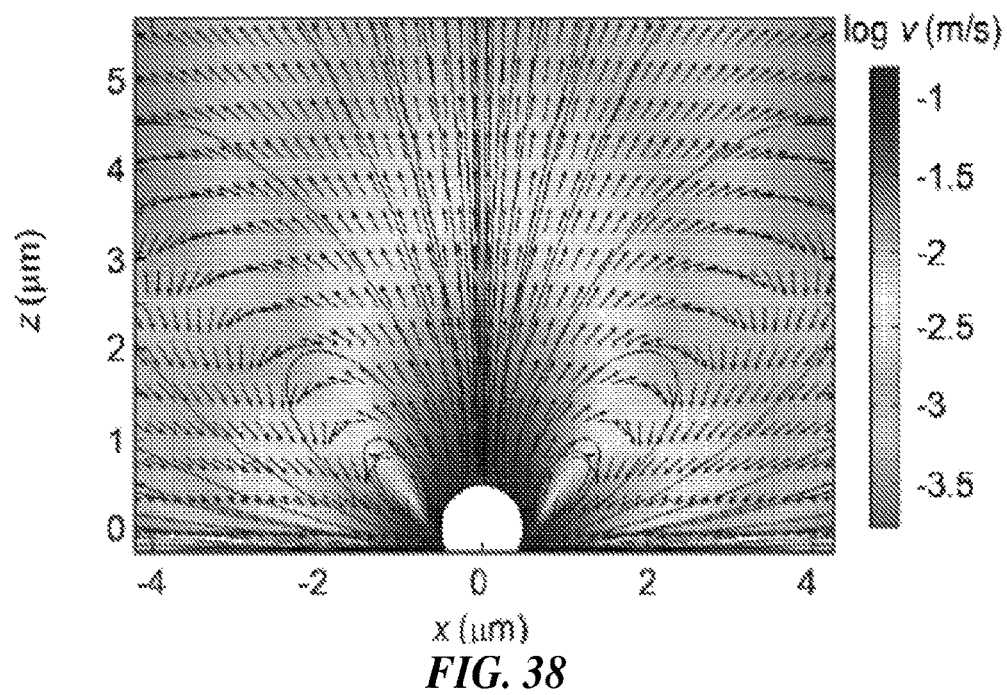
FIG. 38 shows the flow velocity distributions (logarithmic scale) around a 1 µm microbubble in a cross-sectional view when zero layers of 60 nm polystyrene beads are trapped at the gas/liquid interface.
Figure 39:
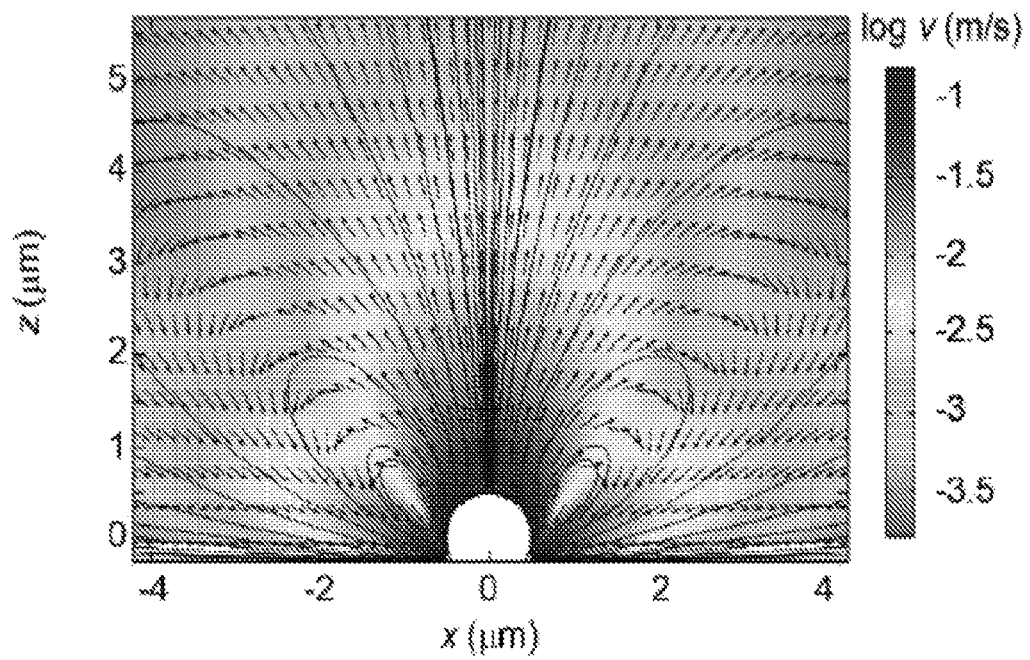
FIG. 39 shows the flow velocity distributions (logarithmic scale) around a 1 µm microbubble in a cross-sectional view when one layer of 60 nm polystyrene beads are trapped at the gas/liquid interface.
Figure 40:
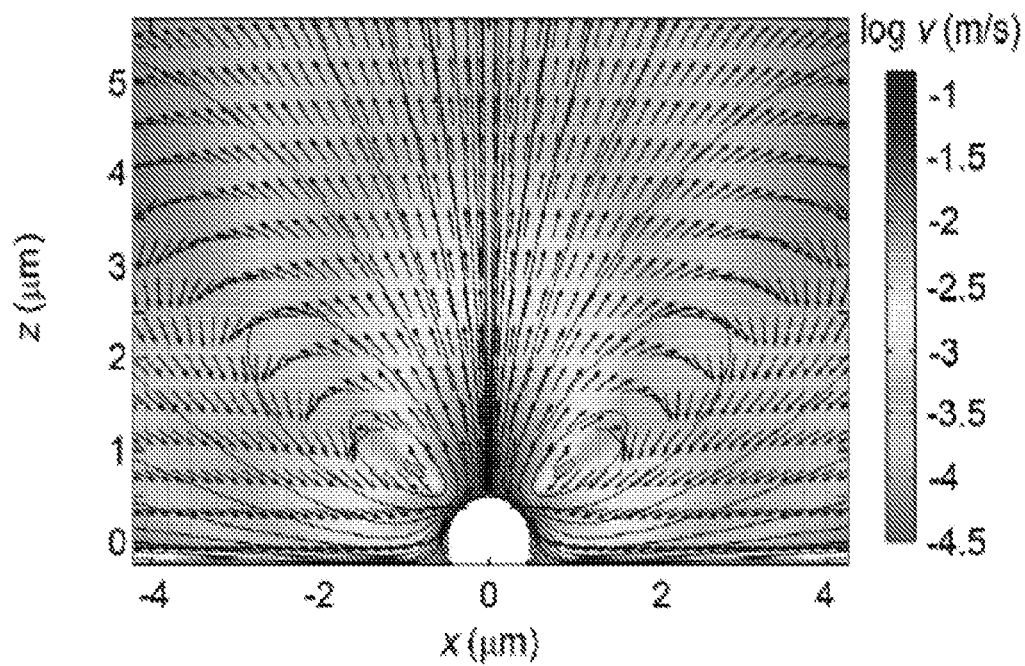
FIG. 40 shows the flow velocity distributions (logarithmic scale) around a 1 µm microbubble in a cross-sectional view when seven layers of 60 nm polystyrene beads are trapped at the gas/liquid interface.
Figure 41:
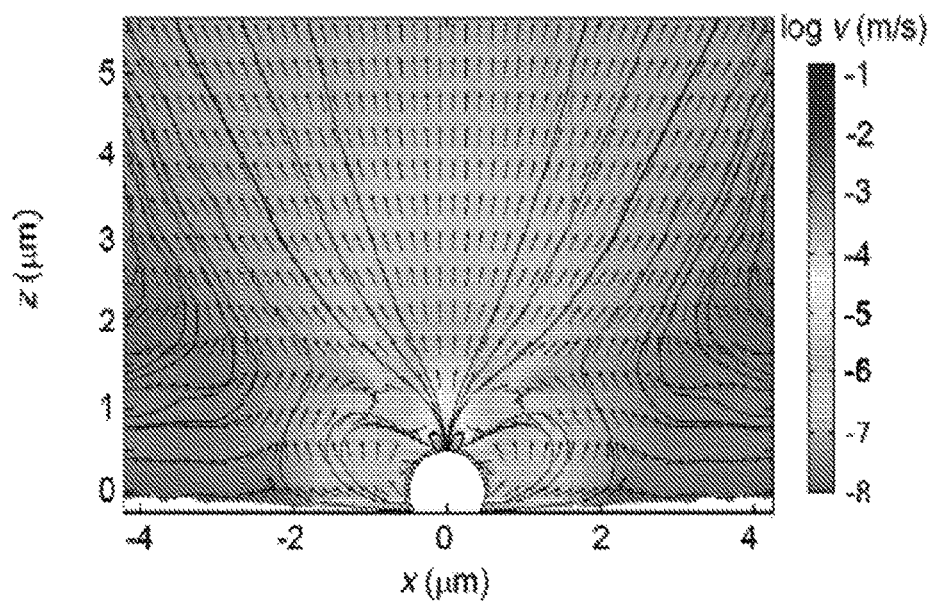
FIG. 41 shows the flow velocity distributions (logarithmic scale) around a 1 µm microbubble in a cross-sectional view when thirteen layers of 60 nm polystyrene beads are trapped at the gas/liquid interface.
Figure 42:
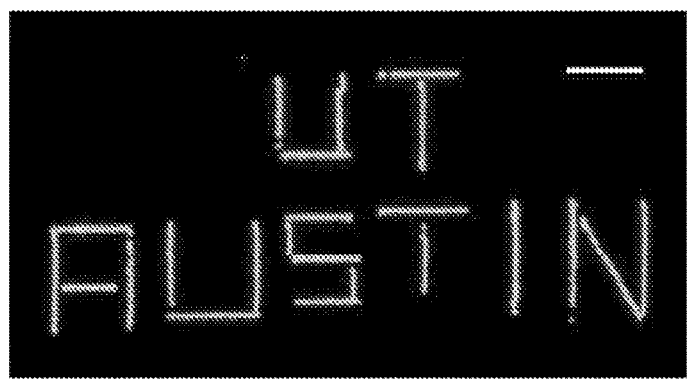
FIG. 42 shows the dark-field optical image of "UT AUSTIN" pattern formed with continuous writing of 60 nm polystyrene beads. Scale bar is 25 µm.
Figure 43:
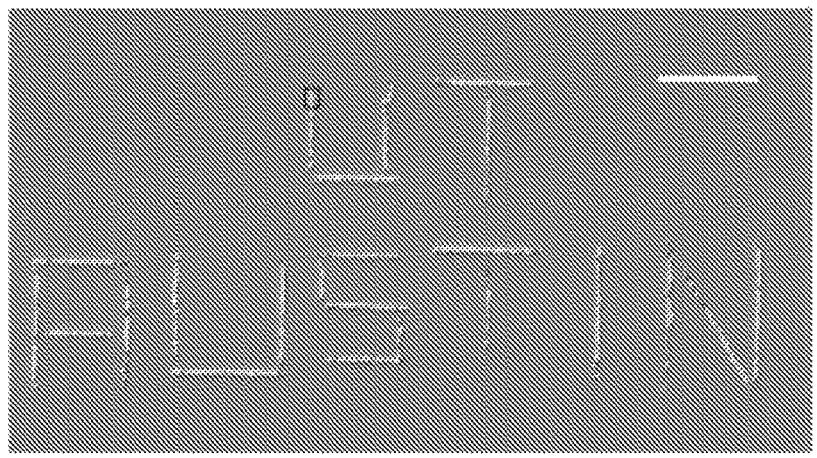
FIG. 43 shows the scanning electron micrograph (FEI Quanta 650 ESEM) of "UT AUSTIN" pattern formed with continuous writing of 60 nm polystyrene beads. Scale bar is 25 µm.
Figure 44:
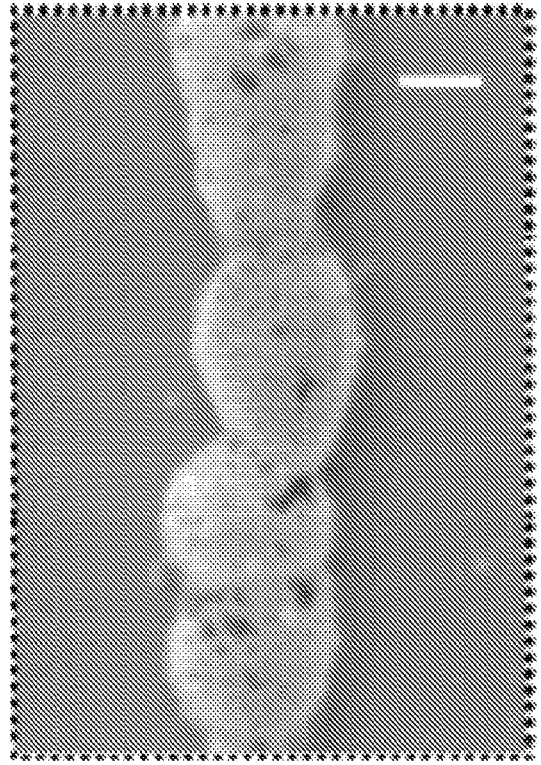
FIG. 44 shows the high-magnification scanning electron micrograph (FEI Quanta 650 ESEM) of the small segment of the "UT AUSTIN" pattern indicated in FIG. 43 formed with continuous writing of 60 nm polystyrene beads, which shows the detailed hollow structure. Scale bar is 500 nm.

In another example, FIG. 36 shows the 4×4 arrays of polystyrene beads with a diameter of 60 nm. Since the beads (60 nm) are much smaller than the microbubble, 3D hollow structures were obtained (FIG. 37). Computational fluid dynamics simulations support the formation of the 3D hollow structures (FIG. 38-FIG. 41). Moreover, the 3D hollow structure can be continuously written on the substrate, leading to hollow-ridge patterns of the beads (FIG. 42-FIG. 44) (for the continuous patterning, the 60 nm polystyrene solution was diluted with DI water at a ratio of 1:10 v/v). Such 3D hollow structures can find applications in omnidirectional optical devices, wide-angle-view imaging, and microlenses (Raut H K et al. *ACS Nano* 2015, 9, 1305-1314; Wu D et al. *Adv. Opt. Mater.* 2014, 2, 751-758; Serra F et al. *Adv. Opt. Mater.* 2015, 3, 1287-1292).

Figure 45:
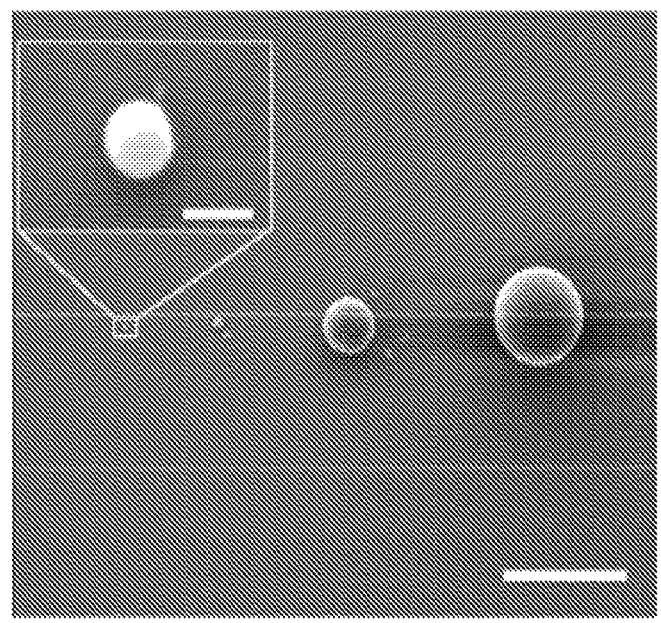
FIG. 45 shows the scanning electron micrograph (FEI Quanta 650 ESEM) of patterning of single polystyrene beads with different sizes: 540 nm, 0.96 µm, 5.31 µm, and 9.51 µm, respectively (from left to right). Scale bar is 10 µm. Scale bar in inset of is 500 nm.
Figure 46:
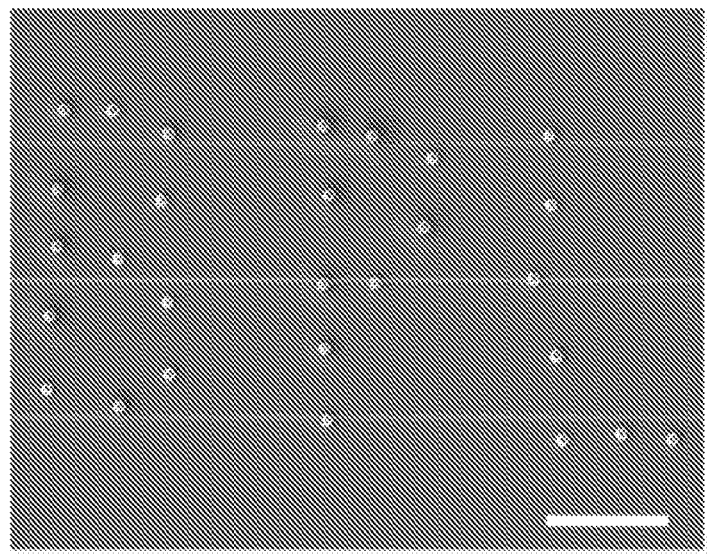
FIG. 46 shows the scanning electron micrograph (FEI Quanta 650 ESEM) of the "BPL" patterns of 0.96 µm polystyrene beads. Scale bar is 10 µm.
Figure 47:
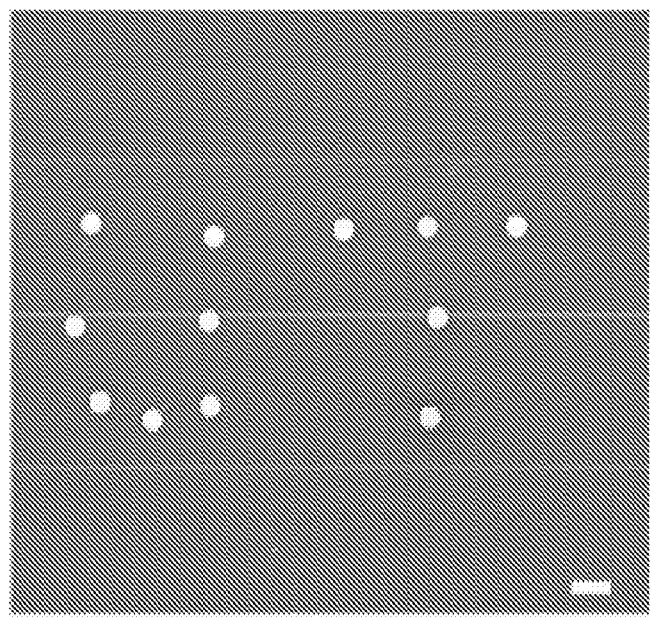
FIG. 47 shows the scanning electron micrograph (FEI Quanta 650 ESEM) of the "UT" patterns of 5.31 µm polystyrene beads. Scale bar is 10 µm.

The bubble-pen lithography resolution based on the current experimental setup was also evaluated. As shown in FIG. 45, the patterning of single polystyrene beads with sizes ranging from 540 nm to 9.51 µm was achieved. For single-particle patterning, all the particle solutions were diluted with DI water (1:10,000, v/v). Individual beads were also patterned into "bubble-pen lithography" (bead diameter: 0.96 µm) and "UT" (bead diameter: 5.31 µm) logos (FIG. 46 and FIG. 47). With the capability of patterning single beads, bubble-pen lithography can be a useful in single-particle sensing (Liu N et al. *Nat. Mater.* 2011, 10, 631-636) and single-cell analysis (Wood D K et al. *Proc. Natl. Acad. Sci.* 2010, 107, 10008-10013). The resolution of bubble-pen lithography can be improved by modifying various components of the experimental setup, for example better imaging and concentration control for nanoparticles below 100 nm.

Figure 48:
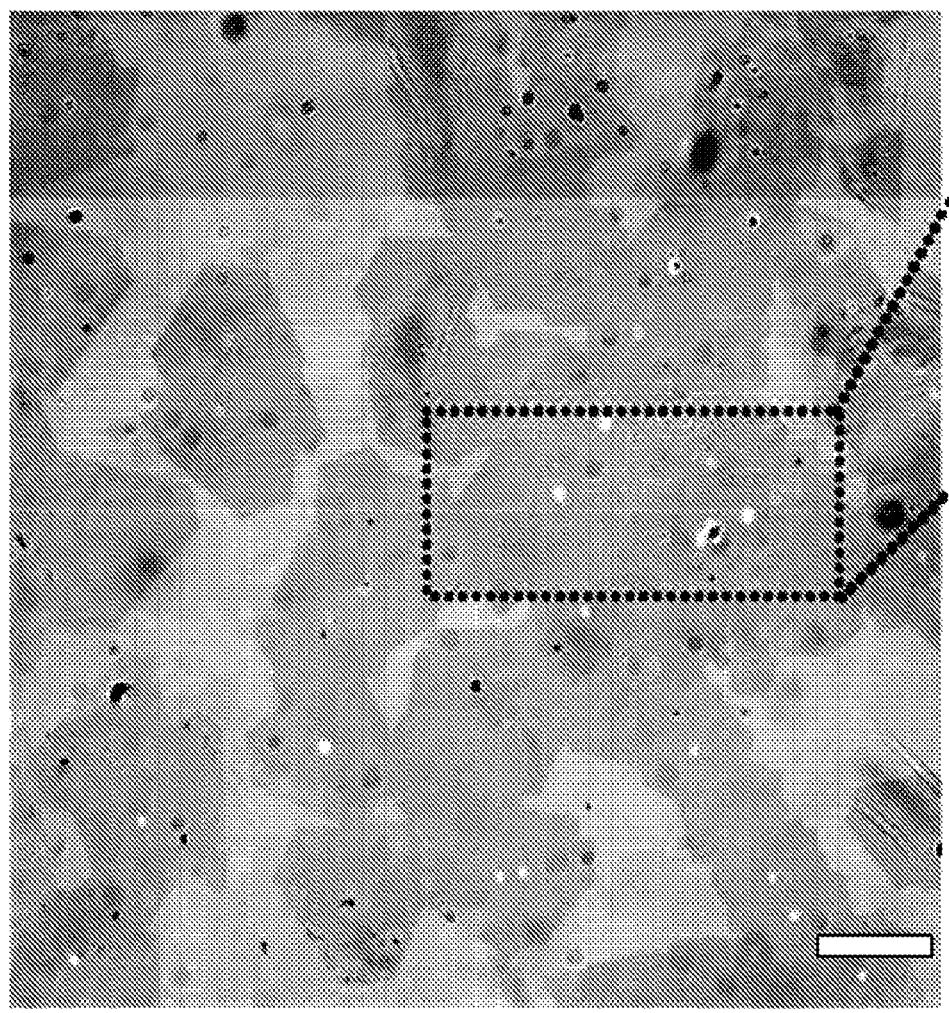
FIG. 48 shows the optical micrograph of the 2D $MoS_2$ monolayers on the gold nanoislands substrate. Scale bar: 50 µm.

Bubble-pen lithography can also be used to pattern particles on other surfaces beyond the plasmonic substrates. For example, arbitrary patterning of the polystyrene beads on a 2D atomic-layer material was achieved. For this demonstration, MoS$_2$ atomic monolayers were grown using chemical vapor deposition (CVD) and then transferred onto the gold nanoislands substrate (FIG. 48). Briefly, MoO$_3$ (15 mg) and sulfur (1 g) powder were loaded in separate alumina crucibles and heated independently using a heating tape. At a base pressure of <10 mTorr, the tube was purged with pure N$_2$ gas at 200 sccm for 4 cycles. After that, the tube was filled with N$_2$ to 1 atm pressure at 10 sccm. The furnace was heated to 850° C. for the growth of MoS$_2$ on SiO$_2$ surfaces with a heating rate of 50° C./min. The growth process lasts for 5 min. To transfer MoS$_2$ from SiO$_2$ to the gold nanoislands substrate, PMMA was spin-coated on the top of 2D monolayers. The SiO$_2$ was then etched away with sodium hydroxide solution (NaOH, 2 M, 80° C.), and the PMMA-supported MoS$_2$ was transferred to the gold nanoislands substrate. The transferred sample was stored in a desiccator and baked at 180° C. for 2 min to improve the adhesion. After the selective removal of PMMA in acetone, MoS$_2$ monolayers remain on the gold nanoislands substrate.

Figure 49:
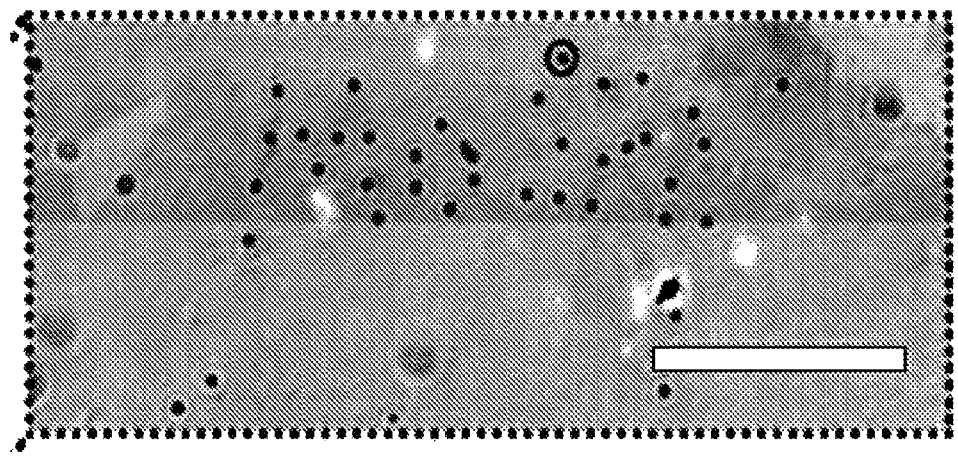
FIG. 49 shows the optical micrograph of the "$MoS_2$" patterns of individual 0.96 µm PS beads written on the 2D $MoS_2$ monolayer. Scale bar: 50 µm.
Figure 50:
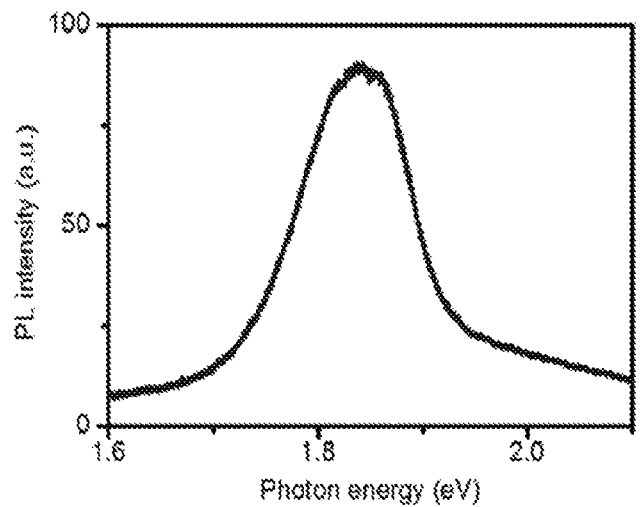
FIG. 50 shows the photoluminescence spectrum of the $MoS_2$ recorded from the regime with a single polystyrene bead, as indicated by the red circle in FIG. 49.

As illustrated in FIG. 49, the "MoS$_2$" patterns of individual polystyrene beads with a diameter of 0.96 µm were created on the MoS$_2$ monolayer using bubble-pen lithography. In FIG. 50, a photoluminescence (PL) spectrum taken from the patterned area (recorded with a Witec micro Raman spectrometer Alpha 300 system using a 532 nm laser as excitation source), as indicated by the red circle in FIG. 49, revealed that there is no damage to the 2D monolayer during patterning by bubble-pen lithography. The 2D monolayer has a sub-nanoscale thickness (6.7 Å) and a thermal conductivity of 34.5 W/mK (Yan R et al. *ACS Nano* 2014, 8, 986-993), which together make it possible to generate microbubbles on top of the 2D monolayer. In principle, bubble-pen lithography is applicable to a variety of particles and 2D materials. By synergizing the properties of 0D and 2D systems, heterostructures of micro-/nano-particles and 2D materials can exhibit functions useful for different applications. In addition, the particles can work as masks for further patterning of 2D monolayer through selective etching or deposition of new materials.

Figure 51:
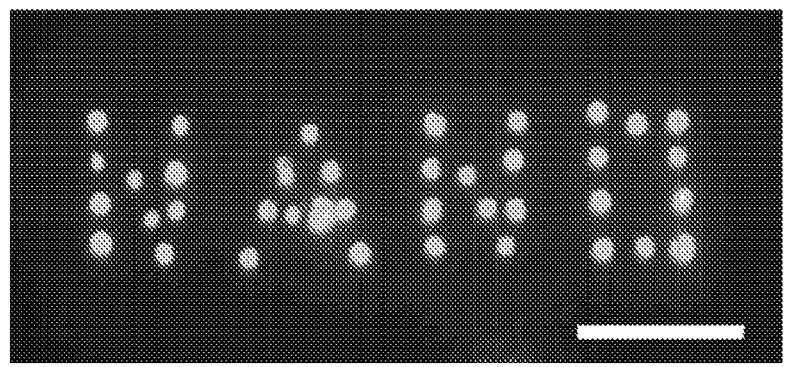
FIG. 51 shows a fluorescence image of the "NANO" patterns of 6 nm CdSe/ZnS quantum dots on the gold nanoislands. Scale bar: 50 µm.
Figure 52:
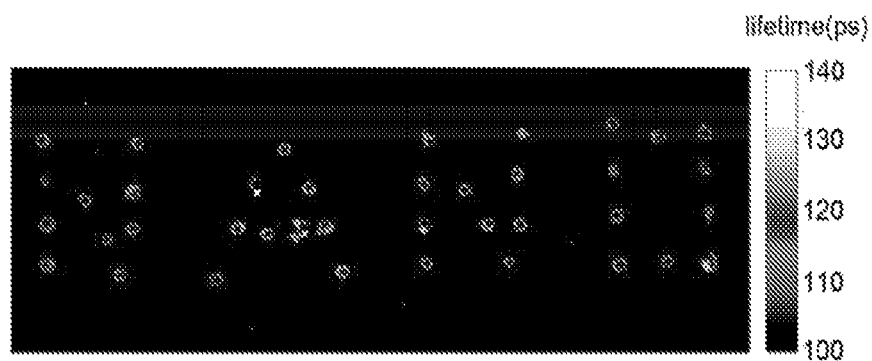
FIG. 52 shows the fluorescence lifetime image of the patterned CdSe/ZnS quantum dots as shown in FIG. 51.

To further demonstrate the versatility of bubble-pen lithography, it was used for arbitrary patterning of quantum dots, which are much smaller in size than the polystyrene beads. As an example, CdSe/ZnS core/shell quantum dots with a diameter of 6 nm were used for bubble-pen lithography. The CdSe/ZnS quantum dots were purchased from Life Technology Inc. (Qdot® 525 streptavidin conjugate). The 6 nm CdSe/ZnS core/shell quantum dots have polymer coating and biomolecules on the outer shell, leading to a total size of 15-20 nm. The quantum dots were diluted using DI water (1:30, v/v) for the patterning process As shown in FIG. 51, the "NANO" patterns of the quantum dots were created on the gold nanoislands substrate. The fluorescence lifetime of the patterned quantum dots was measured using a time-correlated single-photon counting technique (FIG. 52). The fluorescence lifetime imaging of the quantum dots was performed with time-correlated single-photon counting, which includes a femtosecond titanium: sapphire laser tuned to 800 nm (~200 fs) (Mira 900, Coherent), galvo scanning mirrors (6215H, Cambridge Tech.), and a GaAsP photomultiplier tube (PMT) (H7422PA-40, Hamamatsu) in a non-descanned detection scheme. The output current of the photomultiplier tube was amplified using a preamplifier (HFAC-26, Becker and Hickl GmbH) prior to reaching the photon counting board (SPC-150, Becker and Hickl GmbH). Fluorescence lifetimes were recorded with a 20 ps time resolution and a pixel integration time of 5 ms using an average laser power of 1 mW. Lifetime fitting was performed with the least squares method using a model of a single exponential decay convolved with a Gaussian impulse function. The resultant lifetime image was thresholded based on intensity to remove the background signals from the gold nanoislands substrate. Data points with fewer than 500 photons were removed from the fitting, and the fittings with a $\chi^2$ value less than 2 were discarded to ensure a high fitting quality.

Figure 53:
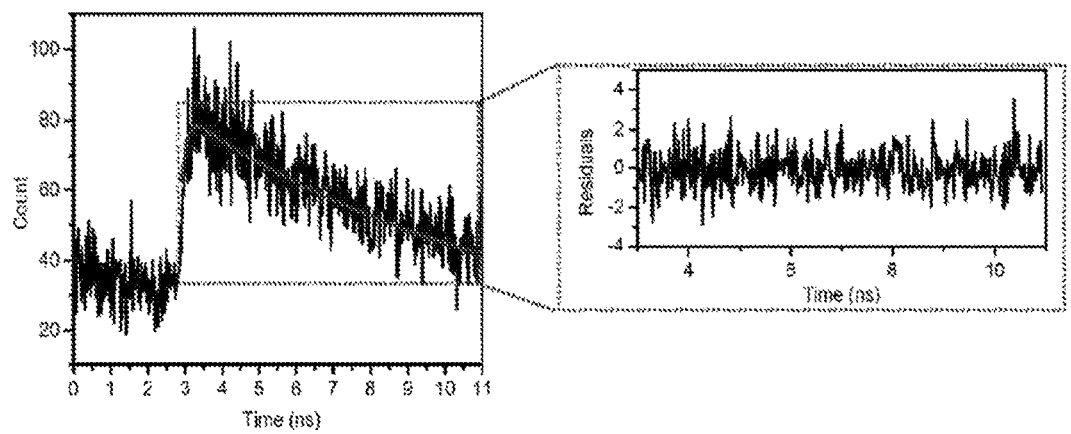
FIG. 53 shows the lifetime measurements for CdSe/ZnS quantum dots on the glass substrate. Fitting was performed with the least squares method using a model of a single exponential decay convolved with a Gaussian impulse function. Fitting residuals are shown in the right panel, indicating a good match between the model and the experimental data. The measured lifetime is 8.1 ns.
Figure 54:
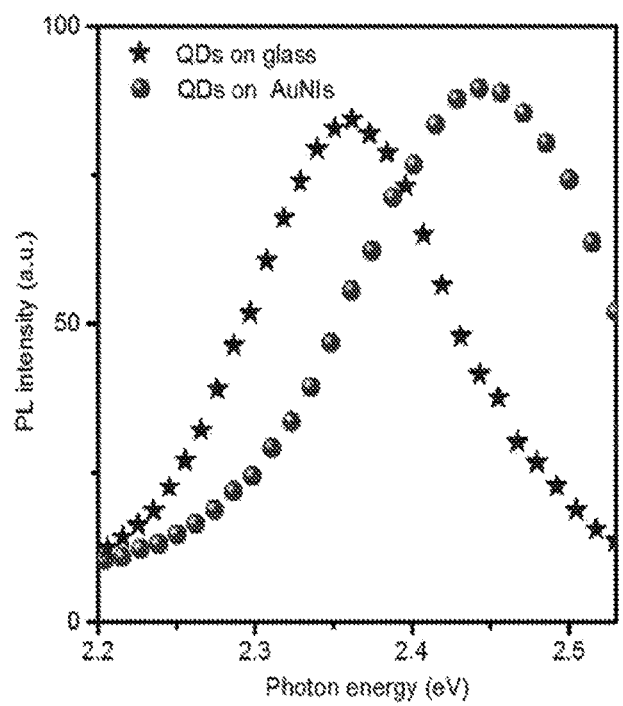
FIG. 54 shows the photoluminescence spectra of the quantum dots patterned on the plasmonic substrate and of the quantum dots on glass substrate.

An average fluorescence lifetime of ~120 ps was observed for the patterned quantum dots, which is much shorter than the 8.1 ns fluoresce lifetime of the original/unpatterned quantum dots (FIG. 53). The reduced lifetime indicates that there are strong plasmon-exciton interactions within the coupled system comprising the quantum dots and plasmonic substrate (Hoang T B et al. *Nat. Commun.* 2015, 6). The plasmon-exciton coupling is further confirmed by the photoluminescence spectra of the quantum dots (taken using a Witec micro-Raman spectrometer Alpha 300 with a 488 nm laser as excitation source), which blueshifted from 2.35 to 2.45 eV upon their patterning on the gold nanoislands (FIG. 54). With their well-controlled and highly tailorable nanostructures, the patterned quantum dots on plasmonic substrates can serve not only as platforms for the fundamental study of plasmon-exciton coupling, but can also find applications in nanophotonics and optoelectronics, such as in ultrafast light sources.

Current lithography techniques, which employ photon, electron or ion beams to induce chemical or physical reactions for micro-/nano-fabrication, have remained challenging in patterning chemically synthesized colloidal particles, which are emerging as building blocks for functional devices. Herein, a versatile lithography technique known as bubble-pen lithography for arbitrary patterning of colloidal particles on the solid-state substrates using optically controlled microbubbles was discussed. Briefly, a single laser beam generates a microbubble at the interface of colloidal suspension and a plasmonic substrate via plasmon-enhanced photothermal effects. Through combining experiments and numerical simulations, the coordinated actions of Marangoni convection, surface tension, gas pressure, and substrate adhesion were shown to contribute to the trapping and immobilization of particles in bubble-pen lithography. With the plasmon-enhanced photothermal effects on the plasmonic substrates, bubble-pen lithography can operate efficiently in a continuous-scanning mode and at low laser power. The versatility of bubble-pen lithography is reflected in its capability of writing arbitrary patterns of single and clusters of particles in 2D or 3D configurations and in its applicability to various colloidal particles and substrates beyond plasmonic nanostructures. The tunability of bubble size, substrate temperature and flow convention in bubble-pen lithography can enrich the configurations of particles in the patterns. With the low-power operation, arbitrary patterning and applicability to general colloidal particles, bubble-pen lithography will find a wide range of applications in microelectronics, nanophotonics, and nanomedicine.

The studies discussed herein exploited photothermal effects for the immobilization of particles on the substrates, which is applicable to thermoresponsive particles like polystyrene beads and CdSe/ZnS quantum dots with polymer coatings. Surface-functionalization methods can be employed to enhance the substrate-particle interactions for the immobilization of a wider range of particles, including electrostatic attraction and chemical recognition. Besides serving as a platform for fundamental research on colloidal nanoscience, the patterned particles on gold nanoislands substrates can be used as-prepared or transferred to different substrates for functional device applications. For the former, the plasmonic effects can be exploited to enhance the performance of the particles such as the shortened fluorescence lifetime of quantum dots on the gold nanoislands substrates. The capability of patterning colloidal particles on 2D materials opens up new opportunities for new functional hybrid materials and devices that benefit from the synergistic integration of 0D and 2D materials.

Example 2

Semiconductor nanomaterials exhibit strong quantum confinement effects at sizes below the Bohr radius; semiconductor materials at these sizes are also known as quantum dots (QDs). The high crystal quality and precisely controllable size contribute to the tunable absorption and emission wavelength, narrow emission bandwidth, high quantum efficiency, and stability of quantum dots. The capability of bulk solution phase synthesis of quantum dots in both aqueous and non-aqueous solvents further enhances their applicability (Yin Y D and Talapin D. *Chem Soc Rev,* 2013, 42, 2484-2487; Yu W W and Peng X G. *Angew Chem Int Edit,* 2002, 41, 2368-2371; Cassette E et al. *Adv Drug Deliver Rev,* 2013, 65, 719-731). Typical areas of application of quantum dots include light-emitting devices, information displays, photovoltaics, biosensing, nanolasers, and photodetectors. The optical performance of quantum dots can be further enhanced by placing the quantum dots in a high-quality plasmonic cavity, which can significantly improve the spontaneous emission rate by the Purcell effect and modify the emission direction by coupling the emitted photon into the directional scattering light (Gu H W et al. *J Am Chem Soc,* 2004, 126, 5664-5665). The plasmon-quantum dots hybrid system can be used, for example, in full-color displays and nanolasers.

However, the translation of quantum dots into real-life applications mentioned above relies on the capability to pattern or print quantum dots onto a solid-state substrate with predetermined locations (Lan H B and Ding Y C. *Nano Today,* 2012, 7, 94-123 Galatsis K et al. *Adv Mater,* 2010, 22, 769-778). The realization of applications in photonics and biotechnology are dependent on structures patterning of quantum dots. To this end, considerable efforts have been put into investigating various methods of quantum dot printing, with the major approaches including Langmuir-Blodgett (LB) printing, micro-transfer printing, gravure printing, inkjet printing, and electrohydrodynamic jet (E-Jet) printing. The mask-based approaches (Langmuir-Blodgett and transfer printing) can achieve high-resolution, reaching up to single quantum dot patterning capability. But, their reliance of mask fabrication and multi-step processing limit their wide-spread applicability. In contrast, ink/nozzle-based printing techniques (Inkjet and E-Jet) are direct-writing approaches which circumvent the reliance on a mask, thereby reducing the overhead cost considerably. Considerable advancements have been made to integrate these technologies with flexible substrates and achieve roll-to-roll printing (Angmo D et al. *Adv Energy Mater,* 2013, 3, 172-175). However, manufacturing complex structures at sub micrometer resolution has been challenging due to the spreading of the ink upon exposure to the substrate and post-processing time for the inks to dry. In addition to the technological capabilities, extension of a technique with haptic integration offers a complete experience with maximal flexibility. Therefore, developing a broadly applicable high-resolution, precise and intricate printing technique is needed for the widespread applications of the semiconductor quantum dots.

Herein, a microbubble is used to capture and print quantum dots in their native environment, with this method being referred to herein as bubble printing (BP). By generating and translating opto-thermally generated mesobubbles (bubbles with diameter <1 µm) on a plasmonic substrate, the suspended quantum dots can be rapidly delivered towards the air-liquid interface of the mesobubble by Marangoni convection and the quantum dots can be immobilize with precise site control. This technique circumvents a major technical challenge regarding the development of a versatile printing technique with resolution below 1 µm, which is challenging using traditional printing techniques, with typical metrics remaining above 5 µm (FIG. 55) (Bao B et al. *Small,* 2015, 11, 1649-1654). In accordance with major patterning techniques, bubble printing offers versatility of achieving complex morphologies with low material waste, high throughput (maximum scanning rate of ~$10^{-2}$ m/s), high resolution (~650 nm) and real-time configurable patterning. To demonstrate the versatility of bubble printing, haptic interfacing was achieved via a smartphone device, with any arbitrary hand drawn pattern replicated at the microscale. Further, by controlling the optical power, tunable color emission and fluorescence lifetime of the printed quantum dots is possible. The bubble printing method also enables the patterning of quantum dots on flexible substrates. With the high-resolution, high throughput, real-time reconfigurable operation, and tunability of emission color and fluorescence lifetime, bubble printing can further exploit the application of semiconductor quantum dots in nanoelectronics and nanophotonics.

In general, the water-soluble QDs used here were synthesized applying a previously reported method (Yu W W et al. *J Am Chem Soc.* 2007, 129, 2871-2879). Quantum dots (QDs) with core/shell structures were synthesized based on the literature, but the CdS shell growth temperature was adjusted to 180° C. (CdSe as the core) (Li J J et al. *J Am Chem Soc.* 2003, 125, 12567-12575). These core/shell structured quantum dots were then purified and stored in chloroform. Quantum dot concentrations were determined using the available extinction coefficients (Yu W W et al. *Chem Mater.* 2003, 15, 2854-2860; Yu W W et al. *Chem Mater* 2004, 16, 560).

Poly(maleic anhydride-alt-1-octadecene) (PMAO, $M_n$=30000-50000, Aldrich) reacted with an amino poly (ethylene glycol) methyl ether (mPEG-$NH_2$, MW 6000) in chloroform overnight (room temperature) to form an amphiphilic polymer (PMAO-PEG) (molar ratio of PMAO:PEG was 1:10).

The quantum dots and PMAO-PEG were mixed in chloroform and stirred for one hour (room temperature) (molar ratio of quantum dot:PMAO-PEG was 1:10). After that, water was added in with the same volume of the chloroform solution; chloroform was gradually removed by rotary evaporation at room temperature, and resulted in clear and colored solution of water-soluble quantum dots. An ultracentrifuge (Beckman Coulter Optima L-80XP) was used to further concentrate and purify (remove excess amphiphilic polymer) the materials (typically at 200,000~300,000 g for 1-2 hours).

Figure 56:
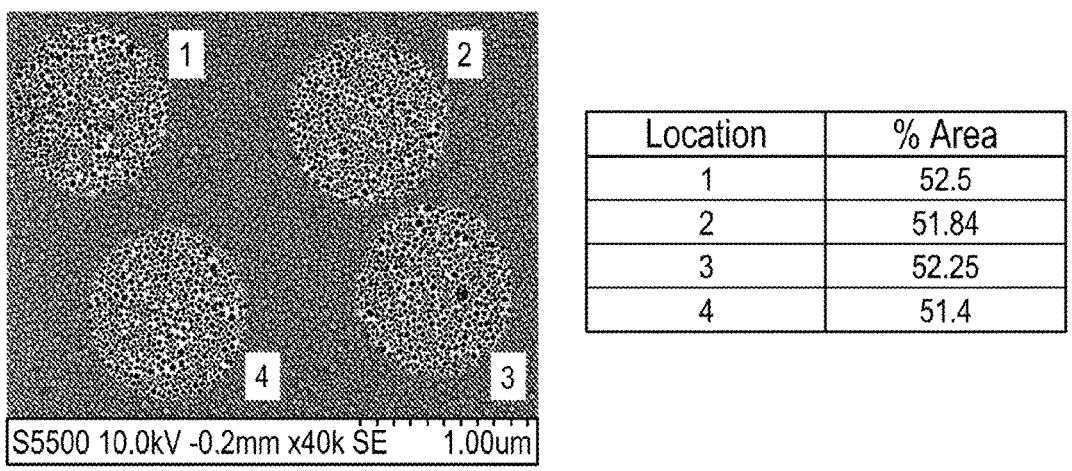
FIG. 56 is a scanning electron microscope (SEM) image of the gold nanoisland (AuNI) film used as a substrate for bubble printing (left panel). Spots of 940 nm were randomly chosen on the image, and the % area coverage of the nanoparticle were calculated as shown in the table (right panel). All spots show near-uniform Au nanoparticle coverage, with a standard deviation of 0.54%.
Figure 57:
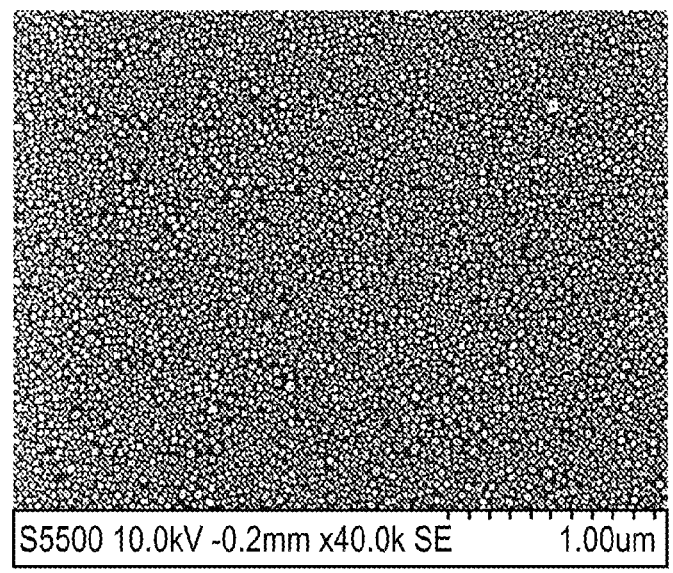
FIG. 57 is a SEM image of the gold nanoisland film being used as a substrate in bubble printing.

A gold nanoisland (AuNI) substrate was fabricated by depositing a 4 nm Au film over a glass substrate using thermal deposition (Denton Thermal evaporator) using a base pressure of 9×$10^{-6}$ torr. The sample was subsequently annealed at 550° C. for 2 hours. Scanning electron microscopy (SEM) images of the gold nanoisland film are shown in FIG. 56 and FIG. 57, which were obtained using the FBI Quanta 650 ESEM. For patterning over a flexible substrate, a polyethylene terephthalate (PET) film was initially attached over a glass slide, and a 4 nm Au film was deposited using similar parameters as stated above. The substrate was used for bubble printing directly without the annealing process.

The bubble printing (BP) process was performed by a combination of the stage translation and shutter activation/deactivation. The printing process is monitored in real-time through a charge coupled device (CCD), and illuminated with a white-light source from the top. A prior proscan scientific stage with an x-y resolution of 14 nm was used, along with a motorized flipper (ThorLabs MFF102) which acted as a shutter. The response time of the flipper is 500 ms. The stage and shutter are integrated along with the optical path and are synchronously controlled with a custom written LabView code. The code also controls the stage speed and wait times can be controlled. The stage moves along predetermined coordinates along with an on/off status of the shutter for each (x, y) location. A matlab script is used for obtaining the coordinates and the shutter status from a stencil of the desired pattern.

Figure 58:
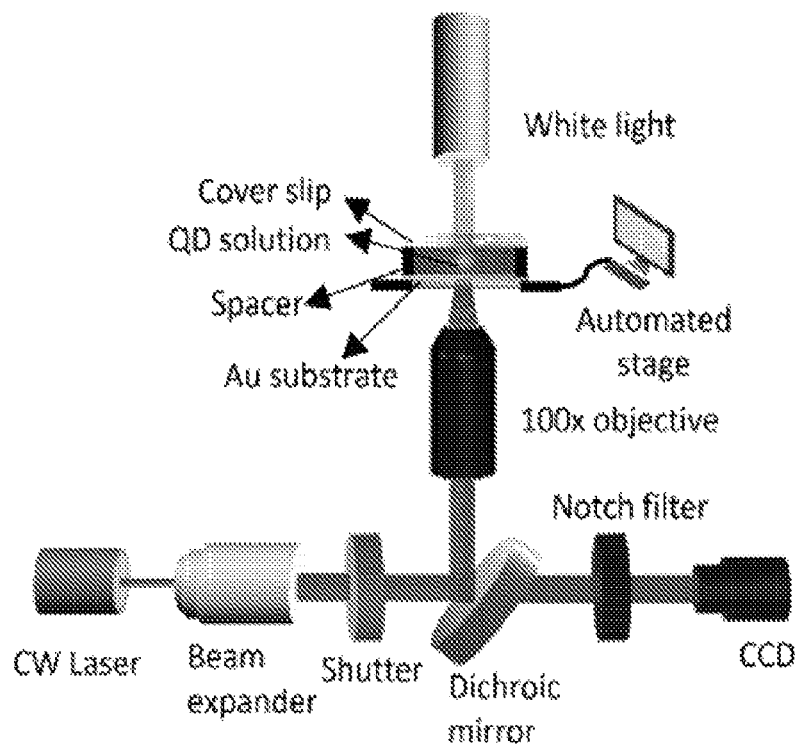
FIG. 58 is a schematic illustration of the optical setup for bubble printing.
Figure 59:
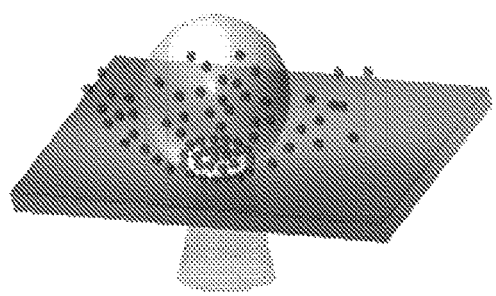
FIG. 59 is a schematic illustration showing the quantum dots being trapped towards the bubble generated on the gold nanoisland substrate, and the eventual immobilization of quantum dots on the substrate.
Figure 60:
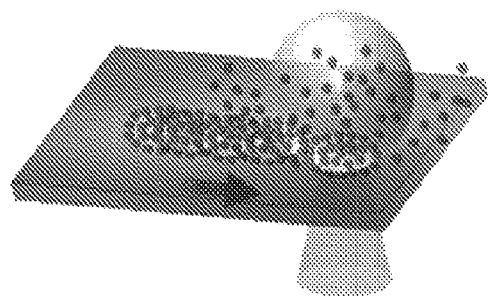
FIG. 60 is a schematic illustration of the quantum dots immobilized along the path traversed by the laser to create patterns of quantum dots on the substrate.

FIG. 58 shows the schematic of optical setup for bubble printing. The aqueous quantum dot solution is confined between a plasmonic substrate comprising gold nanoparticles (AuNP) and a glass coverslip with a 500 μm thick spacer. Upon irradiation of a focused continuous wave (CW) laser beam (532 nm) through a high magnification objective, the gold nanoparticles excited on resonance reemit the energy via nonradiative Landau damping, which results in an elevated temperature over the nanoparticle surface (FIG. 59) (Neumann O et al. *Acs Nano*, 2013, 7, 42-49; Fang Z Y et al. *Nano Lett*, 2013, 13, 1736-1742). This plasmon-enhanced photothermal heating causes the overheating and evaporation of surrounding water molecules and leads to the formation of the mesobubble, whose diameter can be controlled from sub-micron to micron regimes by tuning the optical power of the incident laser (Lin L H et al. *Nano Lett*, 2016, 16, 701-708). The temperature gradient along the bubble surface causes the Marangoni convection and therefore the suction of quantum dots towards the bubble surface by convective drag force, followed by trapping at the bubble/liquid interface with a force balance of the gas/liquid pressure difference, the drag force and the surface tension. The quantum dots are eventually immobilized on the substrate by the Van der Waals interaction between the quantum dots and the plasmonic substrate and the thermal heating. When the bubble is translated over the gold nanoisland substrate via deflection (movement of laser) or displacement (stage movement) techniques, the quantum dots are patterned along the path traversed (FIG. 60). Herein, immobilization is achieved via stage translation as it provides large-area patterning capabilities in addition to versatile patterning and high bubble stability.

Since the bubble is created based on the plasmon-enhanced optothemal heating of the plasmonic gold nanoparticles, the uniformity of the gold nanoparticles and their constituent "hot spots" (FIG. 56) ensure the bubble generation at any arbitrary location. It has been shown in numerous reports that upon focusing a laser in the vicinity of the plasmonic nanoparticles the temperature can reach up to 100° C. (Lin L H et al. *Nano Lett*, 2016, 16, 701-708; Baffou G et al. *J Phys Chem C*, 2014, 118, 4890-4898). Post bubble generation, a constant temperature increase at each instance is mandated to maintain a consistent size of the bubble generated. In general, the temperature change can be considered as a combination of increase in temperature of a nanoparticle (self-contribution due to absorption) and the external contribution from surrounding nanoparticles ($\Delta T_{total} = \Delta T_{np} + \Delta T_{ext}$). The ratio of self and external components can be estimated by considering the particle radius (R), inter-particle separation (p), full width-half maximum (fwhm) of the Gaussian beam (L) as per the following equation (Baffou G et al. *Nano*, 2013, 7, 6478-6488):

$$\frac{\Delta T_{np}}{\Delta T_{ext}} = \frac{p^2}{3LR}$$

For example, a scanning electron microscopy image of the gold nanoisland substrate shows that the nanoparticles are approximately spherical, and the average nanoparticle radius and inter-particle distance are 30 nm and 15 nm, respectively. Assuming a conservative value of 500 nm for fwhm, the temperature ratio is found to be $3\times10^{-3}$. This implies that the temperature rise is in the delocalized regime, and is a cumulative effect of particles exposed to the laser. A random area selection over the gold nanoisland (AuNI) film (FIG. 56) establishes the uniformity of gold nanoparticle distribution in terms of area coverage (σ=0.48%). The highly uniform nanoparticle density along with the delocalized photothermal conversion ensures that a constant temperature is generated throughout the substrate, thereby ensuring a uniform bubble size generation capability.

Figure 61:
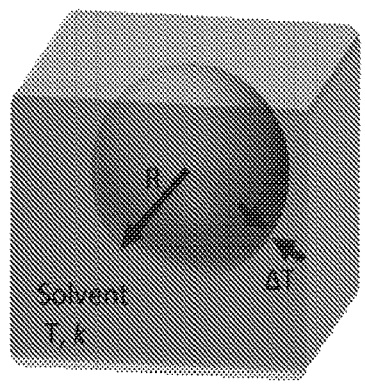
FIG. 61 is a schematic illustration showing the different parameters which affect the outward heat flux from the bubble: T, temperature; k, thermal conductivity, R, radius of the bubble; ΔT, temperature difference across bubble surface.

The premise of bubble printing is the translation of the photothermally generated bubble along pre-set trajectory and the process is governed by the steady state wherein the photothermal heat on the nanoparticles is counterbalanced by the thermal loss from the bubble to the surrounding liquid, which is at room temperature. Thermal analysis of plasmonic substrates has been conducted previously, with results indicated that the thermal energy radially propagates outwards (Baffou G et al. *Acs Nano*, 2010, 4, 709-716; Liu X M et al. *Sci Rep-Uk*, 2015, 5, 18515). Treating the bubble as a sphere, the outward heat flux from the bubble can be estimated using Fourier's law:

$$\frac{dQ}{dT} = 4\pi k R^2 \partial_r T$$

wherein Q is the heat power of the incident laser (J), k is the thermal conductivity of water ($Js^{-1}\,m^{-1}K^{-1}$), R is the radius of the bubble, T is the temperature, and $\partial_r T$ is the temperature gradient at the edge of the bubble. By assuming $$\partial_r T \approx \frac{\Delta T}{R},$$

where $\Delta T$ is the temperature difference across the bubble surface (FIG. 61), the equation becomes:

$$\frac{dQ}{dT} = 4\pi k R \Delta T$$

With the assumption that temperature difference $\Delta T$ remains the same under similar illumination conditions, the steady state thermal loss is proportional to R (Lohse D and Zhang X H. *Rev Mod Phys*, 2015, 87, 981-1035). In other words, a smaller bubble can retain the steady state for a longer period due to lower thermal loss. In addition to the lower heat loss, minimal air concentration within the bubble aids in maintaining the stability of the mesobubble (bubble radius <1 μm) as it traverses along the laser path with the shutter open. A highly focused laser beam and a plasmonic substrate with uniform and high-density gold nanoparticles effectively reduces the size of the generated bubble for stable bubble printing of quantum dots.

Figure 62:
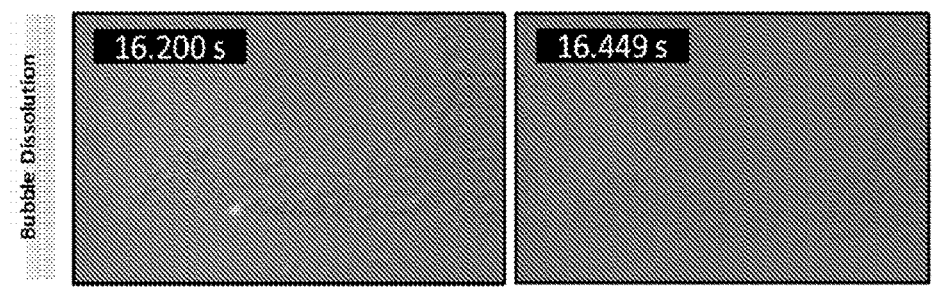
FIG. 62 shows the bubble dissolution process was analyzed by taking the video frames. The time taken for a bubble to dissolve completely was ~250 ms, which is obtained by subtracting the time stamps of the two frames. The video was taken at a frame rate of 50 frames/sec.

Herein, colloidal CdSe quantum dots encapsulated with an amphiphilic coating and dispersed in an aqueous medium were used for the bubble printing methods. Various quantum dots with an emission color in the red, yellow, and green regions were used by adding ~50 μl droplets of the quantum dots over the gold nanoisland substrate. The mesobubble dissolution (upon laser closure) time calculation via analysis of the video frames was found to be in the range of 250-300 ms. Due to the sub-micron bubble size, the concentration of air molecules within the bubble is limited, and the gas within the bubble is mostly composed of water vapor. This ensures fast disappearance of the bubble (FIG. 62), unlike the situation of air bubbles which can last from few seconds to hours (Baffou G et al. *J Phys Chem C,* 2014, 118, 4890-4898). The quick transition between the on-off state and vice versa of the bubble is necessary for high-speed patterning.

Figure 63:
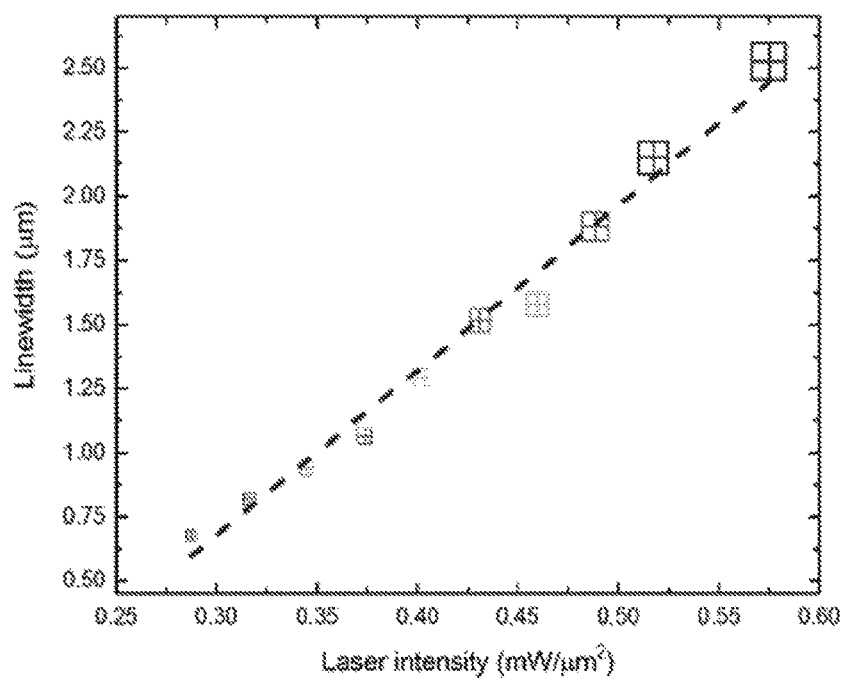
FIG. 63 is a plot of the linewidth vs incident laser intensity. The linear fit shows the capability to tune the patterning dimensions on demand.
Figure 64:
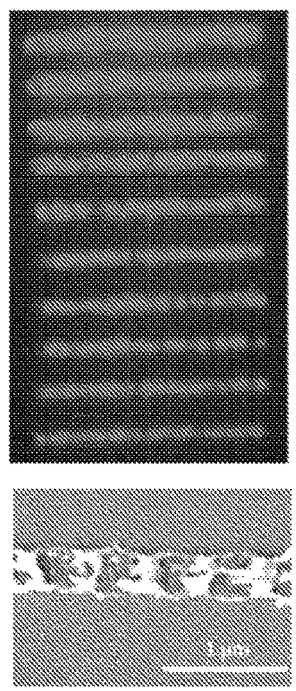
FIG. 64 is the merged fluorescence image of the plot in FIG. 63 demonstrating the linewidth variation in response of changing incident laser power (top panel). The SEM demonstrating the patterned quantum dots (QDs) with a linewidth of 680 nm (bottom panel). The gold nanoisland substrate is visible underneath the quantum dots (bottom panel).
Figure 65:
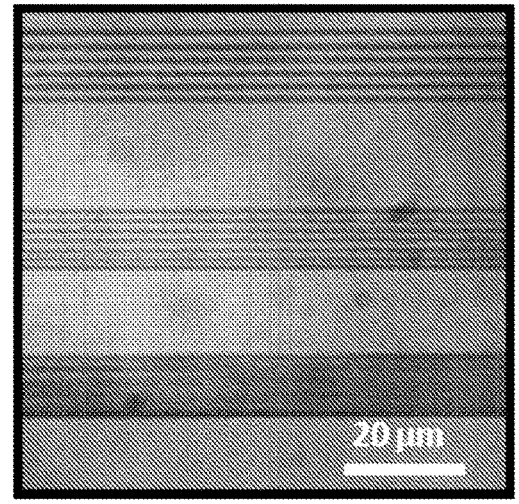
FIG. 65 shows the large area patterning of quantum dots: 200×20 µm rectangles created using bubble printing (BP) with various line spacing. The line spacing is 1 µm, 1.5 µm, and 2 µm (bottom to top). The increase in line spacing results in a decrease in density of quantum dots, which manifests as a reduction in the fluorescence counts.
Figure 66:
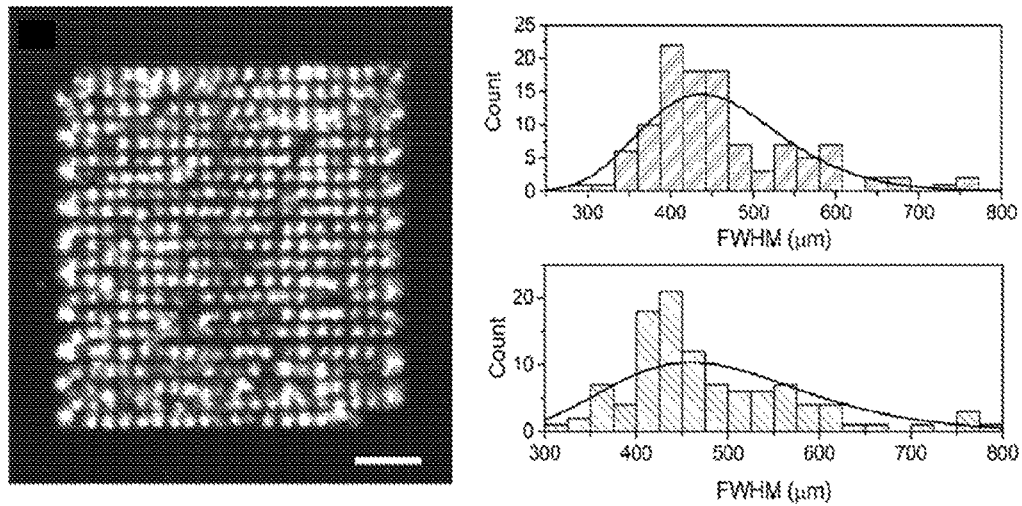
FIG. 66 is the high-resolution two-photon fluorescence image which resemble individual pixels. The dimension of each spot was calculated from the image, along both the x-axis and y-axis. The width of each pixel is obtained by calculation of the full width-half max (FWHM) of the spots, and plotting the histogram. The mean of the distribution is obtained via Gaussian fit is 450 nm. The pixelated image is observed due to the crowding of quantum dots at edge of the bubble.

Precise control over the linewidth of the quantum dot pattern can be an important parameter for advanced applications. For continuous patterning, the relationship between the incident laser intensity and the resultant pattern linewidth was examined (FIG. 63). With an increase in the optical power, the resultant bubble size increases owing to a higher amount of vapor generation. A linear regression line was obtained from the plot of pattern linewidth and the incident laser power, thus demonstrating the ease of modulating the resultant patterns. The lowest linewidth of <700 nm (FIG. 64) was observed at an incident power intensity of 0.28 mW/$\mu$m$^2$, with the upper limit of the linewidth reaching ~3 $\mu$m. Further increasing the power causes the coalescence of adjacent bubbles, thereby creating larger bubbles which have longer lifetime, and are not suitable for bubble printing. Increasing the power changes the morphology from scalloped lines to lines with uneven linewidth, eventually leading to individual bubble geometry. FIG. 65 shows a high magnification bright field image of large area rectangles fabricated via raster scanning and depicts the tunability of the quantum dot pattern density via varied line spacing (1 $\mu$m, 1.5 $\mu$m, and 2 $\mu$m). Further, by utilizing a step size of 1 $\mu$m and wait time of 500 ms at each step, crowding of the quantum dots at the edge of each bubble can be achieved. This results in an image resembling individual pixels, with a full width—half max of 400 nm pixel size as observed under a high-resolution two-photon fluorescence microscope (FIG. 66). A Zeiss LSM 710 microscope with was used for wide-field fluorescence imaging. Unless mentioned otherwise, the imaging was performed with a 405 nm excitation source and without any emission filters, with the composite images generated via wavelength dependent coloring feature within the Zeiss ZEN software.

Figure 67:
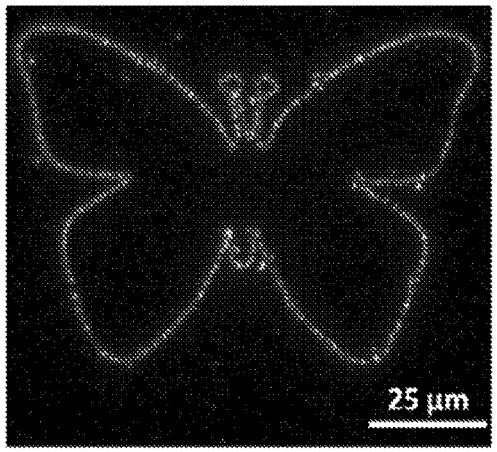
FIG. 67 is an image of bubble printing along a contour via translation of the stage along the pattern of a butterfly. The linewidth is 1 µm. The scale bar is 25 µm.
Figure 68:
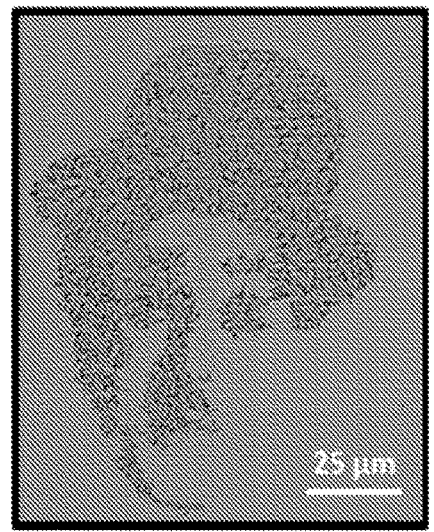
FIG. 68 is a bright field image of a pattern of quantum dots patterned via raster scanning using a stencil resembling Charlie Chaplin. The overall size is 120 µm×90 µm with 1 µm line-space. The scale bar is 25 µm.
Figure 69:
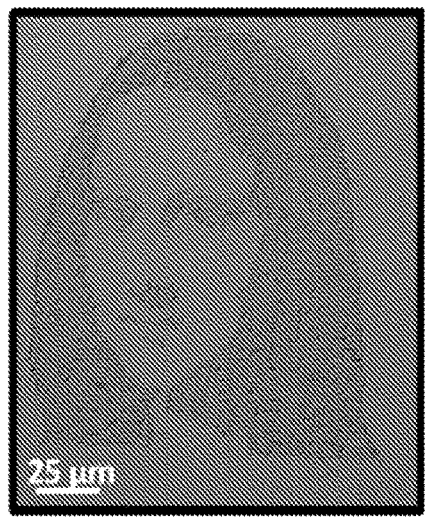
FIG. 69 is a bright field image of Mona Lisa stencil printed with red quantum dots using a raster scanning approach. The size of the complete image is 150 µm×90 µm. The scale bar is 25 µm.
Figure 70:
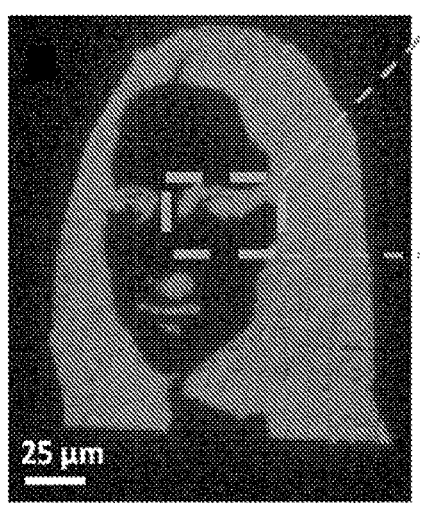
FIG. 70 is a fluorescence image of Mona Lisa stencil printed with red quantum dots using a raster scanning approach. The size of the complete image is 150 µm×90 µm. The scale bar is 25 µm.
Figure 71:
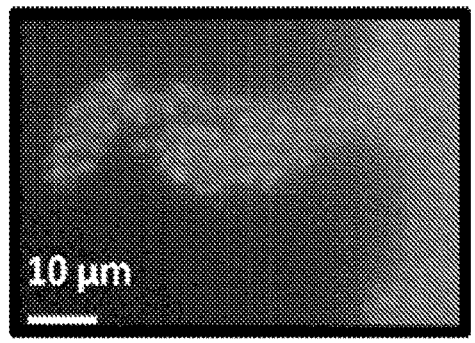
FIG. 71 is a magnified fluorescence image of the area indicated in FIG. 70 depicting the high-resolution patterning capability of bubble printing. The scale bar is 10 µm.
Figure 72:
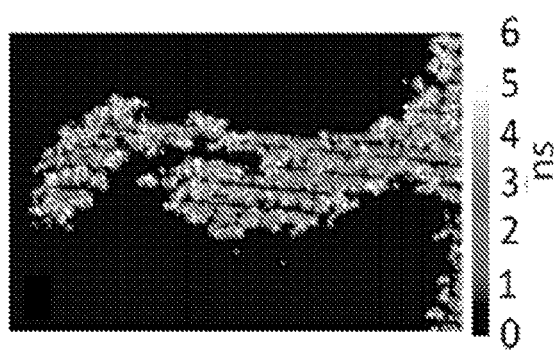
FIG. 72 is the fluorescence lifetime imaging of the quantum dots in FIG. 71 showing high density uniform patterning capability.

Following the process parameter optimization, the versatility of bubble printing was examined Initially, the quantum dots were patterned along a contour by translation of the stage post bubble initiation. FIG. 67 shows the microscale bubble printing patterning in the shape of a butterfly using red quantum dots. It is worth noting the head of the butterfly which involves closely spaced circles ~8 $\mu$m diameter, and is precisely patterned via bubble printing without any spreading, bubble coalescence or distortions (FIG. 67). With rapid dissolution and generation time of the mesobubble, it is also possible to create complicated and intricate patterns at high resolution and speed. FIG. 68 and FIG. 69 show high resolution intricate patterning of red quantum dots into stencils resembling Charlie Chaplin and Mona Lisa, respectively, with dimension of 120 $\mu$m×90 $\mu$m and 150 $\mu$m×90 $\mu$m, respectively. The optical activity of the quantum dots were not significantly affected by the patterning, which is evident from the fluorescence image in FIG. 70 taken under the TRITC channel A magnified image in FIG. 71 demonstrates the defining strength of bubble printing wherein a 1 $\mu$m gap between adjacent structures (eyebrow and eye) can be realized. To alleviate concerns of fluorescence image saturation, a fluorescence lifetime image (FLIM) of the same region is shown in FIG. 72, and it clearly demonstrates uniform deposition of quantum dots along the pattern.

The fluorescence lifetime imaging of the quantum dots was done via time-correlated single photon counting (TCSPC), with a femtosecond titanium:sapphire laser tuned to 800 nm (~200 fs) (Mira 900, Coherent), galvo scanning mirrors (6215H, Cambridge Tech.), and a GaAsP photomultiplier tube (PMT) (H7422PA-40, Hamamatsu) in nondescanned detection scheme. The output current of the PMT was amplified using a preamplifier with 2 GHz cutoff (HFAC-26, Becker and Hickl GmbH). The amplified pulses from the PMTs were sent to the TCSPC module (SPC-150, Becker and Hickl GmbH). The objective was a silicone oil immersion lens with NA of 1.3 (UPLSAPO60X, Olympus). Using an average laser power of 1 mW, fluorescence lifetimes were recorded with a 20 ps time resolution and a pixel integration time of 5 ms. The lifetime fitting was done with the least-squares method using a model of a single exponential decay convolved with a Gaussian impulse function. The resultant lifetime image was threshold-based on intensity to remove the background signals from the gold nanoisland substrate. In order to ensure a high fitting quality, data points with less than 500 photons were removed from the fitting, and the fittings with $\chi^2$ value less than 2 were discarded.

Figure 73:
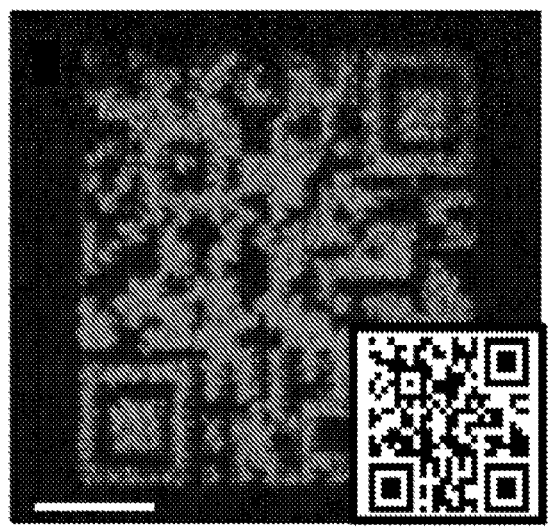
FIG. 73 shows the fabrication of a micro QR code with blue emission printed via raster scanning and a size of 80 µm×80 µm. The scale bar is 25 µm.

Further, the capability of bubble printing to fabricate of functional luminescent devices in the area of anti-counterfeiting technology is demonstrated (Bao B et al. *Small,* 2015, 11, 1649-1654). Specifically, the fabrication of a high resolution microscale QR code is desirable for containing the forging of IC chips (Markman A et al. *Ieee Photonics J,* 2014, 6, 6800609). Using bubble printing, a microscale QR code of 80 $\mu$m×80 $\mu$m was fabricated with blue emission (FIG. 73). The complicated QR code was achieved by performing a raster scan of the laser in conjunction with a shutter to determine an on/off state of printing.

Figure 74:
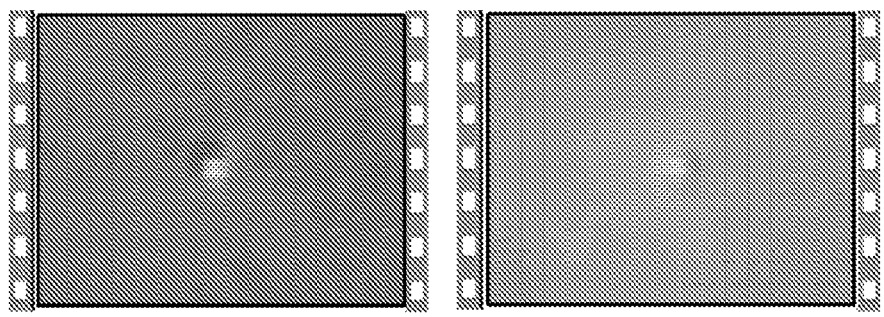
FIG. 74 is an image of bubbles generated in QD621 and QD530 taken using the CCD. The bubble generation is a consequence of the photothermal heating of the gold nanoisland substrate.
Figure 75:
FIG. 75 is a bright field image of the green quantum dots patterned as Mona Lisa with 1 µm line spacing at a high stage speed of $10^{-2}$ m/s. The patterning results in near-uniform deposition over large area, although concentration of quantum dots occur at the edges where the stage resides longer due to the constraints of the shutter.
Figure 76:
FIG. 76 is a bright field image of the large area patterning of Charlie Chaplin was achieved with a dimension of 100×150 µm.
Figure 77:
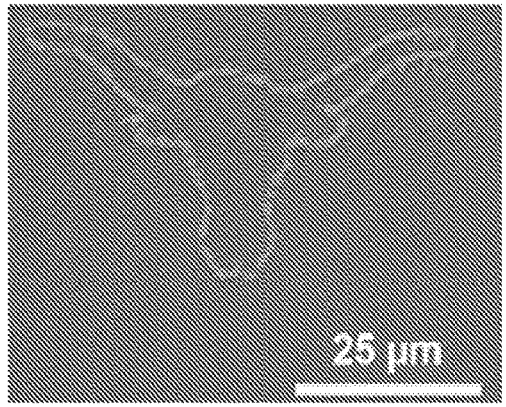
FIG. 77 is a bright field image of the contour of longhorn with an overall area of 60×60 µm².
Figure 78:
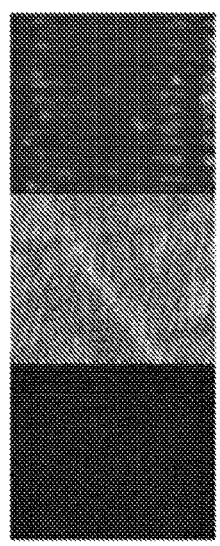
FIG. 78 shows quantum dots with emission in red, yellow and blue patterned using bubble printing. The corresponding CIE 1931 coordinates based on the emission peaks of 621 nm, 591 nm, and 480 nm are shown.
Figure 78:
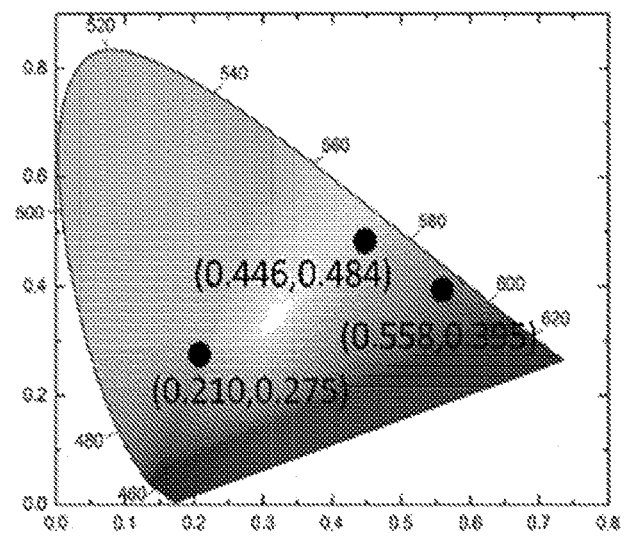
Figure 79:
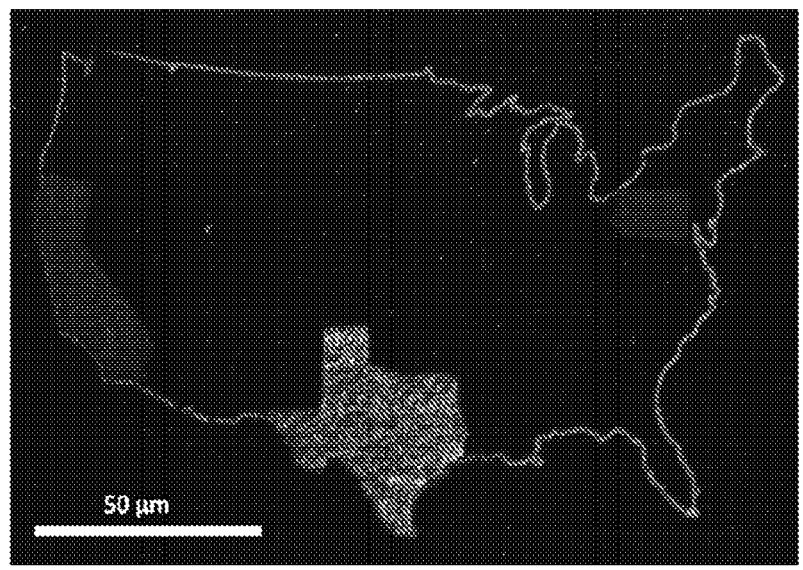
FIG. 79 shows the integration of multiple quantum dots on a single substrate using multi step bubble printing shown via printing of a map of the United States of America map with the states of Texas, California, and Pennsylvania printed with varied emission. The size of the image is 120 µm×200 µm, and each state is fabricated via raster scanning with 1 µm line-space.

Since the patterning process is primarily mediated by Maragoni convection and subsequent van der Waals interaction, the bubble printing technique can also pattern quantum dots with different sizes and materials, which is critical for the fabrication of on-chip quantum dots devices. Specifically, the patterning of quantum dots with varied emission color onto the plasmonic substrate was demonstrated. The immobilization mechanism remains the same irrespective of the quantum dots being printed, and utilizes bubbles generated within various quantum dotes (FIG. 74). The image of Mona Lisa with 1 $\mu$m line spacing was replicated with yellow emission and high stage speed (10$^{-2}$ m/s), and is shown in FIG. 75. Similarly, large area patterning of Charlie Chaplan and a longhorn are shown in FIG. 76 and FIG. 77, respectively. FIG. 78 shows the high density bubble printing of quantum dots with emission ranging from red to blue, revealing the opportunities of full-color display (Kim B H et al. *Acs Nano,* 2016, 10, 4920-4925). The right panel in FIG. 78 shows the corresponding CIE 1931 coordinates for the patterned quantum dots based on their emission peaks. To verify this concept, individual red/green/blue quantum dots were regioselectively printed onto a single substrate. FIG. 79 shows the fluorescence image (405 nm excitation) of a map of the United States of America fabricated along with the states of Texas, California and Pennsylvania printed using varied emission quantum dots at the micro-scale, with an overall dimension of 120 $\mu$m×200 $\mu$m. This is achieved via a multi-step printing process with the desired quantum dot emission solution present in each step over the plasmonic substrate. The multi-step patterning is aided by three cross-markers created via bubble printing for alignment, and a rigorous washing step with isopropyl alcohol and water between each step to remove loosely adsorbed quantum dots on the substrate. The strong adhesion of the printed quantum dots over the substrates ensures that the patterned quantum dots are not ejected from the surface. For instance, the quantum dots are not transferred even after transfer trials to a very sticky polydimethyl siloxane (PDMS) substrate (30:1 dilution).

Figure 80:
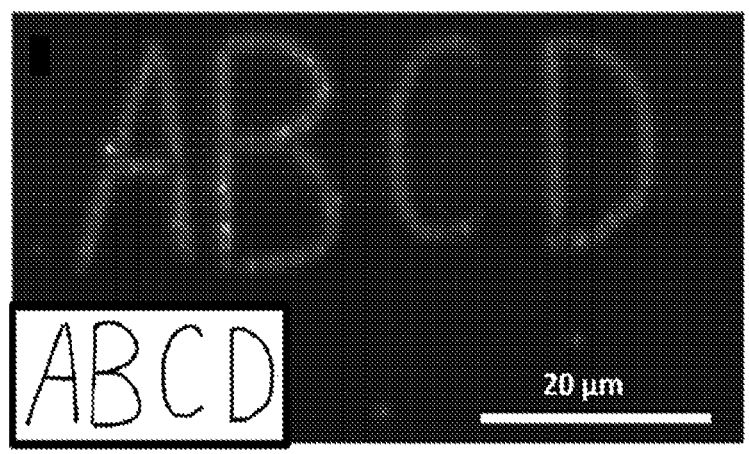
FIG. 80 is a fluorescence image of bubble printed pattern of alphabets which was drawn on a smart phone. The inset is the screenshot of the smartphone with the written symbols.
Figure 81:
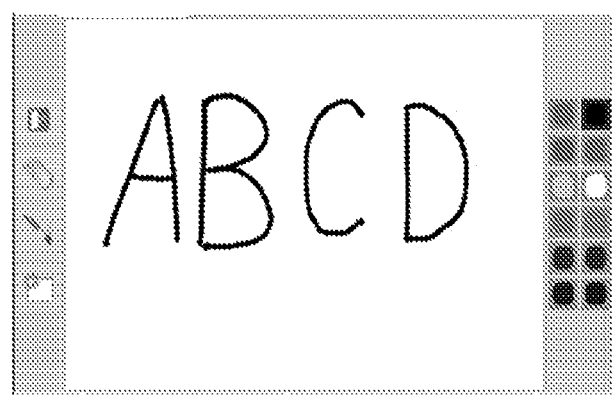
FIG. 81 is a screenshot from the smartphone application depicting hand written alphabets.

The arbitrary patterning capability of this technique is evidenced by the haptic interfacing of bubble printing using a smartphone device. A custom built application registers the movement of a user's fingers over the screen, and outputs the details for the stage translation and shutter, which are subsequently imported into the LabView code. The application was built using Java. The user can draw any arbitrary pattern of choice, with the app registering the coordinates as the hand traverses along the screen. The data is output as a [n×3] matrix, with the first two columns corresponding to the (x, y) coordinates, and the third column provided a 1/0 condition for the shutter. The last column is decided based on a touch/no-touch event on the app. The output file is then imported into the LabView code with appropriate scaling factors (~30×) to realize the actual fabrication. FIG. 80 demonstrates haptic interfaced printing of arbitrary hand drawn patterns of alphabets (with the complete phone screenshot being shown in FIG. 81).

Figure 82:
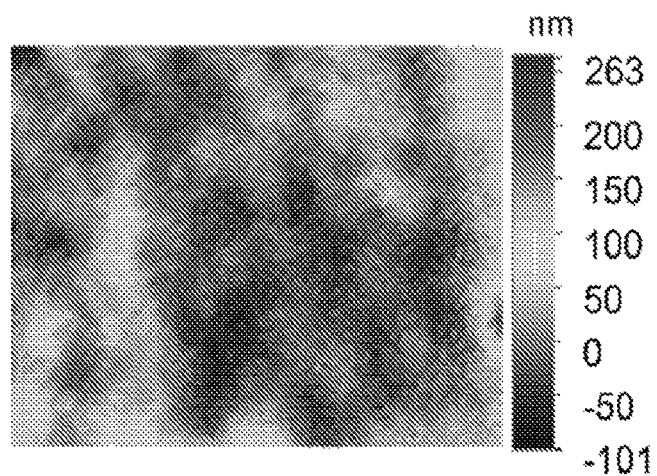
FIG. 82 is an optical profilometer image (Wyco 9100) of the polyethylene terephthalate (PET) film showing an rms roughness of 35 nm.
Figure 83:
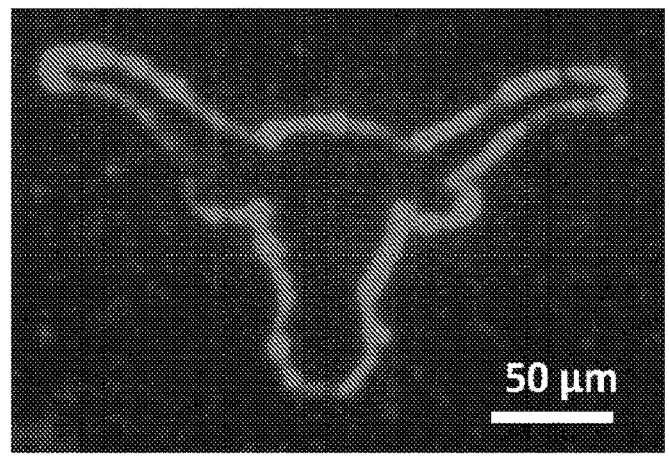
FIG. 83 is a fluorescence image of the longhorn pattern printed with red quantum dots over a PET film.
Figure 84:
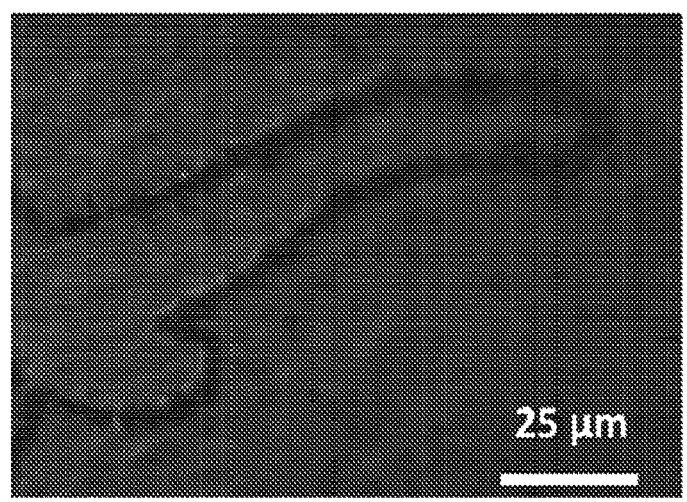
FIG. 84 is a bright field image of the printed quantum dots with the PET film in the bent state. The high adhesion of quantum dots to the substrate ensures integrity of the pattern is maintained post bending.

In addition to being compatible with rigid substrates, superior printing techniques should enable fabrication over flexible and bendable plastic films. A thin film of Au (4 nm) was deposited over a flexible polyethylene terephthalate (PET) film, and utilized directly for bubble printing. The increase in root mean square (RMS) roughness to 35 nm (FIG. 82) is not a major barrier towards bubble generation, with numerous reports studying bubble generation considering RMS values above 1 μm as rough surfaces (McHale J P and Garimella S V. *Int J Multiphas Flow*, 2010, 36, 249-260). FIG. 83 shows the longhorn symbol created via bubble printing on a PET film using red quantum dots. Further, a magnified bright field image of the same pattern is shown with the plastic film under bent condition, and it clearly exhibits structural integrity even in the bent state (FIG. 84). Consecutive bend and release steps (20 instances) as shown in FIG. 85 and FIG. 86, yielded no significant changes in the structural and emissive properties. In addition, the printed quantum dots were able to withstand both uniform and non-uniform bending owing to their high adhesion.

Figure 88:
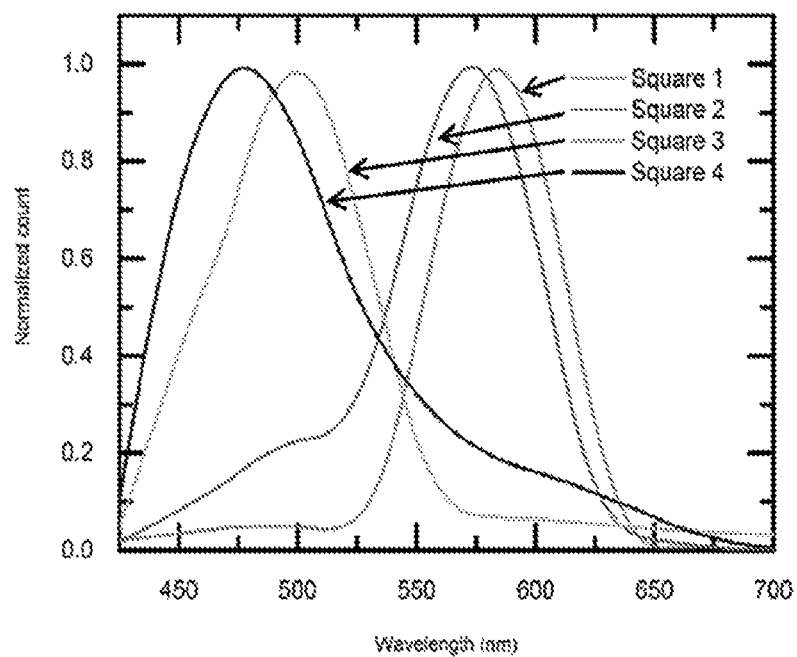
FIG. 88 shows the fluorescence spectrum corresponding to the squares in FIG. 87 demonstrating gradual blue-shift.

Besides the translation of quantum dots from aqueous solvent onto a solid-state substrate, surface modification of the patterned quantum dots was achieved simultaneously by controlling the optical power, which provides rational optimization the of emission properties. By employing a relatively elevated laser power (above 0.5 mW/μm$^2$) and varied stage speed, the emission of yellow quantum dots were altered to yield blue emission. FIG. 87 reveals an emission blue shift of a square of originally yellow quantum dots (20×20 μm$^2$) structures dependent on the printing parameters. The laser exposure time over quantum dots increases along FIG. 87, with the blue emission square fabricated at a line spacing of 0.5 μm resulting in a double exposure due to raster scanning. The continued oxidation also caused the spectrum to broaden with time (square 4) (Shcherbatyuk G V et al. *J Appl Phys*, 2011, 110, 053518). The laser exposure time at a given location quadruples from the initial to the final square. The higher incident laser power in conjunction with longer exposure time results in the photo-induced oxidation of the patterned quantum dots, which causes a spectral shift to shorter wavelengths (Kimura J et al. *J Phys Chem B*, 2004, 108, 13258-13264; Shcherbatyuk G V et al. *J Appl Phys*, 2011, 110, 053518). The formation of an oxide layer reduces the effective diameter of the quantum dots, thereby increasing the quantum confinement and, in turn, the bandgap. The oxidation effect is evident in the spectrum of square 2 wherein a small shoulder starts appearing at ~525 nm (FIG. 88). As shown in FIG. 88, the peak wavelength is tuned from 591 nm to 475 nm. The wide range of emission wavelengths obtained via continued oxidation can be attractive for applications in full-color display and on-chip FRET sensors (Medintz I L et al. *Nat Mater*, 2005, 4, 435-446).

Figure 89:
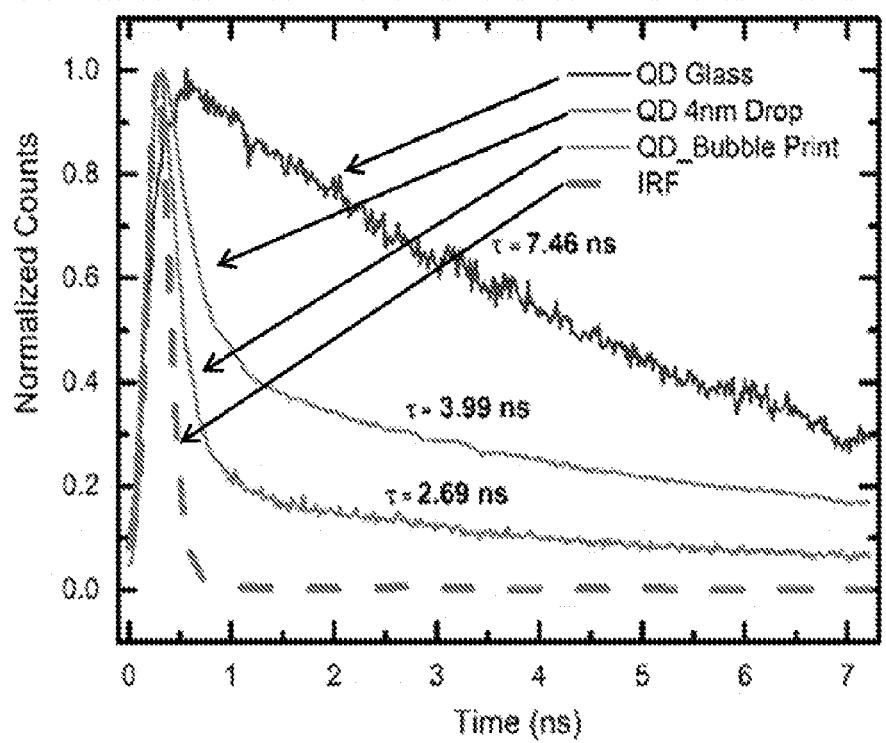
FIG. 89 shows the time correlated fluorescence of red quantum dots over (i) pure glass, (ii) drop casted over gold nanoisland film, and (iii) printed via bubble printing. The lifetime decreases from 7.46 ns under control condition to 2.69 ns when printed using bubble printing.
Figure 90:
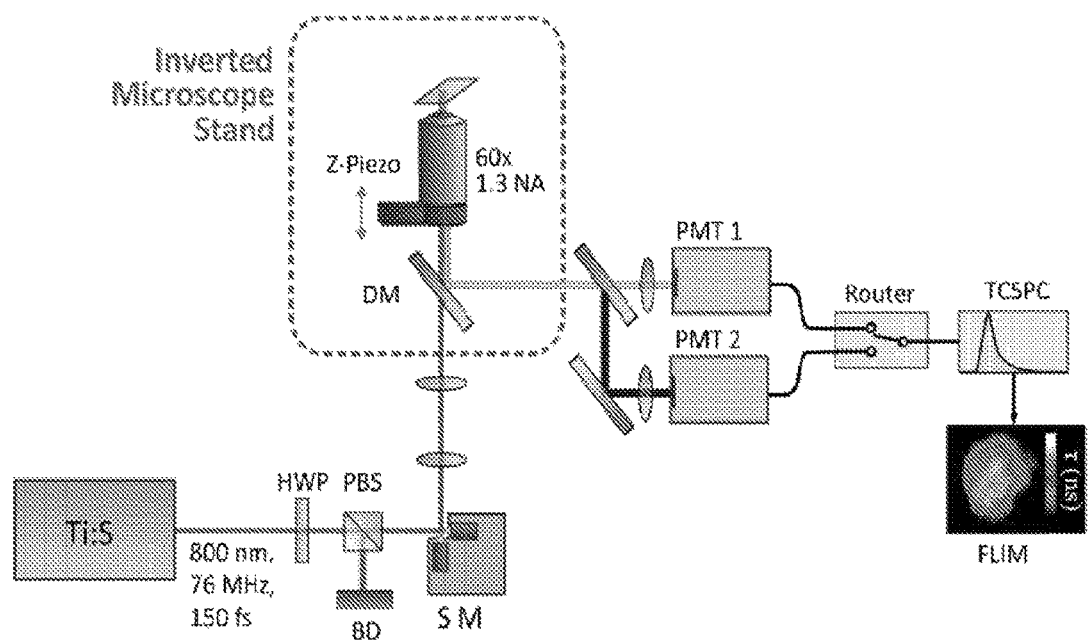
FIG. 90 is a schematic illustration of the optical setup used for fluorescence lifetime imaging (FLIM). The various abbreviations include: PBS: Polarizing beam splitter, BD: Beam dump, SM: Scanning mirrors, DM: Dichroic mirror, PMT: Photomuitiplier tube, TCPSC: Time correlated single photon counting
Figure 91:
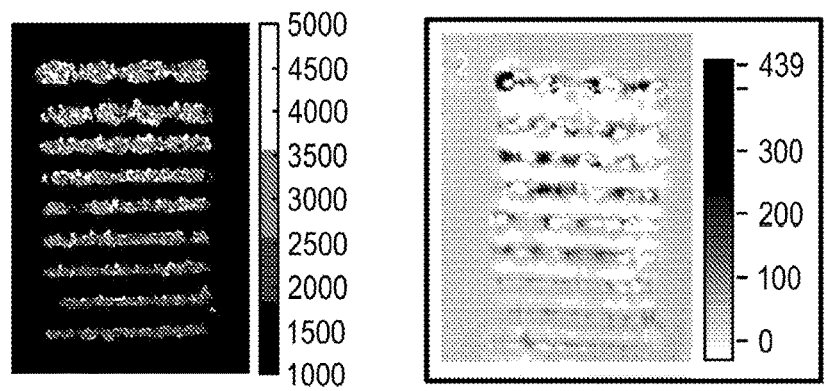
FIG. 91 is a fluorescence lifetime imaging (FLIM) image of the patterned quantum dots with increasing power. The morphology changes with increase in the patterning parameters, with the height increasing from 80 nm to 440 nm. This alters the coupling intensity between the quantum dots and underlying plasmonic substrate.
Figure 91:
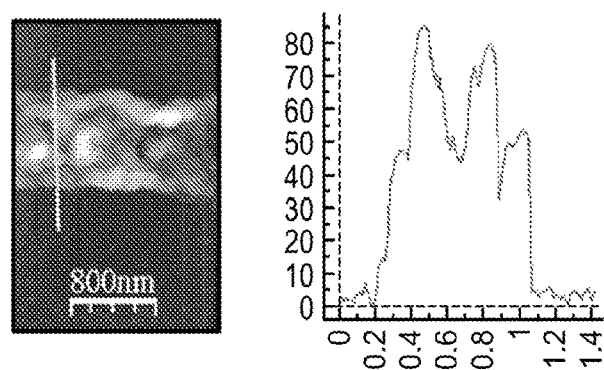
Figure 92:
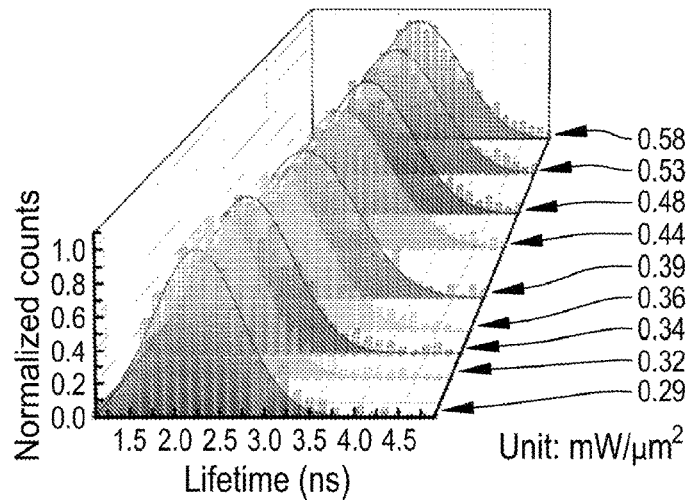
FIG. 92 shows the lifetime modification dependent on the intensity of the laser used for bubble printing. The histogram is obtained from the pixels within the FLIM image and a Gaussian fit performed at each power. The mean lifetime increases from 2.256 ns to 2.286 ns.
Figure 93:
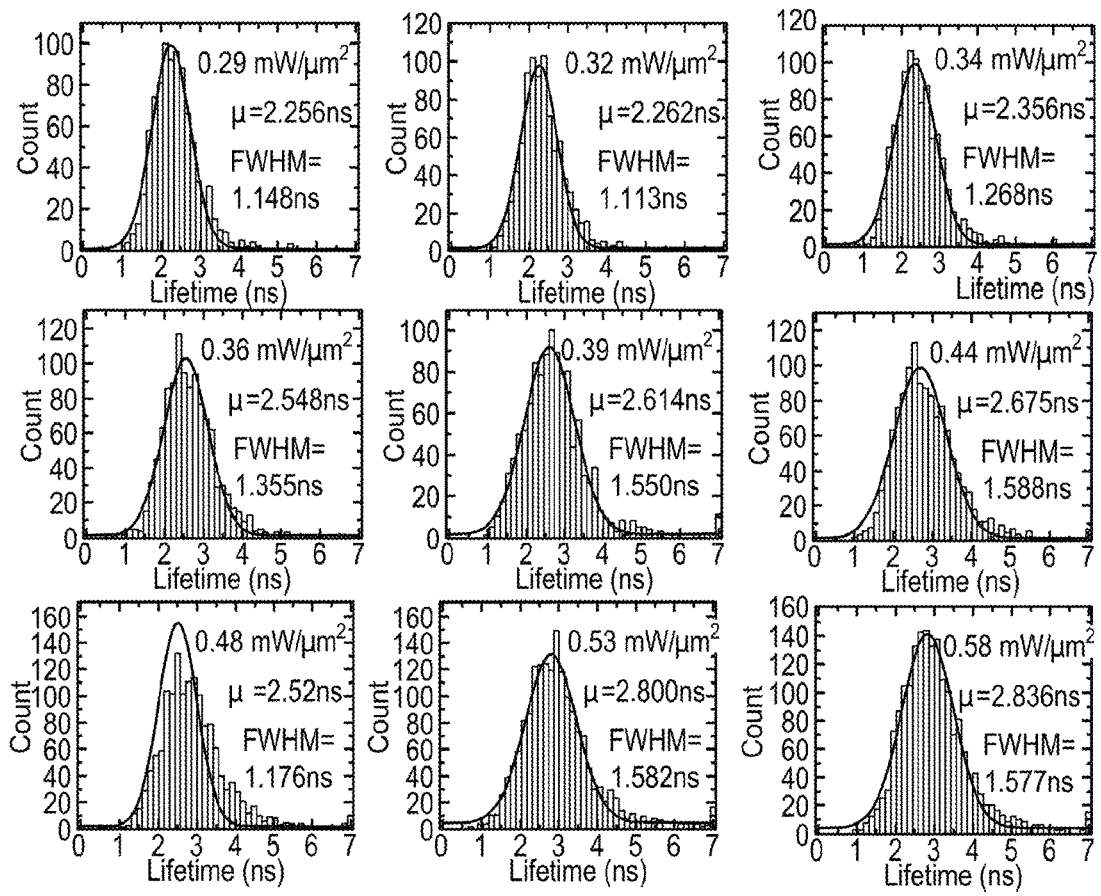
FIG. 93 shows the histogram and Gaussian fits of the lifetime of quantum dots patterned at various powers. Each histogram is obtained from isolating the lifetimes of each line patterned in FIG. 91, and plotting the separately. For instance, the first histogram is obtained from all the lifetime of all the pixels comprising the bottom most line in FIG. 91. A gradual increase in the FWHM is observed as power increases.

In order to investigate the dynamics of the interaction between the quantum dot exciton and the plasmonic cavity, time-resolved fluorescence measurements were performed to study the influence on spontaneous emission rate. A femtosecond Ti:Sapphire laser (800 nm) was used for two-photon excitation, of the quantum dots post patterning. The average laser power was 1 mW corresponding to the relatively low fluence at the focal point of 7×10$^{10}$ w/cm$^2$. FIG. 89 shows the normalized counts from the quantum dot aggregate emission with various patterning conditions. The shortening of the lifetime upon introduction of quantum dots over gold nanoislands can be ascribed to the Purcell effect arising from the proximity of quantum dots to the hot spots in the gold nanoisland film (Hoang T B et al. *Nat Commun*, 2015, 6, 7788). The field profile of gold nanoisland film is shown in FIG. 57. A three-fold reduction in the average lifetime to $\tau_{BP-AuNI}$=2.69±0.29 is observed upon bubble printing quantum dots over the gold nanoislands, which is attributed to a combination of superior adhesion resulting in reduced quantum dot-gold nanoisland separation, and the mild oxidation phenomenon which can alter the recombination dynamics (Pietryga J M et al. *Chem Rev.* 2016, 116(18), 10513-10622). Further, the influence of the printing conditions over the emission rate of the quantum dot aggregates was analyzed by performing fluorescence lifetime imaging (FLIM) as per the setup shown in FIG. 90. Straight lines of quantum dots were printed with increasing incident laser intensity from 0.29 mW/μm$^2$ to 0.58 mW/μm$^2$, and the FLIM generated by scanning the laser over the sample area (FIG. 91). FIG. 92 shows histogram of the lifetimes obtained from each line fabricated at various power intensities along with the Gaussian fit of the lifetime distribution. The lifetime distribution for each power is statistically significant with ~1000 pixels analyzed for each dataset (FIG. 93). The mean lifetime increases from 2.256 ns at 0.29 mW/μm$^2$ to 2.836 ns at the maximum power intensity of 0.58 mW/μm$^2$. The increase is due to larger separation between quantum dots and gold nanoislands as power increases, which is evident via the atomic force microscopy (AFM) and optical profilometry images (FIG. 91). The atomic force microscopy (AFM) images were taken with Park Scientific AFM under the non-contact mode. Further, the lifetime distribution broadens at higher power owing to higher thickness variations in the quantum dots printed. The lifetime tunability will find applications as an encoding scheme to produce distinguishable optical codes and study biological processes.

Figure 55:
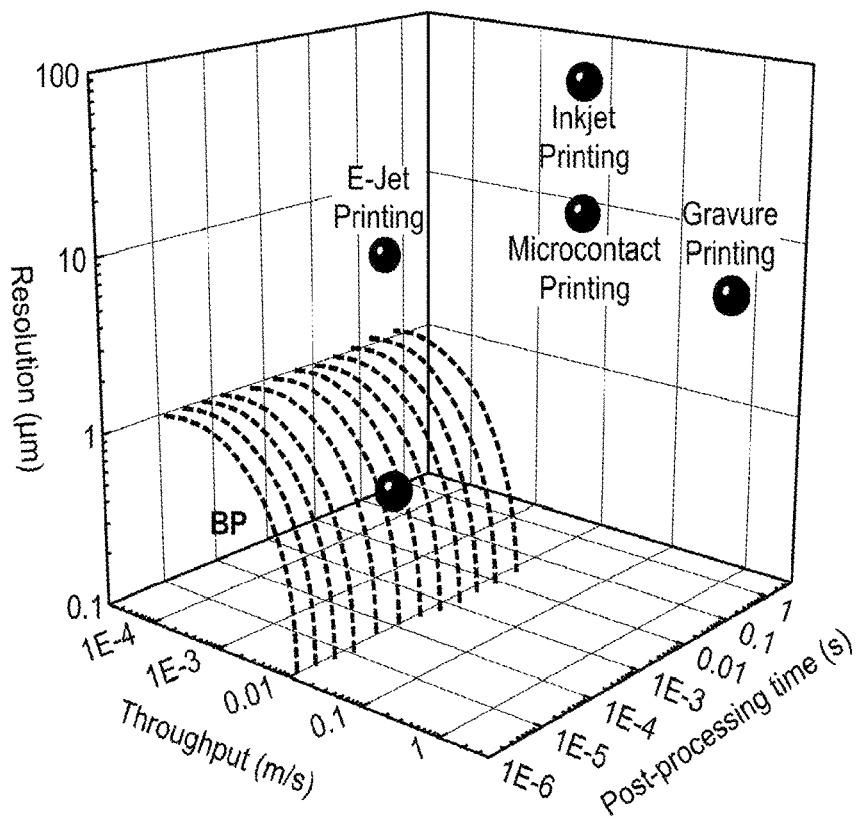
FIG. 55 shows a comparison of patterning metrics (Resolution, throughput, and post-processing time) of various printing techniques currently being explored. Bubble printing (BP), with a high throughput and resolution outweighs other technologies.

In conclusion, a quantum dot printing technique, termed bubble printing, was developed and used to fabricate hybrid plasmonic-quantum dot structures. Bubble stability over a large area is attributed to the delocalized temperature increase over uniform gold nanoparticles on the gold nanoisland substrate. Further, vapor bubbles exhibiting fast bubble dissolution times enable an improved throughput. In contrast to previous printing techniques, bubble printing can achieve high resolution (<1 μm linewidth), high throughput (>10$^5$ μm/s) and low material usage simultaneously (FIG. 55). The printing capabilities were demonstrated for multi-color quantum dots on both rigid and flexible substrates, along with haptic interfacing. The capability of bubble printing to modify the quantum dot emission via controlled thermal oxidation, along with increased emission rate enhancement dependent on the nanoparticle-quantum dot separation distance, was also demonstrated. High resolution bubble printing can be utilized for fabrication of ultra-high resolution displays and high-density information storage.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method comprising:
   illuminating a first location of a plasmonic substrate with electromagnetic radiation at a power density of 10 mW/µm² or less;
   wherein the electromagnetic radiation comprises a wavelength that overlaps with at least a portion of the plasmon resonance energy of the plasmonic substrate; and
   wherein the plasmonic substrate is in thermal contact with a liquid sample comprising a plurality of particles;
   thereby:
   generating a bubble at a location in the liquid sample proximate to the first location of the plasmonic substrate by plasmon-enhanced photothermal effects, the bubble having a gas-liquid interface with the liquid sample;
   trapping at least a portion of the plurality of particles at the gas-liquid interface of the bubble and the liquid sample; and
   depositing at least a portion of the plurality of particles on the plasmonic substrate at the first location.

2. The method of claim 1, wherein the electromagnetic radiation is provided by a light source and the light source is a laser.

3. The method of claim 1, wherein the plasmonic substrate comprises a plurality of plasmonic particles.

4. The method of claim 3, wherein the plurality of plasmonic particles comprise a plurality of metal particles and the plurality of metal particles comprise a metal selected from the group consisting of Au, Ag, Pd, Cu, Cr, Al, and combinations thereof.

5. The method of claim 3, wherein the plurality of plasmonic particles have an average particle size of from 10 nm to 300 nm.

6. The method of claim 3, wherein each plasmonic particle within the plurality of plasmonic particles on the substrate is separated from its neighboring plasmonic particles by an average distance of from 5 nm to 100 nm.

7. The method of claim 1, wherein the plurality of particles in the liquid sample comprise a plurality of thermoresponsive particles.

8. The method of claim 1, wherein the plurality of particles comprise a plurality of polystyrene spheres, a plurality of silica spheres, a plurality of quantum dots, a plurality of semiconductor nanowires, a plurality of biological cells, or a combination thereof.

9. The method of claim 1, wherein the portion of the plurality of particles are not damaged during the deposition.

10. The method of claim 1, wherein the portion of the plurality of particles deposited is one particle.

11. The method of claim 1, wherein the portion of the plurality of particles is deposited in an amount of time from 1 milliseconds to 5 seconds.

12. The method of claim 1, wherein the portion of the plurality of particles are trapped by convection, surface tension, gas pressure, substrate adhesion, or combinations thereof.

13. The method of claim 1, wherein the portion of the plurality of particles deposited on the substrate are immobilized on the plasmonic substrate by surface adhesion; wherein the plasmonic substrate further comprises a ligand and the portion of the plurality of particles deposited on the substrate are immobilized on the plasmonic substrate by electrostatic attraction and/or chemical recognition with the ligand; or a combination thereof.

14. The method of claim 1, wherein an additional layer is present between the plasmonic substrate and the liquid sample, the additional layer being in thermal contact with the plasmonic substrate and the liquid sample, such that the plurality of particles are deposited on the additional layer, and the additional layer comprises a two-dimensional atomic layer material.

15. The method of claim 14, wherein the additional layer comprises $MoS_2$, $WSe_2$, $MoTe_2$, $WS_2$, hexagonal BN, graphene, or combinations thereof.

16. The method of claim 1, further comprising illuminating a second location of the plasmonic substrate to deposit another portion of the plurality of particles at the second location.

17. The method of claim 16, wherein the plasmonic substrate is translocated to illuminate the second location; wherein the electromagnetic radiation is provided by a light source, and the light source is translocated to illuminate the second location; or a combination thereof.

18. A patterned substrate made using the method of claim 1.

19. A method of use of the patterned substrate of claim 18, wherein the patterned substrate is used for single-particle sensing, single-cell analysis, tissue engineering, functional optical devices, or combinations thereof.

20. A system comprising:
   a plasmonic substrate in thermal contact with a liquid sample comprising a plurality of particles; and
   a light source configured to illuminate the plasmonic substrate at a first location with electromagnetic radiation at a power density of 10 mW/µm² and at a wavelength that overlaps with at least a portion of the plasmon resonance energy of the plasmonic substrate; thereby:

generating a bubble at a location in the liquid sample proximate to the first location of the plasmonic substrate, the bubble having a gas-liquid interface with the liquid sample;

trapping at least a portion of the plurality of particles at the gas-liquid interface of the bubble and the liquid sample; and depositing at least a portion of the plurality of particles on the plasmonic substrate at the first location.

* * * * *